United States Patent
Sage et al.

(10) Patent No.: US 11,028,364 B2
(45) Date of Patent: Jun. 8, 2021

(54) COMPOSITIONS AND METHODS FOR MODULATING AN IMMUNE RESPONSE

(71) Applicant: President and Fellows of Harvard College, Cambridge, MA (US)

(72) Inventors: Peter T. Sage, Brookline, MA (US); Arlene H. Sharpe, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 164 days.

(21) Appl. No.: 15/778,524

(22) PCT Filed: Nov. 23, 2016

(86) PCT No.: PCT/US2016/063604
§ 371 (c)(1),
(2) Date: May 23, 2018

(87) PCT Pub. No.: WO2017/091729
PCT Pub. Date: Jun. 1, 2017

(65) Prior Publication Data
US 2018/0340147 A1    Nov. 29, 2018

Related U.S. Application Data

(60) Provisional application No. 62/300,339, filed on Feb. 26, 2016, provisional application No. 62/258,876, filed on Nov. 23, 2015.

(51) Int. Cl.
| | | |
|---|---|---|
| *C12N 5/0783* | (2010.01) | |
| *A61K 35/26* | (2015.01) | |
| *A61K 39/395* | (2006.01) | |
| *C07K 16/00* | (2006.01) | |
| *A61K 39/39* | (2006.01) | |
| *A61K 39/00* | (2006.01) | |
| *C07K 16/24* | (2006.01) | |

(52) U.S. Cl.
CPC ............ *C12N 5/0637* (2013.01); *A61K 35/26* (2013.01); *A61K 39/39* (2013.01); *A61K 39/395* (2013.01); *C07K 16/00* (2013.01); *A61K 2039/515* (2013.01); *A61K 2039/5158* (2013.01); *A61K 2039/55511* (2013.01); *A61K 2039/55522* (2013.01); *A61K 2039/55527* (2013.01); *C07K 16/248* (2013.01); *C07K 2317/14* (2013.01); *C12N 2501/2302* (2013.01); *C12N 2501/2306* (2013.01); *C12N 2501/2321* (2013.01); *C12N 2501/515* (2013.01); *Y02A 50/30* (2018.01)

(58) Field of Classification Search
None
See application file for complete search history.

(56) References Cited

FOREIGN PATENT DOCUMENTS

| WO | WO-2010/003002 A2 | 1/2010 |
| WO | WO-2014/074852 A1 | 5/2014 |

OTHER PUBLICATIONS

Chung et al. "Follicular regulatory T (Tfr) cells with dual Foxp3 and Bcl6 expression suppress germinal center reactions," Nat Med, Jul. 24, 2011 (Jul. 24, 2011), vol. 17, No. 8, pp. 983-988.
Park et al. "Insights into the Role of Follicular Helper T cells in Autoimmunity," Immune Network, Feb. 24, 2014 (Feb. 24, 2014), vol. 14, No. 1, pp. 21-29.
Sage et al. "T Follicular Regulatory Cells in the Regulation of B cell Responses," Trends Immunol, Jun. 17, 2015 (Jun. 17, 2015), vol. 36, No. 7, pp. 410-418.
International Search Report dated Feb. 16, 2017 issued in International Application No. PCT/US2016/063604.
Davis et al., "Clinical and Biological Efficacy of Recombinant Human Interleukin-21 in Patients with Stage IV Malignant Melanoma without Prior Treatment: A Phase IIa Trial," Clin Cancer Res 15(6):2123-2129 (2009).
Ding et al., "Interleukin-21 Promotes Germinal Center Reaction by Skewing the Follicular Regulatory T Cell to Follicular Helper T Cell Balance in Autoimmune BXD2 Mice," Arthritis Rheumatol 66(9):2601-2612 (2014).
Extended European Search Report for EP application No. EP16869273 dated Jul. 2, 2019.
Feng et al., "Interleukin-21 Inhibits Humoral Response to an HIV DNA Vaccine by Enhancing Bcl-6 and Pax-5 Expression," Viral Immunol 25(2):131-140 (2012).

*Primary Examiner* — Daniel C Gamett
(74) *Attorney, Agent, or Firm* — Foley Hoag LLP

(57) ABSTRACT

The invention provides methods of modulating follicular regulatory T (TFR) cell-mediated immune responses and the use of those methods in the treatment of diseases or conditions such as viral, bacterial, pathogenic, or fungal infections or cancer. Such methods provide for boosting of antibody production through the use of IL-21 to overcome TFR cell suppression of antibody production.

21 Claims, 65 Drawing Sheets

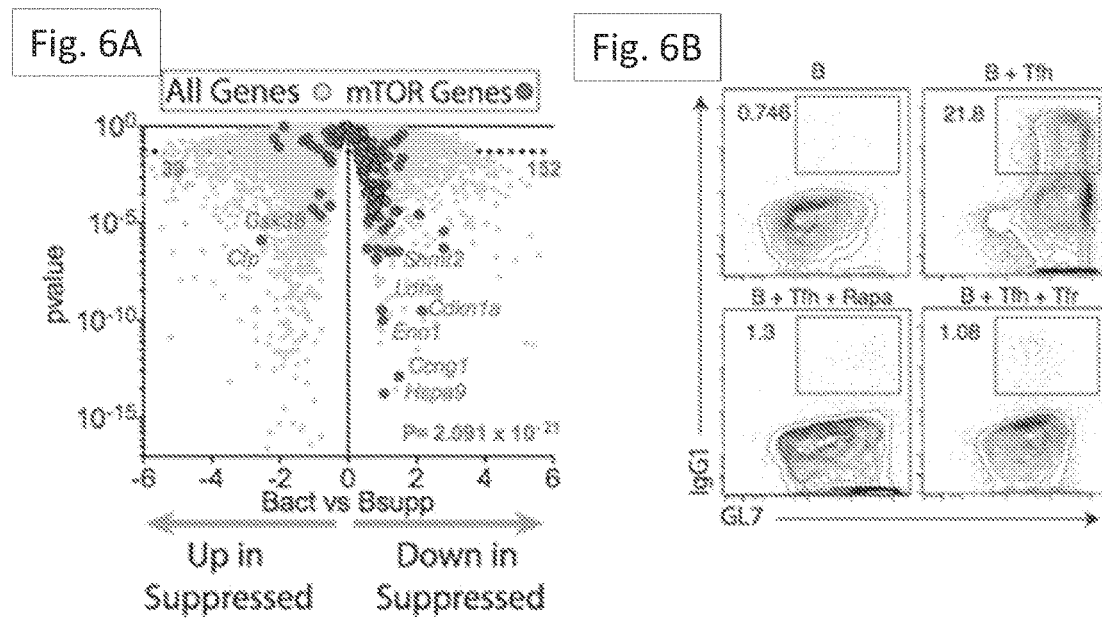
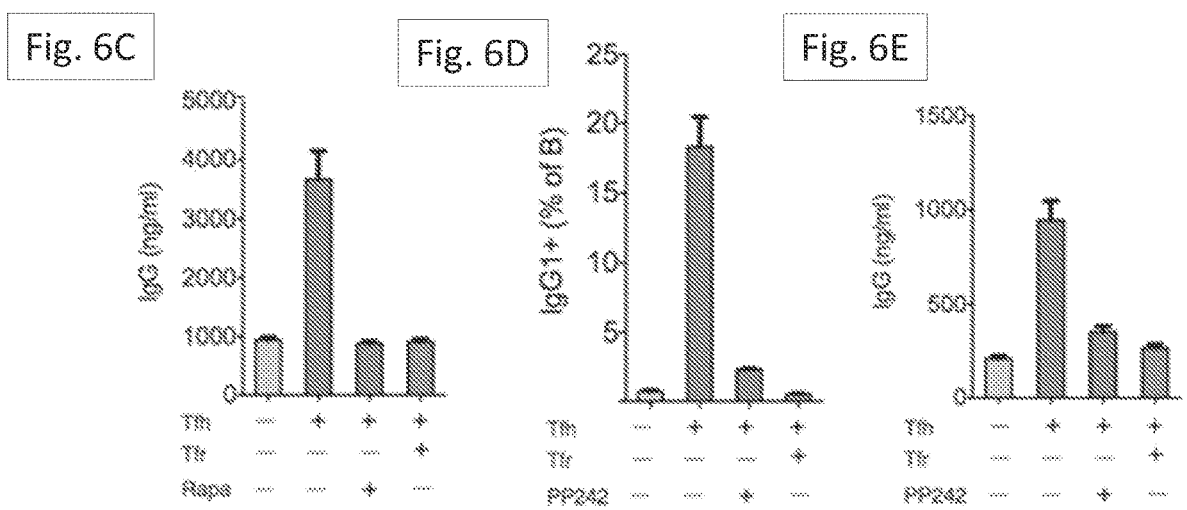

eFluor670 (B cells)
FoxP3 (T$_{FR}$ cells)
Membrane (B + T$_{FH}$ + T$_{FR}$)

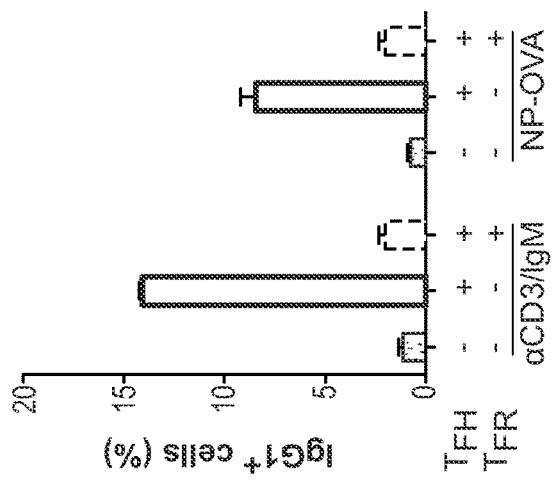
FIG. 36A
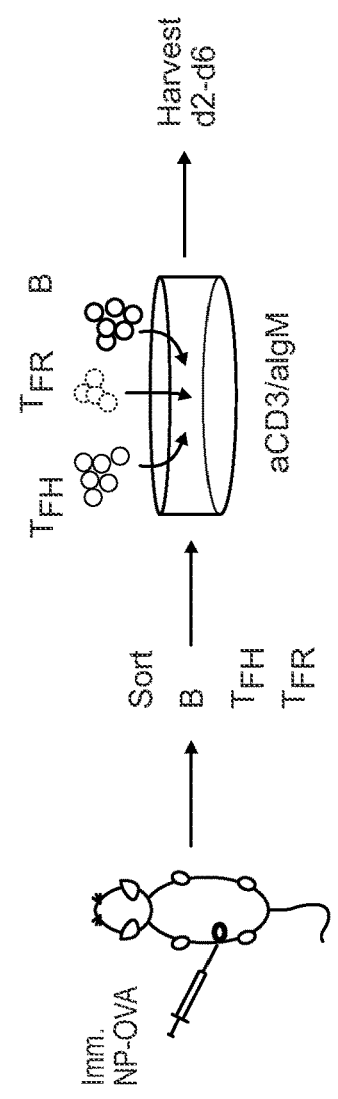
FIG. 36C
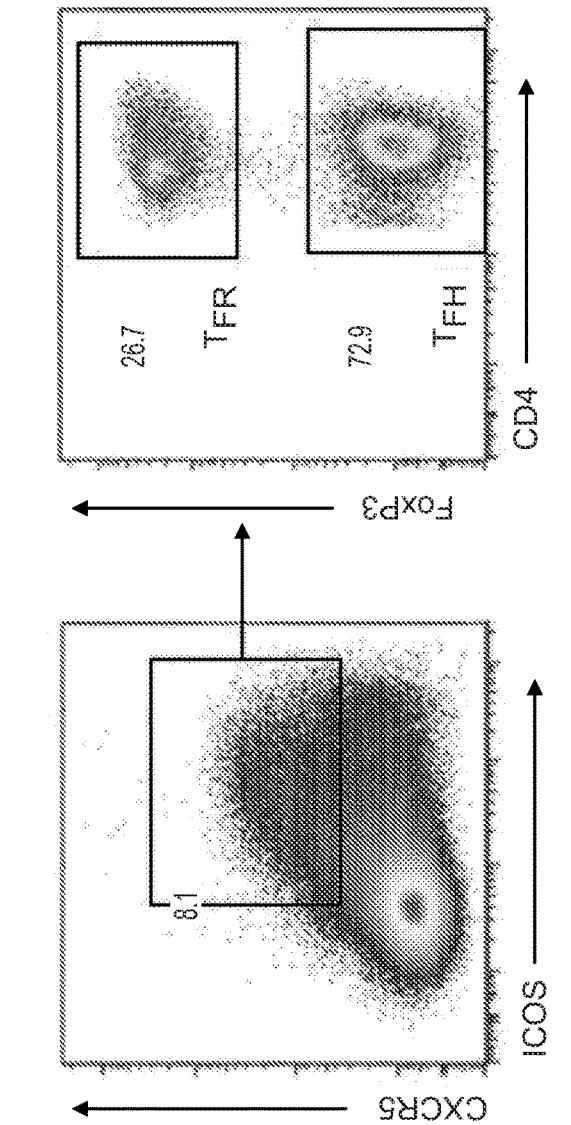
FIG. 36B
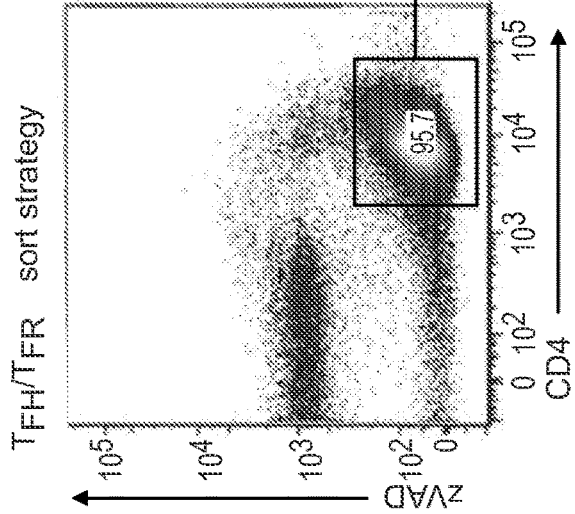

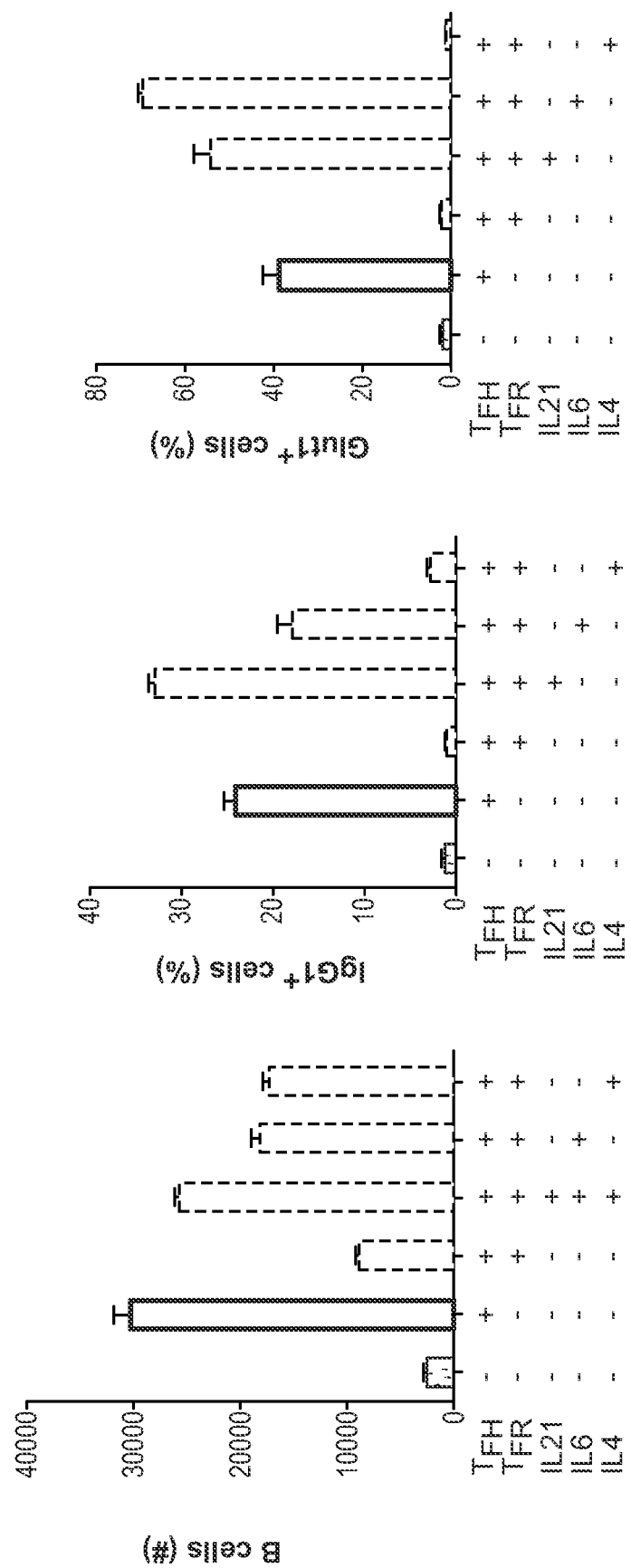

Not Rescued with IL-21

Act | Supp | Supp+21

FIG. 40C

Ackr2
Tcf7l2
Ccr1
Itgam
Flt3
Ap5b1
Cdh17
Pik3r6
Fut8
Rhoh
Hck
Ighg2b
Gsap
Cpd
Fcrl1
Blvrb
Cfp
Flna
Bin1
Rara
Vim
Trabd2b
Bank1
Cyth4
Zeb2
Fcgr2b
Pirb
Pld4
Pitpnc1
Slc22a15
Slc6a13
Tgfb1i1
Trps1
Ighm
Mtdh
Ccng1
Cdkn1a
Pglc1
Eif4ebp1
Aicda
Klhdc2
Tram2
Gfi1
Nabp1
Ubd
Lef1
Pim2
Satb1
Thy1
Gapdh
Sertad4
Gnaz
Psrc1

COMPOSITIONS AND METHODS FOR MODULATING AN IMMUNE RESPONSE

RELATED APPLICATIONS

This application is the U.S. National Stage of International Patent Application No. PCT/US2016/063604, filed Nov. 23, 2016, which claims the benefit of priority to U.S. Provisional Patent Application Ser. No. 62/258,876, filed Nov. 23, 2015 and U.S. Provisional Patent Application Ser. No. 62/300,339, filed Feb. 26, 2016. The contents of each of which are hereby incorporated by reference in their entirety.

BACKGROUND

Regulation of immune responses is central for the prevention of inflammatory and autoimmune disorders. While downregulation of the immune system can be achieved by way of immunosuppressive therapy, agents that generally suppress the immune system leave subjects susceptible to other disorders, including infections and cancers. A means for controlling the aberrant activation of an immune response to specific antigens would be a major advance in the treatment of autoimmune disorders, graft versus host disease and the side effects of gene therapy, as it would allow downregulation of the immune response against a particular target antigen, but would otherwise leave the immune system functional against invading pathogens and tumor associated antigens. Conversely, methods of specifically improving immunogenicity of specific antigens to which immune responses are desired would be of tremendous benefit in promoting desired immune responses, for example in the context of vaccination and promoting responsiveness to antigens including tumor antigens.

T helper (Th) cells are a class of CD4+ cells that function to regulate the proliferation of B cells and B cell responses. Th cells play an importance role in humoral immunity and immunopathology. Follicular helper T cells (TFH) are a recently defined subset of CD4+ T cells that are essential for helping cognate B cells form and maintain the germinal center (GC) reaction, and for development of humoral immune responses. These cells are universally defined by expression of the chemokine receptor CXCR5, which directs them to the B cell follicles via gradients of the chemokine CXCL13 1. TFH cells also express the transcription factor Bcl6 (which represses Blimp-1/Prdm1) and high levels of the costimulatory receptor ICOS, which are both critical for their differentiation and maintenance 1-4. In addition, TFH cells secrete large amounts of IL-21, which aids in GC formation, isotype switching and plasma cell formation 5. In humans and mice functionally similar TFH cells can be found in secondary lymphoid organs. CXCR5+ TFH cells are also present in peripheral blood and seen at elevated levels in individuals with autoantibodies, including systemic lupus erythematosus, myasthenia gravis and juvenile dermatomyositis patients. However, the function of these circulating TFH remains unclear 6-9.

Regulatory T cells (Tregs) have pluripotent anti-inflammatory effects on multiple cell types. In particular they control the activation of innate and adaptive immune cells. Tregs acting in an antigen-specific manner reduce effector T cell activation and function, for example, after effector T cells have successfully mounted an attack against an invading pathogen, or to suppress reactivity to self-antigen and thereby prevent autoimmune disease.

Two subsets of Tregs are classified according to the location at which they develop in vivo. Naturally occurring Tregs (nTreg) develop in the thymus and suppress self-reactive immune responses in the periphery, whereas adaptive Tregs (aTreg) develop in the periphery from conventional CD4+ T cells to ensure tolerance to harmless antigens, including those derived from, for example, food and intestinal flora.

Both subsets of Treg cells are characterized by expression of high levels of CD25 and the transcription factor Foxp3. Tregs are thought to inhibit the antigen-specific expansion and/or activation of self-reactive effector T cells and to secrete suppressive cytokines, including TGF or IL-10. Because of their potential to provide antigen-specific immune regulation without generalized immunosuppression, Tregs have been contemplated for use in cell-based therapy for inflammatory or autoimmune disorders.

T follicular regulatory (TFR) cells are newly defined subset of CD4+CXCR5+ cells which are positive for the transcription factors FoxP3, Bcl6 and Prdm1/Blimp1 and function to inhibit the germinal center response21-23. The present inventors have discovered how TFR cells suppress antibody production, and how a specific cytokine can overcome this suppression to boost antibody production. This discovery has elucidated novel approaches to modulating an immune response for use in therapy

SUMMARY

The present inventors have discovered that TFR cells derived from the peripheral blood of a subject are potent inhibitors of TFH mediated antibody production but do not inhibit other arms of the immune system. Compositions comprising TFR cells may be isolated from the peripheral blood of a subject. The compositions may be enriched for the peripheral blood TFR cells by purifying TFR cells from other PMBCs and optionally sorting for TFR cells based on surface markers. Compositions of TFR cells derived from peripheral blood may also be expanded and/or activated to produce a clonal population of TFR cells based on the original population of TFR cells derived from the peripheral blood of the patient.

The present inventors have discovered that B and TFH cells are changed by TFR suppression. Suppressed TFH cells have defective cytokine production but still express TFH program and are metabolically reprogrammed. Suppressed B cells have a distinct suppressed gene signature and are metabolically reprogrammed, such that inhibiting general metabolic pathways (e.g., blocking purine/1C metabolic pathway) resembles or recapitulates TFR suppression.

The inventors have also discovered that increasing the ratio of TFR cells to TFH cells in a subject prior to, or during an immune response by the subject, inhibits antibody production. Therefore, the invention provides a method for suppressing an immune response in a subject wherein suppression of an immune response is desired, comprising increasing the ratio of TFR cells to TFH cells by administering a composition enriched with TFR cells derived from the peripheral blood of a subject (or an expanded/activated population thereof) or administering a composition comprising TFR cells having enhanced suppressive activity.

The invention also provides methods of boosting antibody production in a subject comprising contacting a TFR or TFH cell with a specific cytokine (e.g., IL-21, IL-6) to limit TFR suppression of antibody production.

The compositions of TFR cells and TFH cells of the invention are also useful as adjuvants as a part of a vaccination regimen. When used in this manner, the compositions enhance the efficacy of such vaccines.

The invention further provides compositions and methods for enhancing a protective antibody response in a patient comprising selectively modulating TFH or TFR cells with agents (e.g. cytokines like IL-21 or IL-6) in amounts effective to enhance a protective antibody response or boost antibody production or response in a patient.

One aspect of the invention relates to a composition comprising T follicular regulatory (TFR) or TFH cells and a cytokine, wherein said composition has enhanced immune activity.

In some embodiments, the enhanced immune activity are characterized by a boost in antibody production in vitro and in vivo as compared to native TFR cells.

In some embodiments, the enhanced immune activity is a protective antibody response.

In some embodiments, the cytokine is IL-21. In some embodiments, the cytokine is IL-6

Another aspect of the invention relates to a method of preparing a composition comprising TFR cells having reduced activity comprising the steps of:
 a) obtaining an initial population of cells comprising TFR cells, T regulatory (Treg) progenitor cells, or both;
 b) contacting the cells ex vivo in the presence of a cytokine; and
 c) isolating the TFR cells from the population wherein the isolated TFR cells have reduced immune activity.

In some embodiments, the reduced activity results in a boost in antibody production.

In some embodiments, the initial population of cells is isolated from the peripheral blood, tissues or organs of one or more subjects.

In some embodiments, the method further comprising sorting TFR cells and Treg progenitor cells from the cell population prior to contacting the cell with the cytokine.

In some embodiments, the method further comprising the step of expanding the cell population.

Another aspect of the invention relates to a method of modulating an immune response in a subject in need thereof comprising:
 administering to the subject a) an effective amount of a composition comprising T follicular regulatory (TFR) cells and a cytokine.

In some embodiments, the TFR cells are administered conjointly or in combination with the cytokine.

In some embodiments, the TFR cells are contacted with the cytokine prior to administering to the subject.

In some embodiments, the TFR cells are isolated from the peripheral blood of a subject.

In some embodiments, the TFR cells modulation results in boosted antibody production.

In some embodiments, the method further comprises administering a vaccine to the subject.

In some embodiments, the method further comprises co-administering a composition comprising TFH cells and a vaccine.

In some embodiments, the composition is administered intravenously.

In some embodiments, the subject is afflicted with a disease or condition selected from the group consisting viral infection, bacterial infection, pathogenic infection, fungal infection, and cancer.

Another aspect of the invention relates to an adjuvant comprising a composition of TFH cells and a cytokine having enhanced immune activity.

In some embodiments, the TFH cells are purified from the peripheral blood of a subject.

In some embodiments, the adjuvant further comprises TFH cells purified from the peripheral blood of a subject, TFH cells having enhanced stimulatory capacity or any combination thereof.

Another aspect of the invention relates to a method of upregulating an immune response in a subject comprising administering to the subject, an effective amount of the composition comprising T follicular regulatory (TFR) cells and a cytokine.

Another aspect of the invention relates to a vaccine comprising the composition comprising T follicular regulatory (TFR) cells and a cytokine.

Another aspect of the invention relates to a method of boosting antibody production in a subject in need thereof comprising administering to the subject the adjuvant comprising a composition of TFR cells and a cytokine.

Another aspect of the invention relates to a method of increasing a protective antibody response in a subject in need thereof comprising administering to the subject a first agent capable of modulating TFR cell suppression in an amount effective to decrease TFR cell-mediated antibody suppression in the subject.

In some embodiments, the method further comprises administering a second agent capable of modulating a selective TFH receptor in an amount effective to increase TFH cell-mediated antibody production, wherein the protective antibody response is increased as compared to the protective antibody response in the absence of the first or second agents.

In some embodiments, the second agent is administered conjointly, in combination, or subsequently to the first agent. In some embodiments, the second agent is a vaccine.

In some embodiments, the first agent is a cytokine.

In some embodiments, the subject is afflicted with a disease or condition selected from the group consisting viral infection, bacterial infection, pathogenic infection, fungal infection, and cancer.

In some embodiments, the protective antibody response reduces or eliminates the causes or pathogenesis of the disease.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description

BRIEF DESCRIPTION OF FIGURES

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 1A is a schematic of suppression assay. FoxP3-GFP reporter mice were immunized with NP-OVA and 7 days later dLN were harvested and CD19+ B cells and CD4+CXCR5+ICOS+FoxP3-CD19− TFH were cultured with or without CD4+CXCR5+ICOS+FoxP3+ CD19− TFR cells in the presence of anti-CD3/IgM. (FIG.

1B) Class switched IgG1+GL7+B cells (left) and antibody measurements (right) from suppression assays as in (FIG. 1A) cultured for 6 days. B cells are pregated on CD19+IA+ CD4−. (FIG. 1C) Proliferation of B cells measured by Cell Trace Violet (CTV) dilution from suppression assays as in (FIG. 1A) cultured for 6 days. B cells are pregated on CD19+IA+CD4− (FIG. 1D) CD69 expression time course on B cells from suppression assays as in (Panel a). B cells are pregated on CD19+IA+CD4− (FIG. 1E) Cell death in B cells measured by zVAD staining in suppression assays as in (FIG. 1A). B cells are pregated on CD19+IA+CD4− (FIG. 1F) Somatic hypermutation in B cells in suppression assays. After culture for 6 days, CD19+IA+CD4− B cells were sorted and somatic hypermutation was assessed using the ImmunoSeq platform. Error bars indicate standard error. *p<0.05, p<0.01, *p<0.001.

(FIG. 2A) Schematic of experiment. B and TFH sorted from NP-OVA immunized FoxP3-GFP mice were cultured alone ("Activated") or with TFR cells ("Suppressed") sorted from FoxP3-GFP Actin-CFP mice in the presence of NP-OVA. After 4 days CD19+I-A+CD4-CFP− B and CD4+CD19-I-A-CFP− TFH cells were sorted and subjected to RNAseq analysis. (FIG. 2B) Principle component analysis of activated and suppressed B and TFH cells. (FIG. 2C) Venn diagram of differentially expressed (FDR adjusted p<0.05) genes in activated versus suppressed B and TFH cells. (FIG. 2D) (Left) Volcano plot showing data from all genes or TFH genes in TFH cells in activated versus suppressed cultures. (Right) Heat map showing TFH genes in activated and suppressed TFH cells. (FIG. 2E) Single sample GSEA showing correlation of activated B, activated TFH and suppressed TFH cells to ImmSig datasets (GSE11924, GSE16697, GSE21380, GSE24574). (FIG. 2F) Expression of B cell function gene transcripts in activated or suppressed B cells. (FIG. 2G) Volcano plot showing data from all genes or B cell function genes in activated versus suppressed B cells. (FIG. 2H) Single sample GSEA showing correlation of activated or suppressed B cells to ImmSig datasets (GSE12366, GSE12845).

(FIG. 5A) Volcano plot showing RNA-seq data from FIG. 2A-FIG. 2H with all genes or Myc pathway (Hallmark_MYC_TARGETS_V1) genes in activated versus suppressed B cells. Significance was measured using Chi2 test. (FIG. 5B) Class switch recombination measured by IgG1+GL7+ expression in B cells from suppression assays performed as in FIG. 1A-FIG. 1F with the addition of the Myc inhibitor 10058-F4 (F4). (FIG. 5C) Class switched IgG antibody levels in culture supernatants from suppression assays in (FIG. 5B). (FIG. 5D) Class switch recombination measured by IgG1+GL7+ expression (left) or GL7 expression (right) in B cells from suppression assays in which control (WT) or Myc overexpressing (Myc) B cells were cultured with TFH alone or along with TFR cells in the presence of anti-CD3/IgM. (FIG. 5E) Class switched IgG antibody levels in culture supernatants from assays as in (FIG. 5D).

FIG. 6A-FIG. 6G show inhibition of the mTOR/AKT pathways inhibits B cells similarly as TFR Cells. (FIG. 6A) Volcano plot showing RNA-seq data from FIG. 2A-FIG. 2H with all genes or mTOR signaling (Hallmark_MTORC1_SIGNALING) genes in activated versus suppressed B cells. Significance was measured using Chi2 test. (FIG. 6B) Class switch recombination measured by IgG1+GL7+ expression in B cells from suppression assays performed as in FIG. 1A-FIG. 1F with the addition of the mTOR inhibitor rapamycin (Rapa). (FIG. 6C) Class switched IgG antibody levels in culture supernatants from suppression assays in (FIG. 6B). (FIG. 6D) Class switch recombination measured by IgG1+GL7+ expression in B cells from suppression assays performed as in (FIG. 6B) with the addition of the mTOR inhibitor PP242. (FIG. 6E) Class switched IgG antibody levels in culture supernatants from suppression assays in (FIG. 6D). (FIG. 6F) Class switch recombination measured by IgG1+GL7+ expression in B cells from suppression assays performed as in (FIG. 6B) with the addition of an AKT inhibitor (Akt-i). (FIG. 6G) Class switched IgG antibody levels in culture supernatants from suppression assays in (FIG. 6B).

(FIG. 7A) Heat map of average expression of genes from RNAseq data in metabolic pathways. (FIG. 7B) Schematic of key enzymes in glycolysis, TCA and 1-Carbon metabolism with genes downregulated in suppressed B cells compared to activated B cells and genes upregulated in suppressed B cells. (FIG. 7C) Glut1 expression in B (left) and TFH (right) cells from activated or suppressed cultures. (FIG. 7D) Glucose uptake measured in culture supernatants from cultures as in (FIG. 7C). (FIG. 7E) Lactate production measured in culture supernatants from cultures as in (FIG. 7C). (FIG. 7F) Glutamine uptake measured from culture supernatants from cultures as in (FIG. 7C). (FIG. 7G) Class switched IgG antibody levels in culture supernatants from cultures as in (FIG. 7C) with the addition of the glucose analog 2-deoxyglucose (2DG), 3-nitropropionic acid (3-NPA) or dichloroacetate (DCA). (FIG. 7H) Volcano plot of activated versus suppressed B cells showing all genes or genes involved in 1-Carbon/Serine/Purine metabolism. (FIG. 7I) Class switched antibody levels in supernatants of cocultures as in (FIG. 7C) with the addition of Methotrexate (MTX). (FIG. 7J) Class switched antibody levels in supernatants of cocultures as in (Panel c) with the addition of Azathioprine (AZA). *p<0.05, p<0.01, *p<0.001.

(FIG. 8Aa) Schematic of restimulation assay. FoxP3-GFP mice were immunized with NP-OVA and 7 days later B and TFH cells were sorted and cultured alone or with TFR cells in the presence of anti-CD3/IgM. After 3 days, B cells from the activated culture (Act B) or suppressed culture (Supp B) were sorted and cultured with TFH cells from FoxP3-GFP immunized mice in the presence of anti-CD3/IgM for 6 days. (FIG. 8B) Intracellular Bcl6 and Ki67 in TFH cells from cultures as in (FIG. 8A). (FIG. 8C) Class switched (IgG1+GL7+) B cells were analyzed from cultures as in (FIG. 8A). (FIG. 8D) Glut1 expression in B cells from cultures as in (FIG. 8A). (FIG. 8E) Glucose uptake in supernatants from cultures as in (FIG. 8A). (FIG. 8F) Venn diagram showing genes downregulated in B cells upon suppression from RNA-seq data from FIG. 2A-FIG. 2H along with genes showing evidence of inaccessibility in B cells upon suppression measured by ATAC-seq. (FIG. 8G) (Left) RNA-seq data sorted by ascending ATAC-seq p-value for genes downregulated in suppressed B cells by RNA-seq and measured to be less accessible by ATAC-seq. (Right)

Expression tracks, gene track and peak track for Aicda and Pou2af1 from ATAC-seq data. *p<0.05, p<0.01, *p<0.001.

Figure 9:
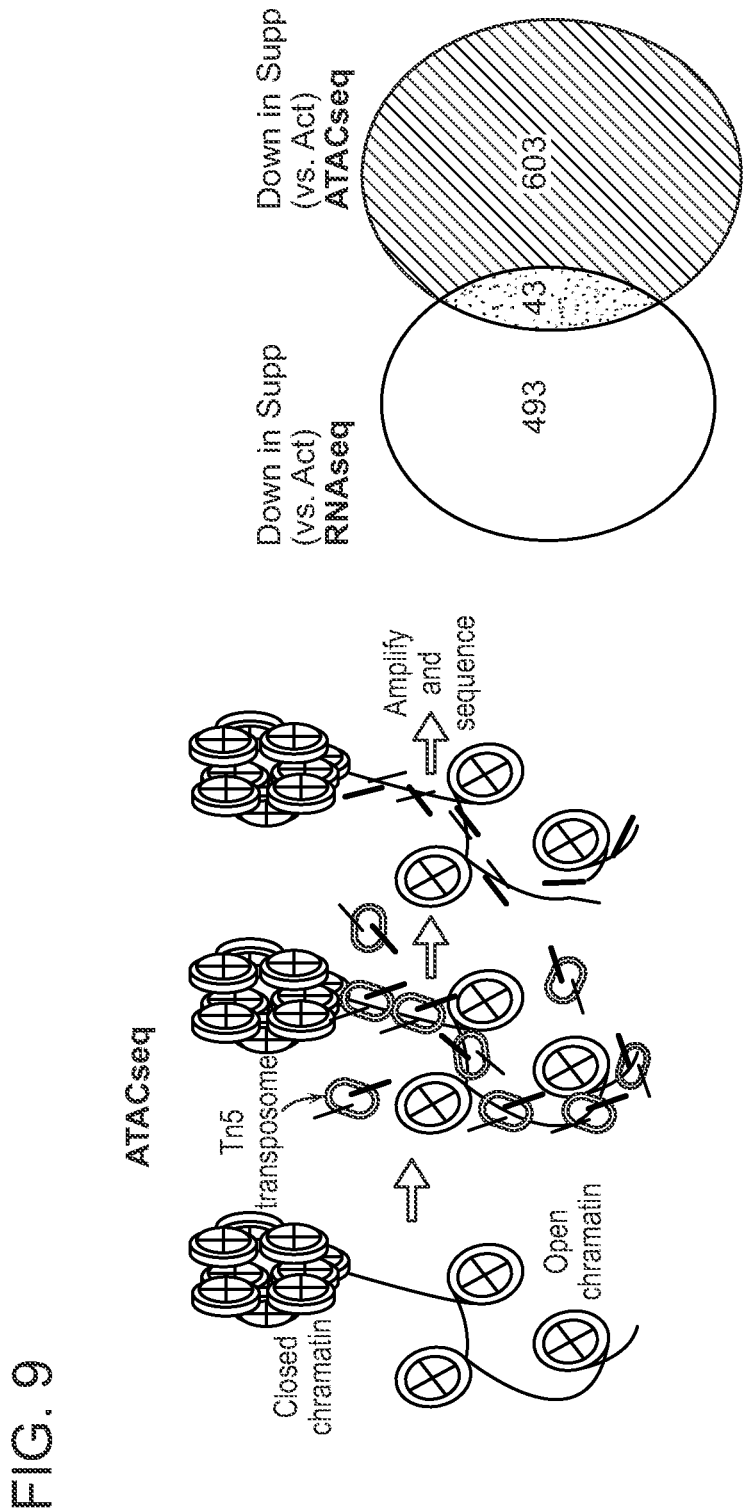

FIG. 9 shows that epigenetic modification of B cells during TFR cell suppression.

Figure 10:
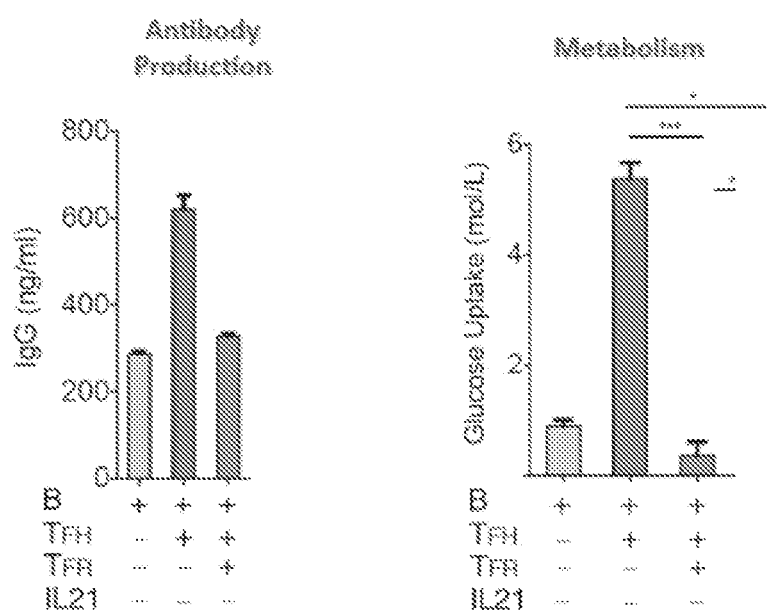

FIG. 10 shows that IL-21 can rescue TFR suppression: antibody production and metabolism.

Figure 11A:
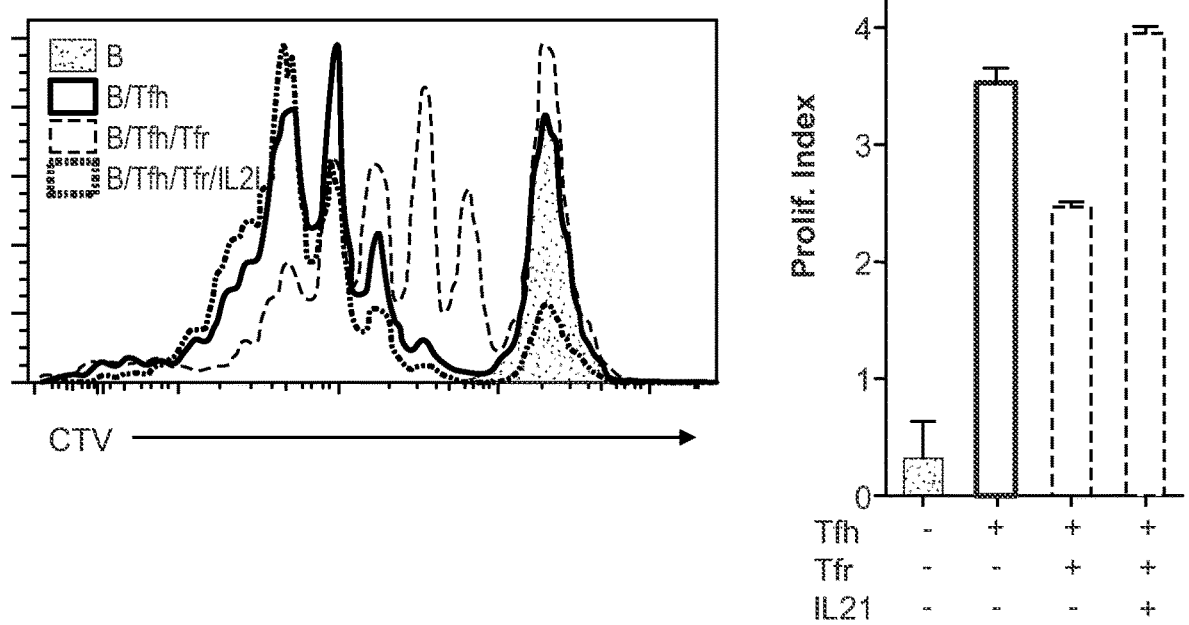

FIG. 11A-FIG. 11J show that IL-21 can overcome TFR-mediated suppression of B cell metabolism and Antibody Production. (FIG. 11A) (Left) B cell proliferation measured by Cell Trace Violet (CTV) dilution from B cells in cultures of TFH cells alone, TFH and TFR cells, or TFH and TFR cells with the addition of IL-21. (FIG. 11B) Class switch recombination measured by IgG1+GL7+ staining in B cells from cultures as in (FIG. 11A). (FIG. 11C) Antibody production measured in culture supernatants from cultures as in (FIG. 11A). IL-4/IL-21 (left) or IL-6 (right) was added to some wells. (FIG. 11D) Glut1 expression in B cells from cultures as in (FIG. 11A). (FIG. 11E) Glucose uptake was measured from culture supernatants as in (FIG. 11A). (FIG. 11F) Lactate production was measured in culture supernatants as in (FIG. 11A). (FIG. 11G) Antibody production measured in culture supernatants as in (Panel a) with the addition of 2-deoxyglucose (2DG). (FIG. 11H) Volcano plot showing all genes or B cell function genes from RNA-seq analysis from sorted B cells in Suppressed+IL-21 versus Suppressed cultures. (FIG. 11I) Collapsed ssGSEA correlation plots for Activated, Suppressed or Suppressed+IL-21 B cell RNA-seq data. (FIG. 11J) (Left) Ki67 expression in or (Right) total numbers of TFR cells from Suppressed or Suppressed+IL-21 cultures as in (FIG. 11B). *p<0.05, p<0.01, *p<0.001.

Figure 12:
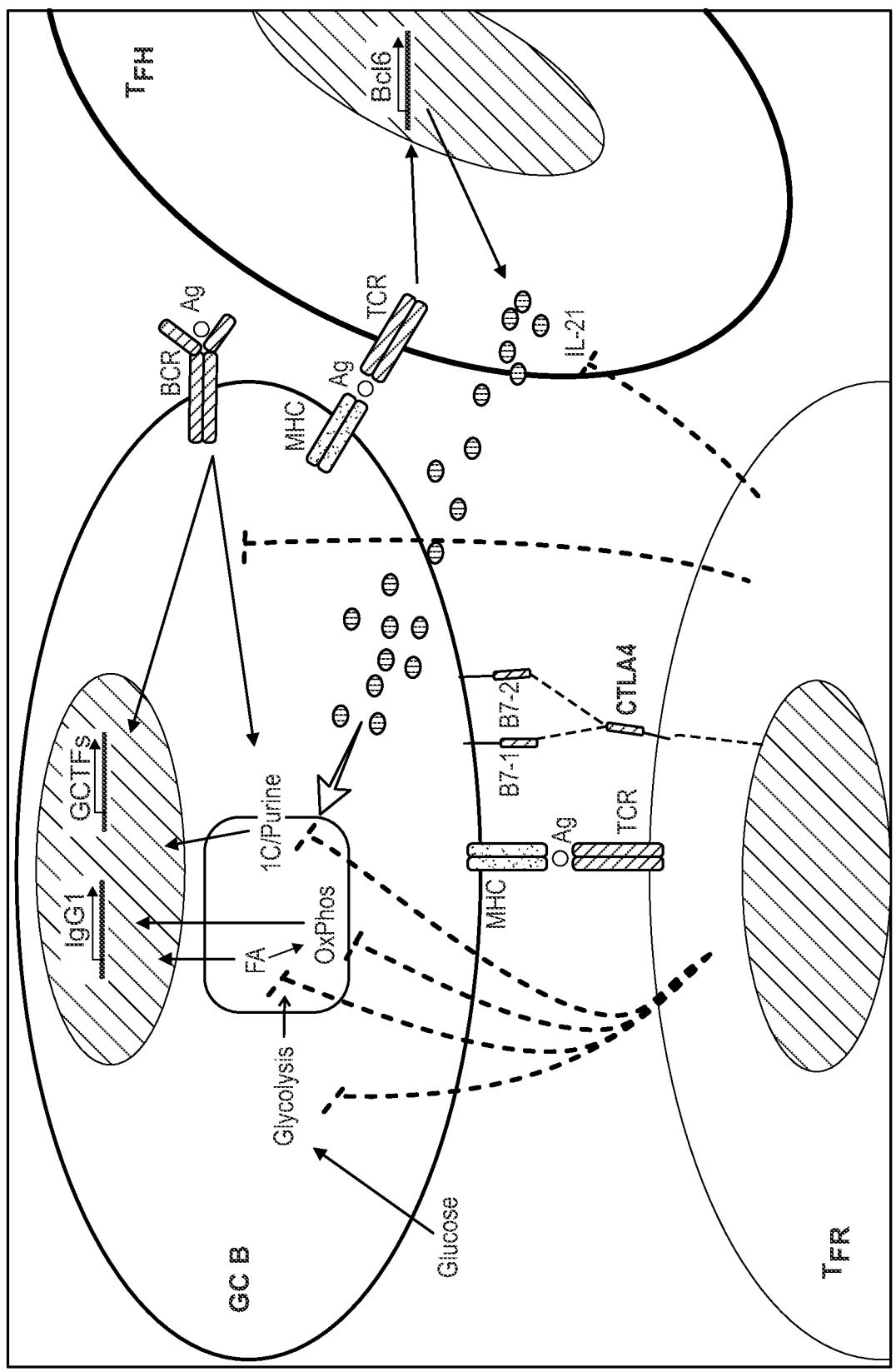

FIG. 12 shows metabolic reprogramming during $T_{FR}$ suppression.

Figure 13:
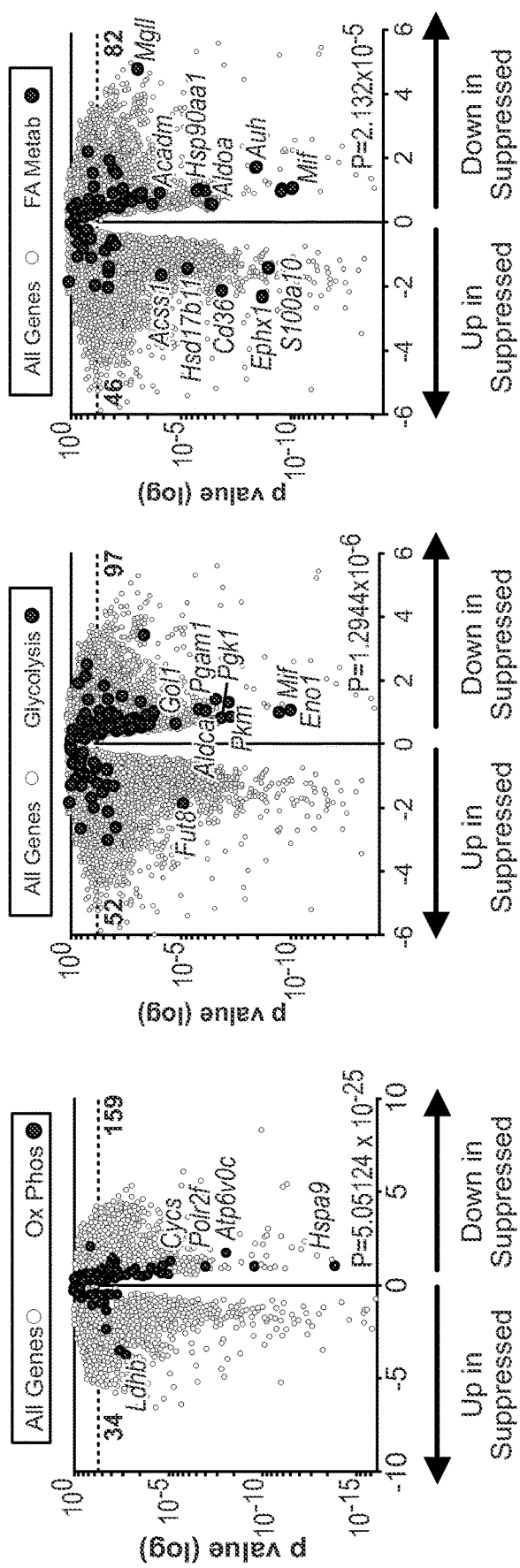

FIG. 13 shows suppressed B cells have an altered metabolic signature.

Figure 14:
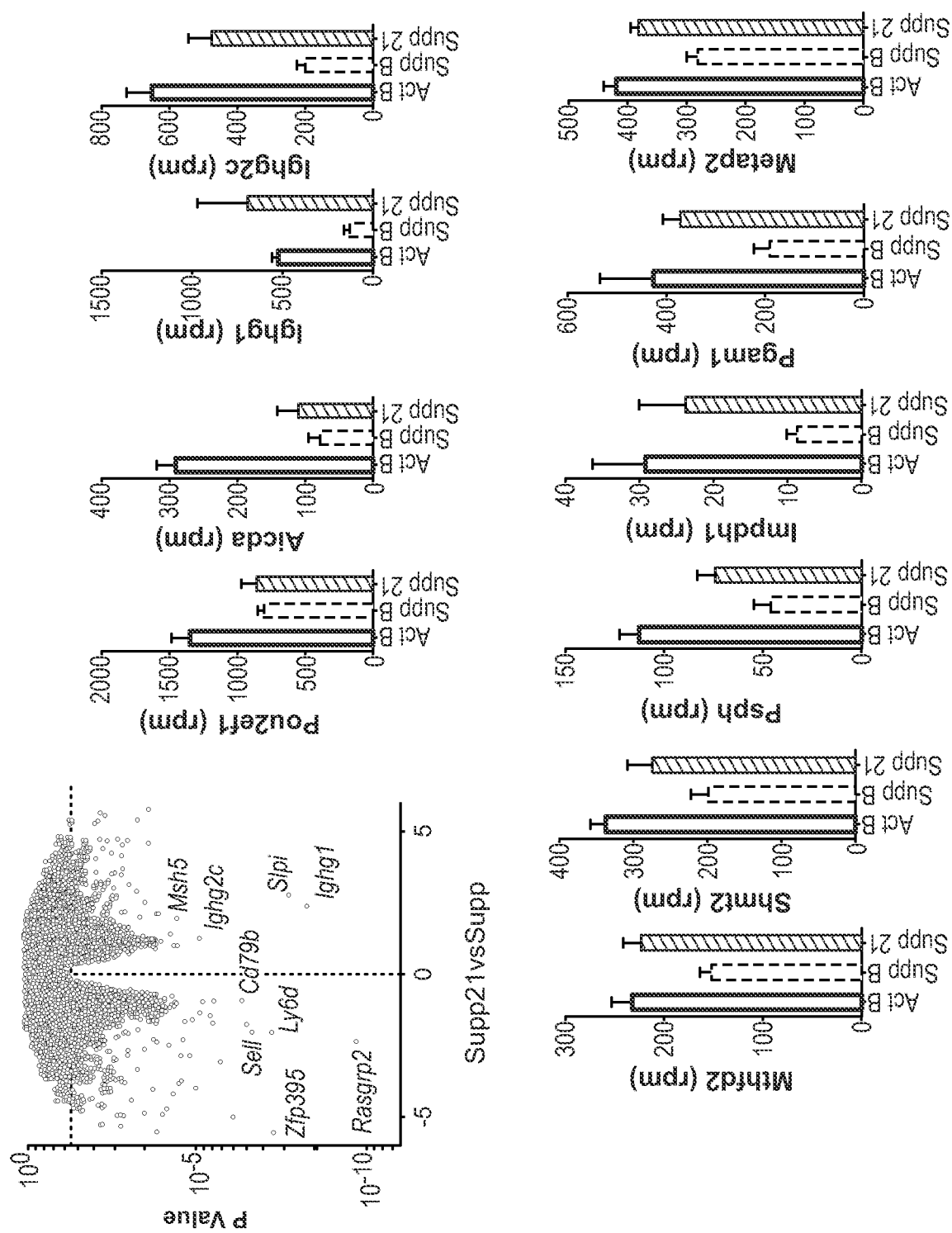

FIG. 14 shows that IL-21 can rescue $T_{FR}$ suppression: Pou2af1, Aicda, Ighg1, Ighg2c, Mthfd2, Shmt2, Psph, Impdh1, Pgam1, and Metap2 are analyzed.

Figure 15:
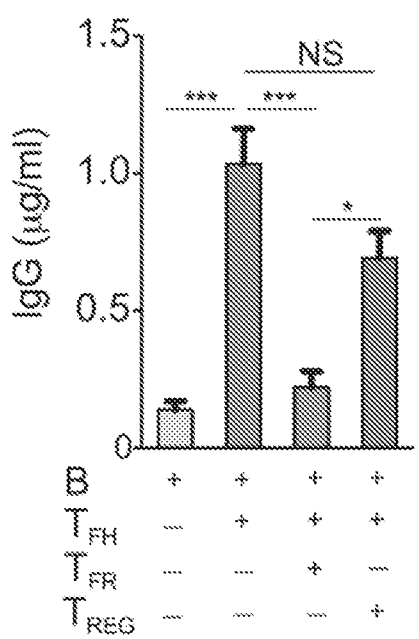

FIG. 15 shows the quantification of secreted antibody in cultures as in FIGS. 1A and in a culture including CD4+ICOS−CXCR5−Foxp3+ Treg cells (below plot).

Figure 1A:
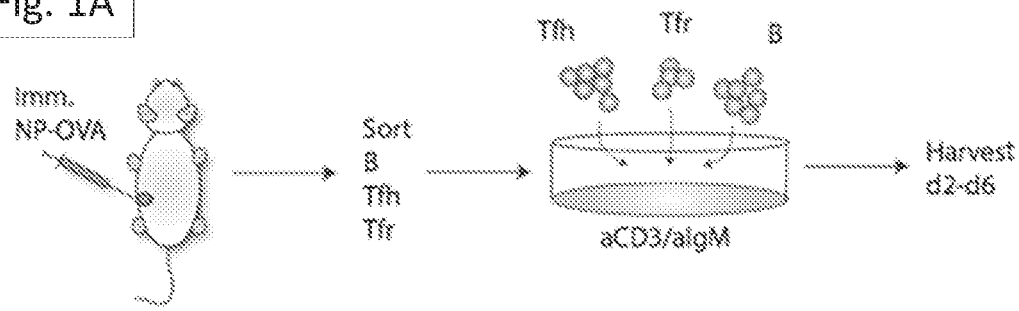
FIG. 1A-FIG. 1F show that suppressed B cells undergo early activation.
Figure 16:
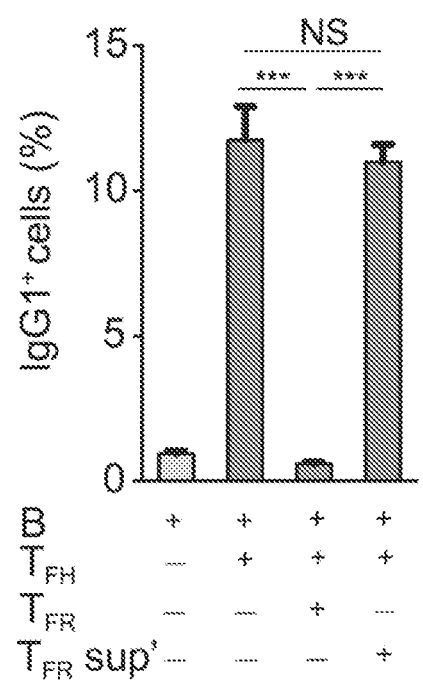

FIG. 16 shows the frequency of IgG1+B cells from cultures as in FIGS. 1A and in a culture including supernatant of suppressed cultures ($T_{FR}$ sup).

Figure 17:
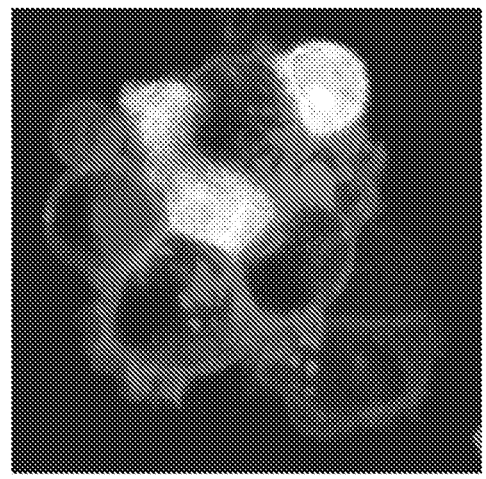

FIG. 17 shows a micrograph of a culture containing B cells, $T_{FH}$ cells and $T_{FR}$ cells, after 4 d. Scale bar, 5 μm.

Figure 18:
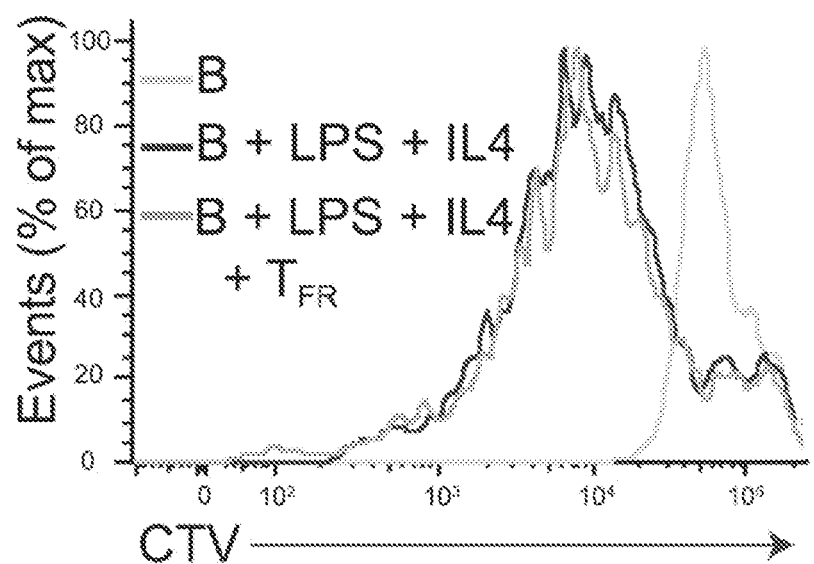

FIG. 18 shows proliferation of B cells in cultures as in FIG. 1A, incubated for 4 d with or without lipopolysaccharide (LPS) and IL-4 and $T_{FR}$ cells (key).

Figure 19:
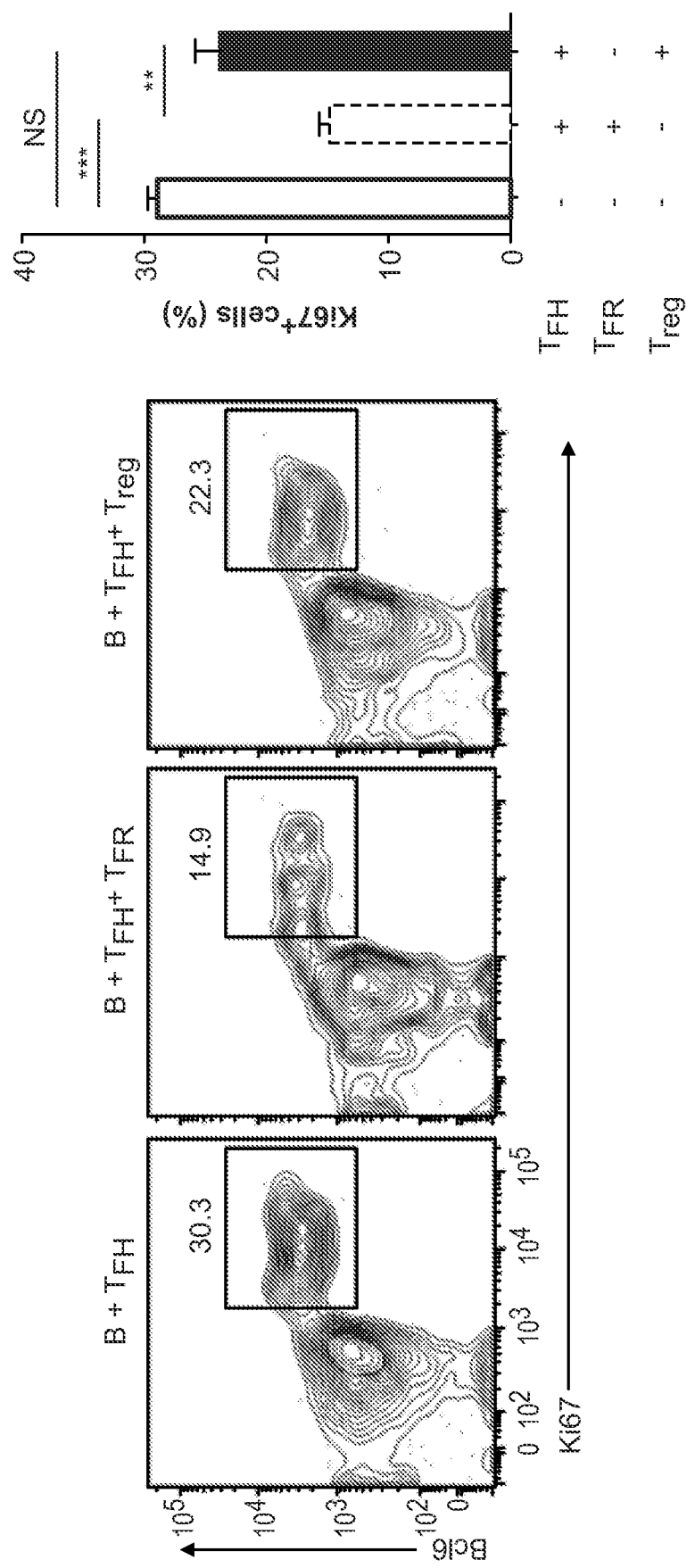

FIG. 19 shows the data from flow cytometry (left) of cultures as in FIG. 1A of cells pre-gated on TFH cells (CD4+Foxp3−CD19−IA−). Numbers adjacent to outlined areas (left) indicate percent Bcl6+Ki67+(cell-cycling) $T_{FH}$ cells.

Figure 20:
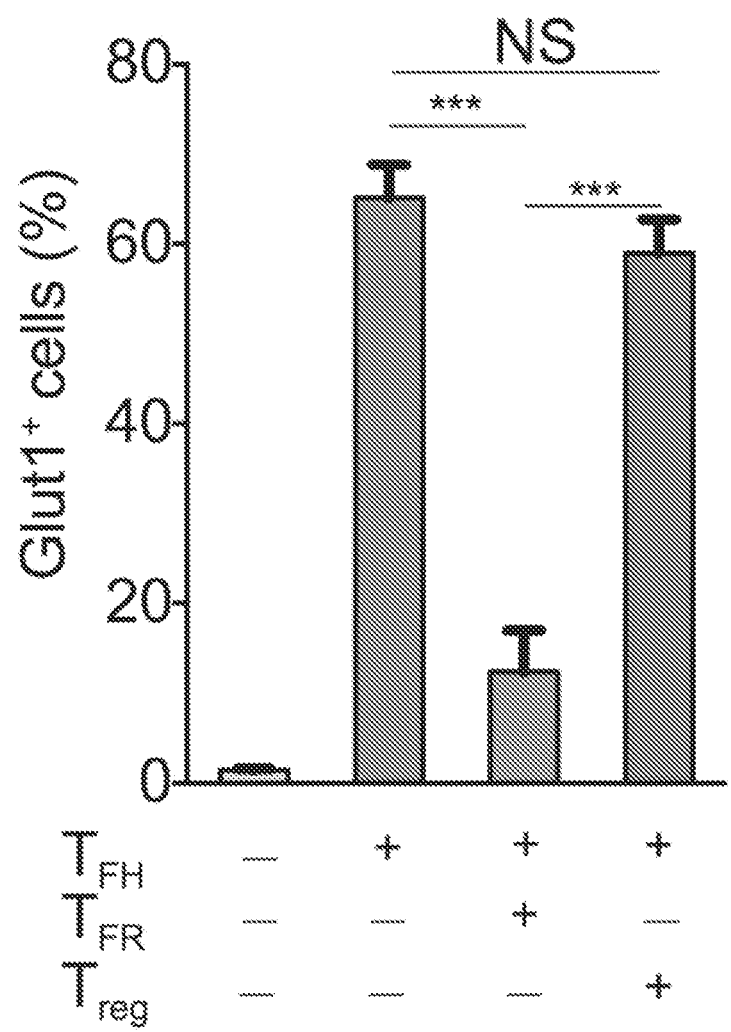

FIG. 20 shows the frequency of Glut1+ cells among B cells from activated cultures (B cells plus $T_{FH}$ cells), TFR cell-suppressed cultures (B cells plus $T_{FH}$ cells plus $T_{FR}$ cells), or Treg cell-suppressed cultures (B cells plus $T_{FH}$ cells plus Treg cells) (below plot).

Figure 21:
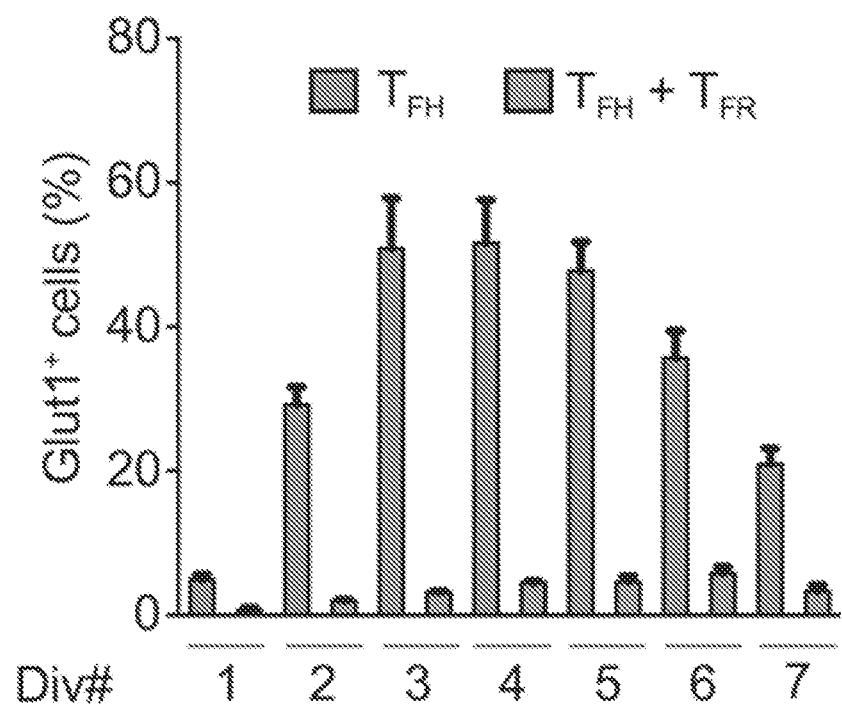

FIG. 21 shows the frequency of Glut1+ cells among B cells cultured with $T_{FH}$ cells only or with $T_{FH}$ cells plus $T_{FR}$ cells (key), gated to indicate CellTrace Violet division peaks (horizontal axis).

Figure 22:
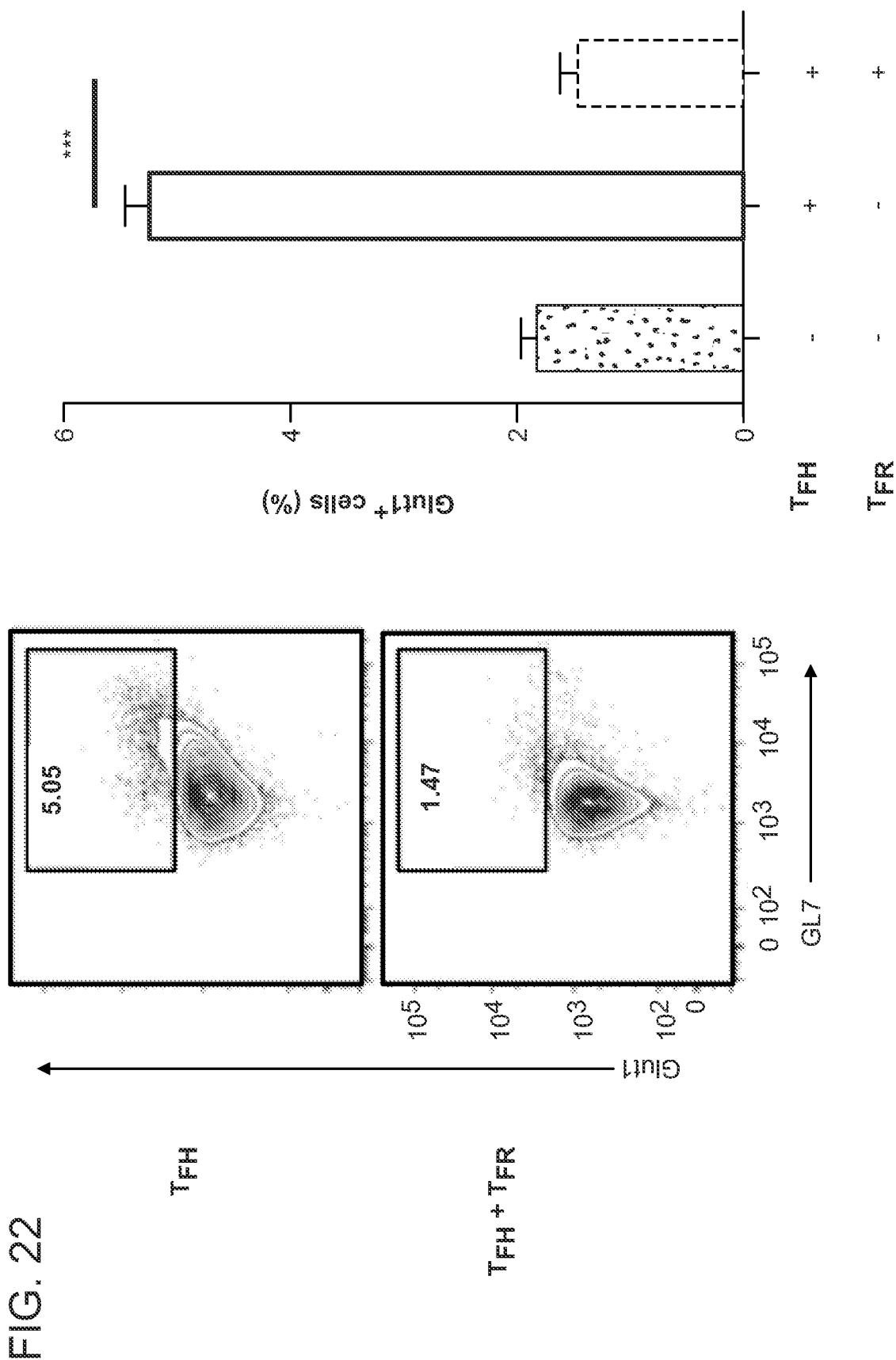

FIG. 22 shows the flow cytometry of B cells added to cultures of $T_{FH}$ cells or $T_{FH}$ cells plus $T_{FR}$ cells (left margin) at day 3 and assessed 20 h later (left), and frequency of Glut1+ cells among those B cells (right). Numbers in outlined areas (left) indicate percent Glut1+B cells.

Figure 23:
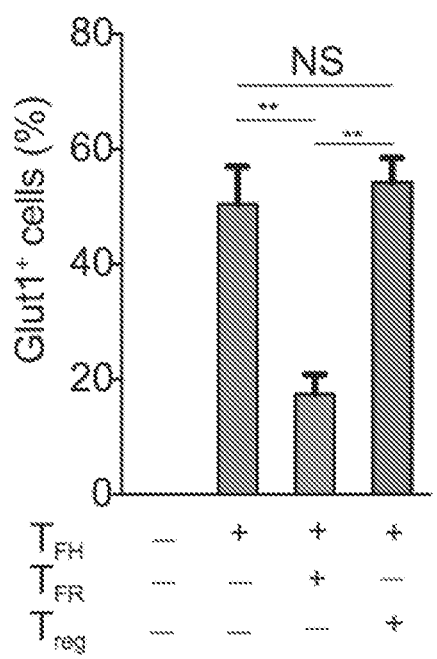

FIG. 23 shows the frequency of Glut1+ cells among $T_{FH}$ cells in cultures as in FIG. 20.

Figure 1B:
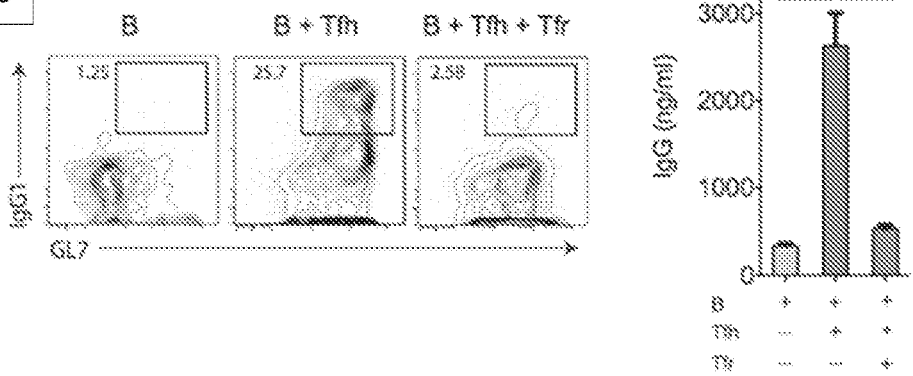
Figure 24:
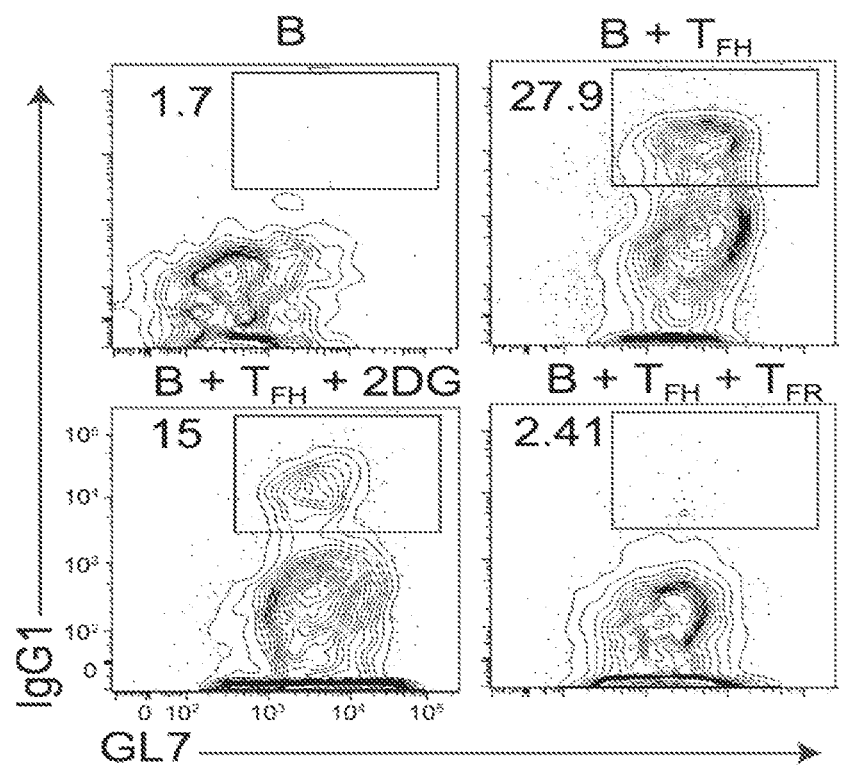

FIG. 24 shows the flow cytometry of cultures as in FIG. 20 in the presence (+2DG) or absence of 2DG (numbers in plots, as in FIG. 1B)

Figure 25:
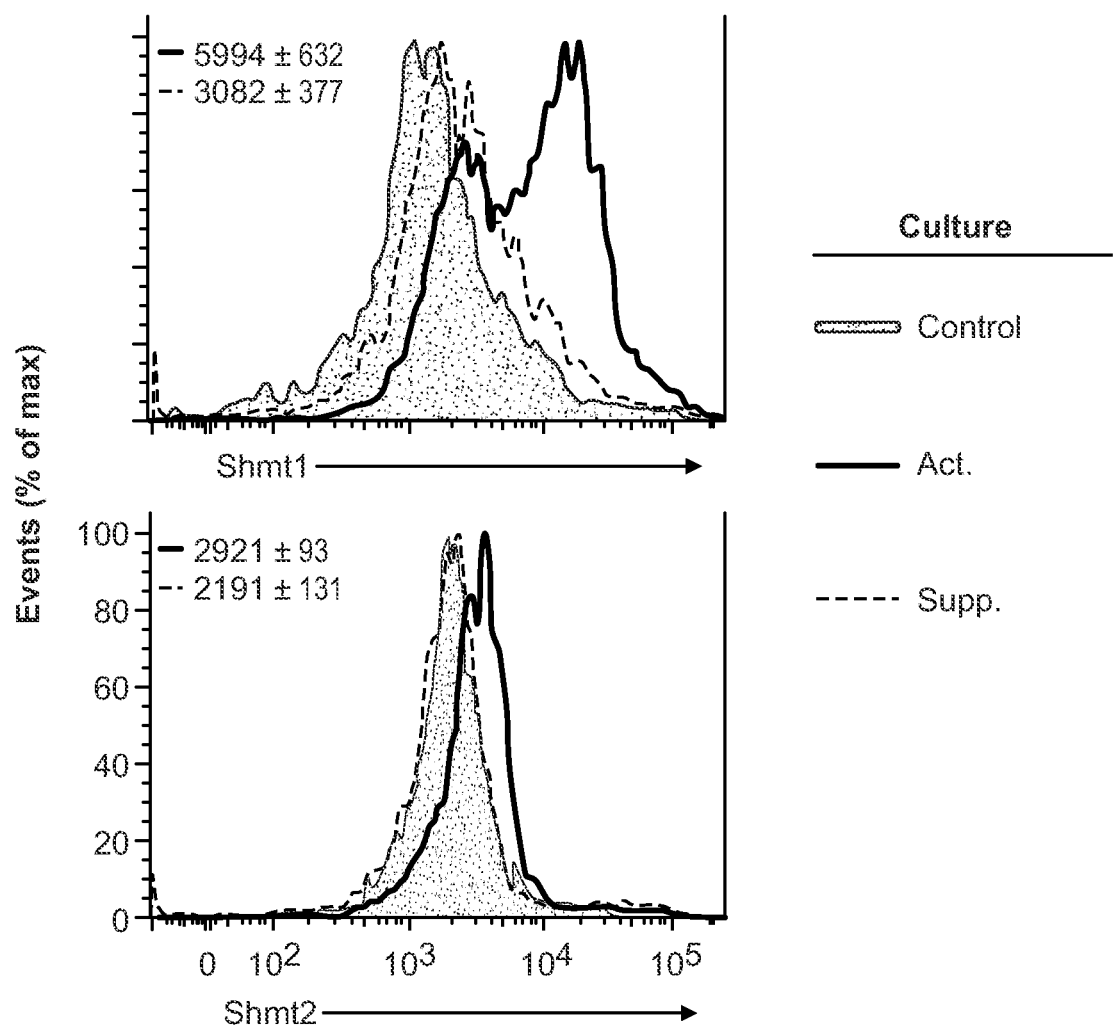

FIG. 25 shows expression of Shmt1 (top) and Shmt2 (bottom) in B cells added to cell-free cultures (Control) or to activated or suppressed cultures (key) at day 3 and assessed 20 h later.

Figure 8A:
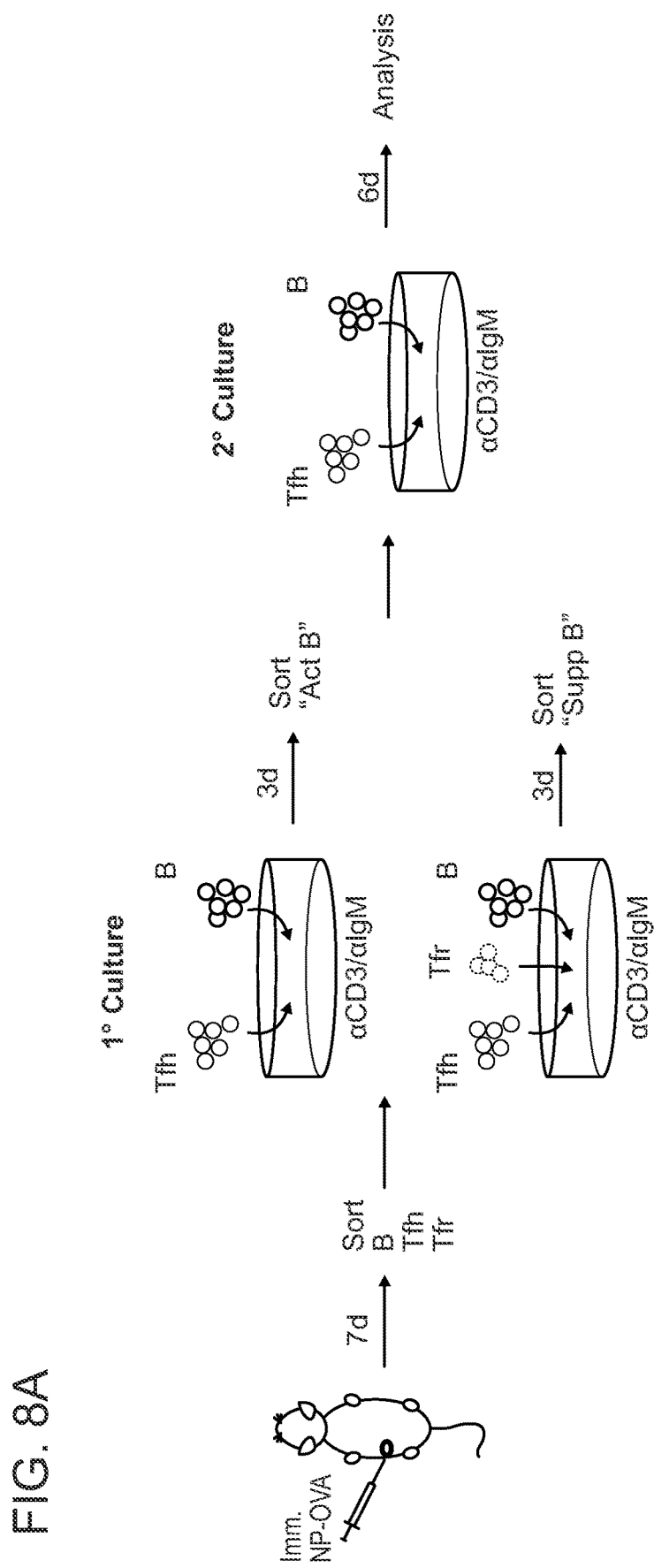
FIG. 8A-FIG. 8G show TFR suppression results in sustained inhibition and epigenetic changes in B cells.
Figure 26:
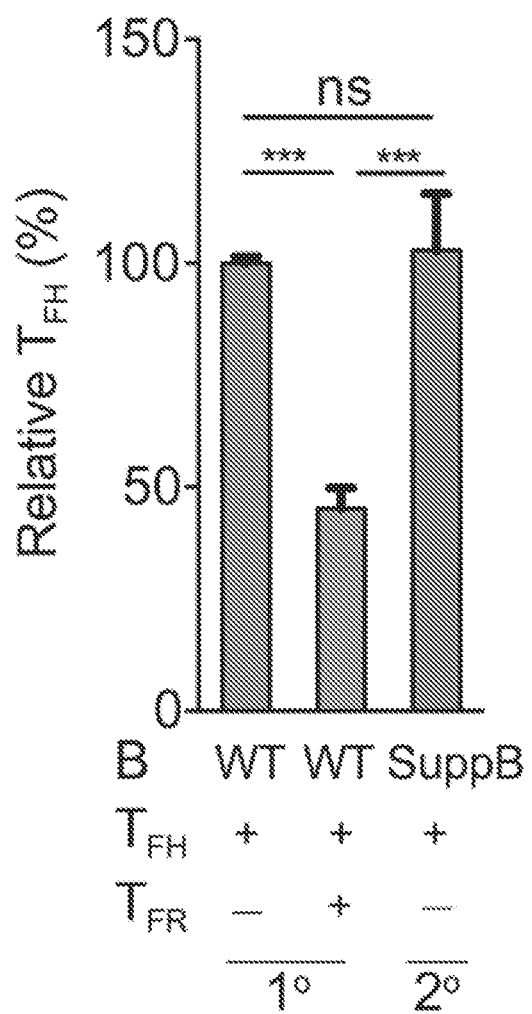

FIG. 26 shows the frequency of $T_{FH}$ cells in cultures as in FIG. 8A.

Figure 27:
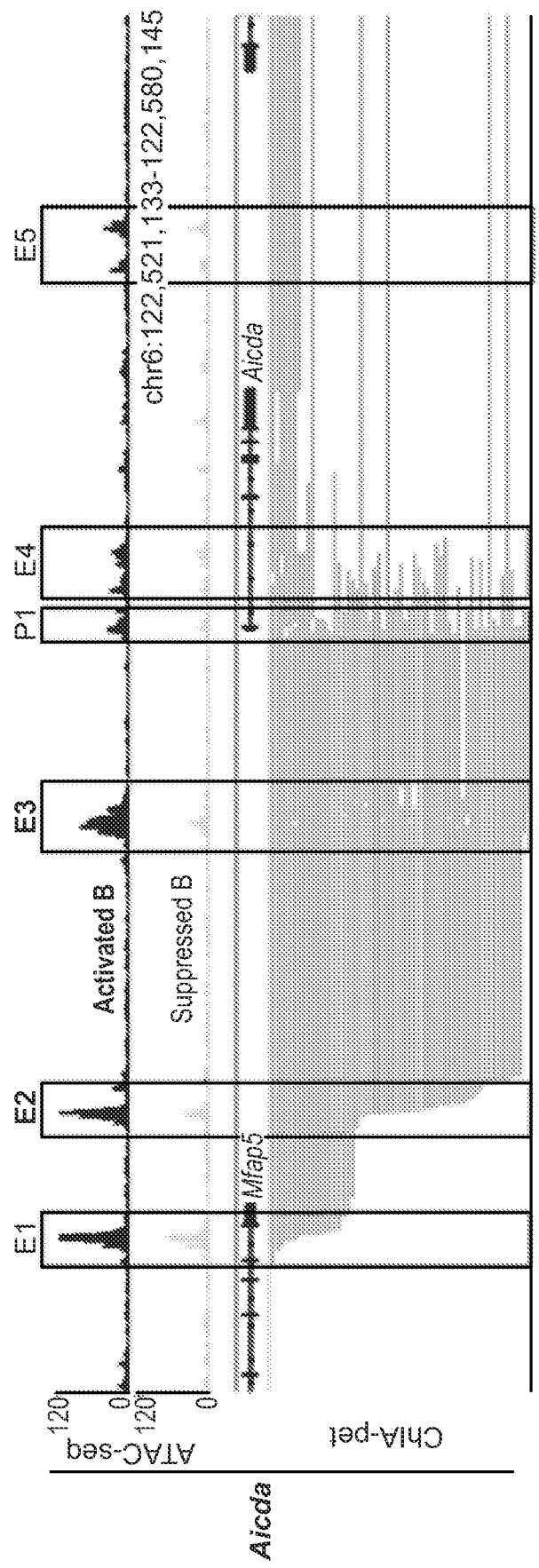
Figure 28:
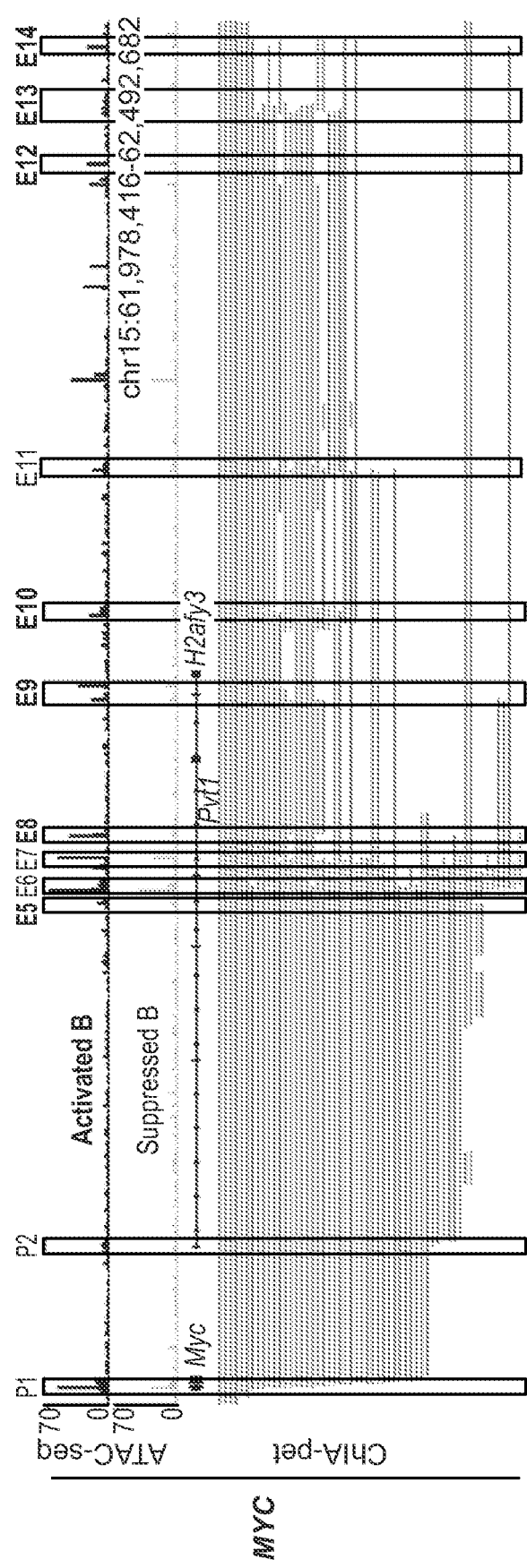
Figure 29:
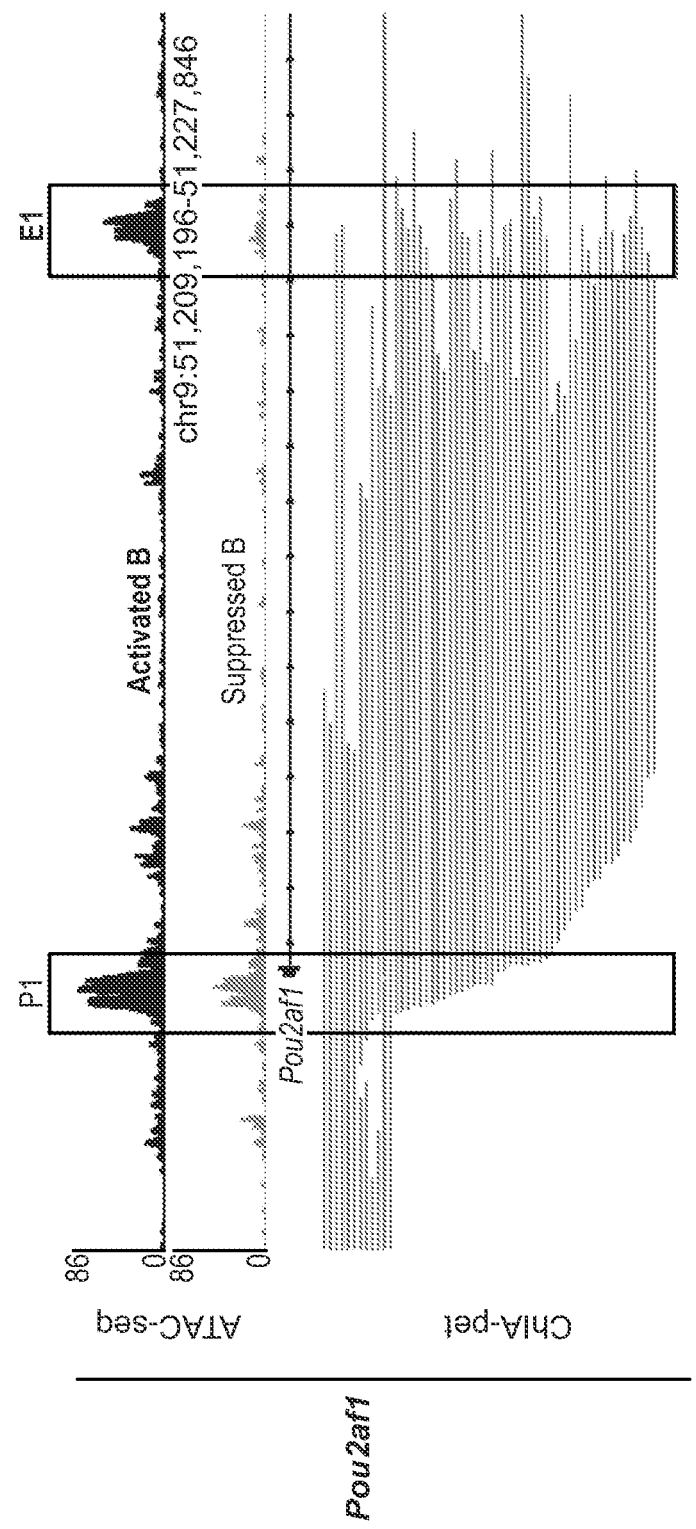

FIG. 27-FIG. 29 ATAC-seq peaks and ChIA-pet annotated B cell regulome gene tracks for Aicda (FIG. 27), Myc (FIG. 28) and Pou2af1 (FIG. 29); boxes indicate significant down-regulation (P<0.05)

Figure 30:
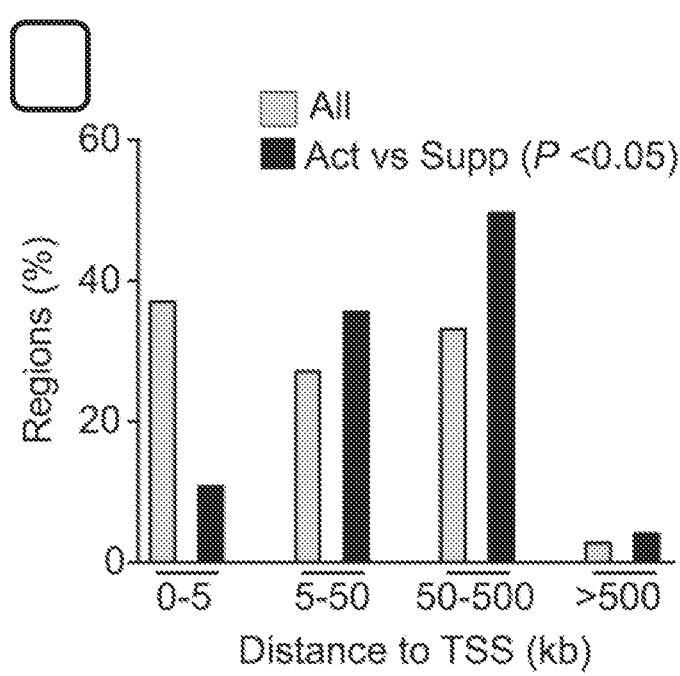

FIG. 30 shows the distance of ATAC-seq peaks from TSSs for all peaks or peaks less accessible in suppressed B cells.

Figure 31:
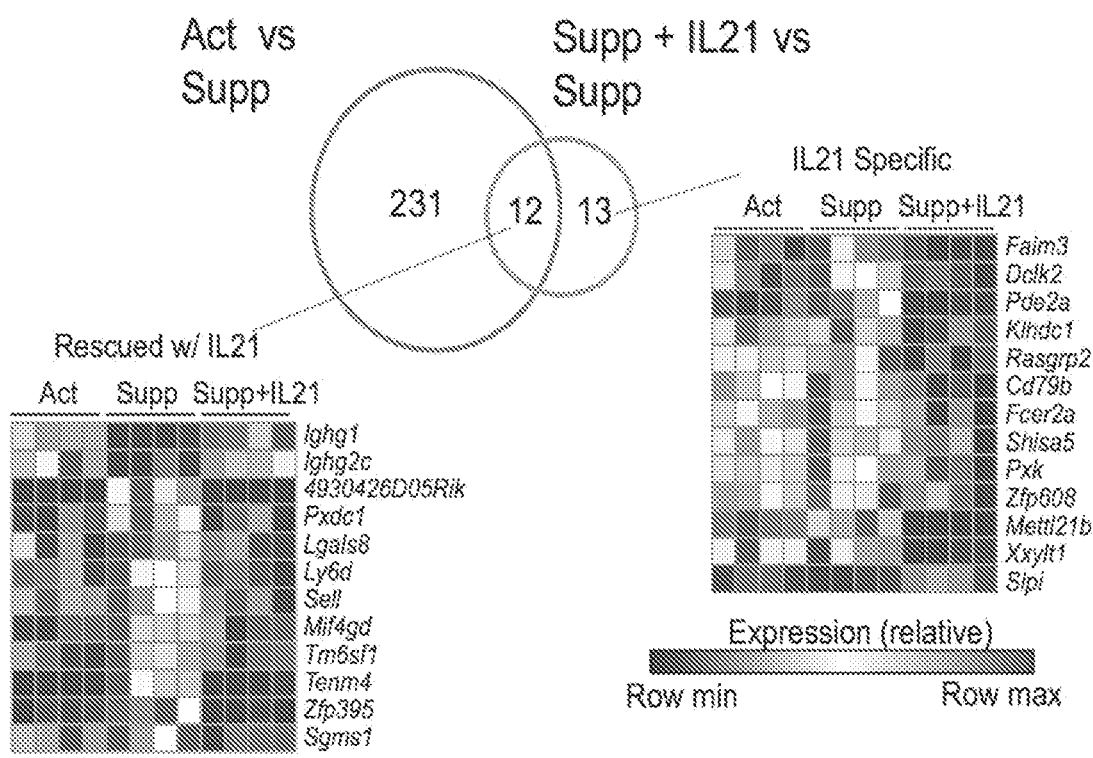

FIG. 31 shows all genes expressed differentially (FDR-adjusted P value, <0.05) in activated B cells versus suppressed B cells (left) or in suppressed B cells rescued with IL-21 versus suppressed B cells (right).

Figure 32:
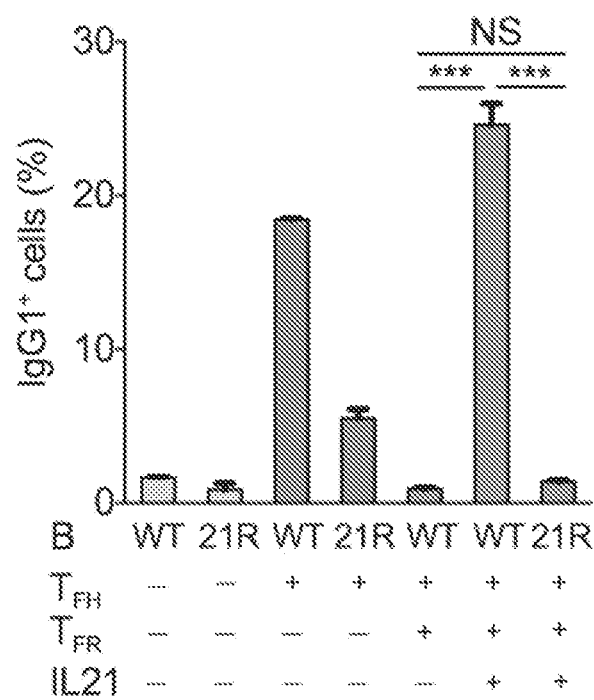

FIG. 32 shows the frequency of IgG1+GL7+B cells in cultures (pre-gated as CD19+IA+CD4−) of wild-type B cells (WT) or Il21r−/−B cells (21R) cultured with $T_{FH}$ cells alone, $T_{FH}$ and $T_{FR}$ cells, or $T_{FH}$ cells and $T_{FR}$ cells plus IL-21 (below plot).

Figure 33:
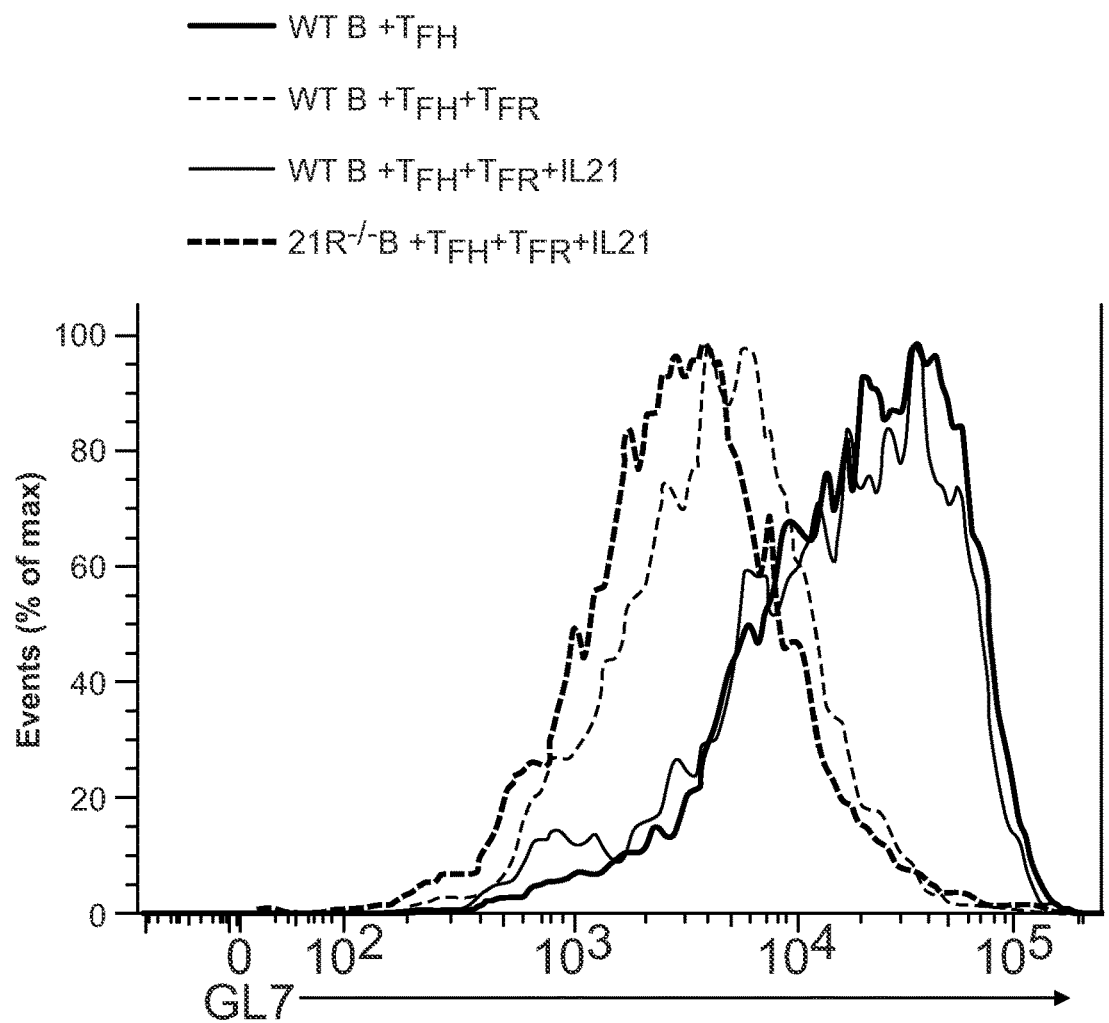

FIG. 33 shows GL7 expression in B cells from cultures as in FIG. 32.

Figure 34:
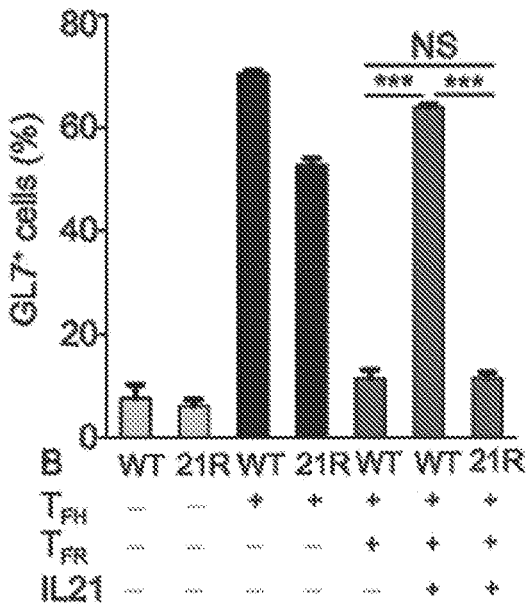

FIG. 34 shows the frequency of GL7+ cells among B cells from cultures as in FIG. 32.

Figure 11B:
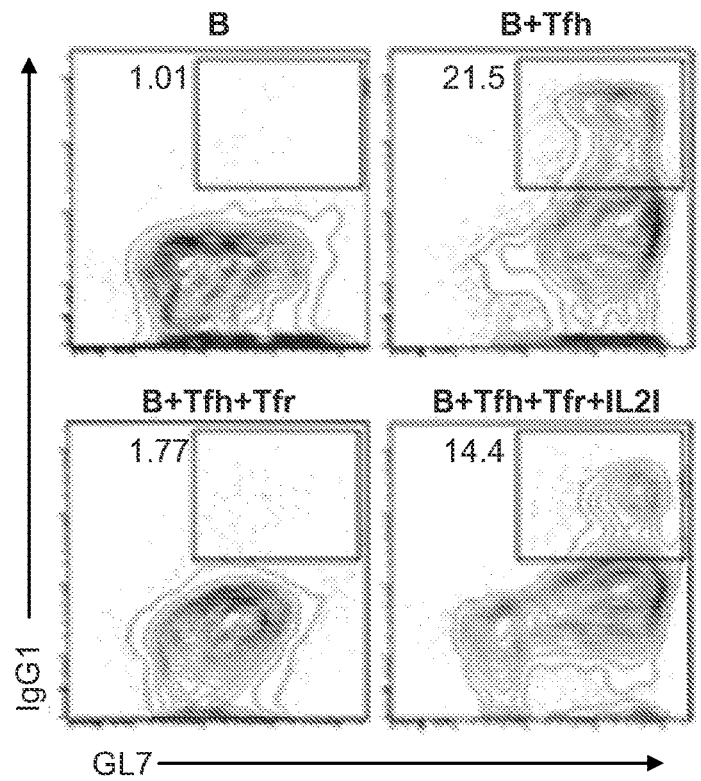
Figure 11C:
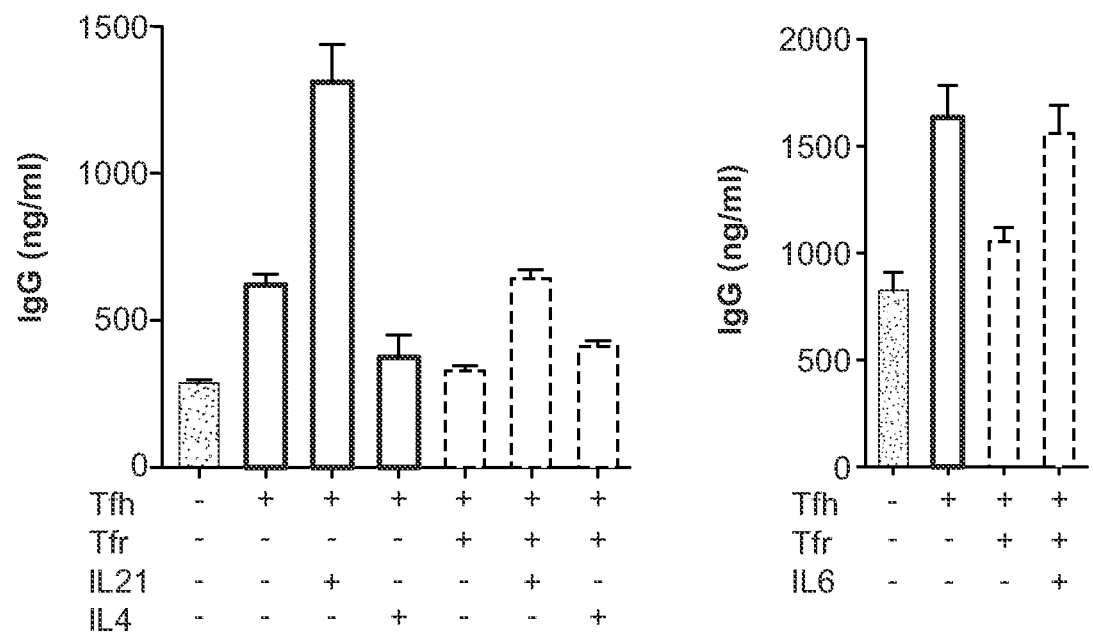
Figure 11D:
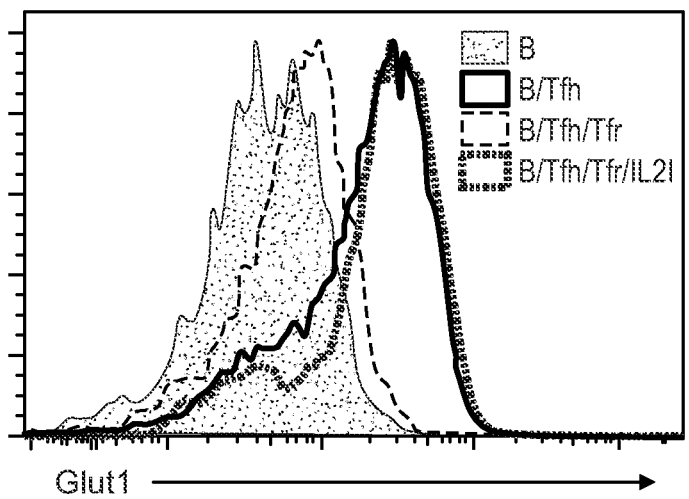
Figure 11E:
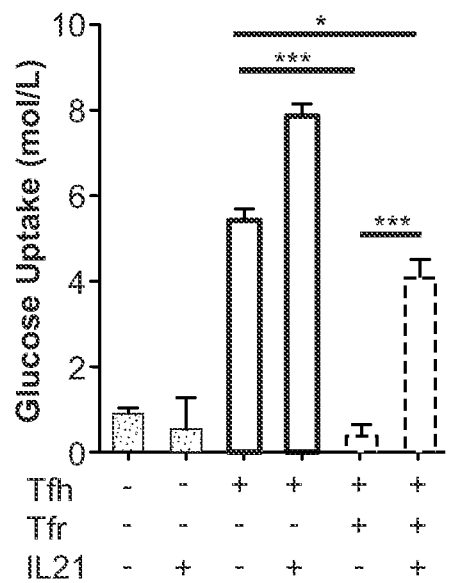
Figure 11F:
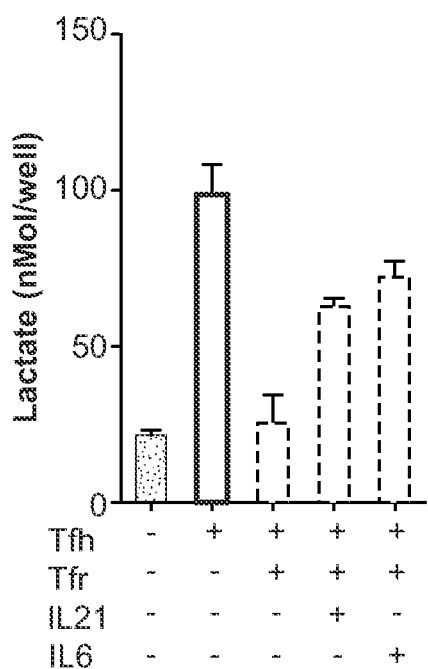
Figure 11G:
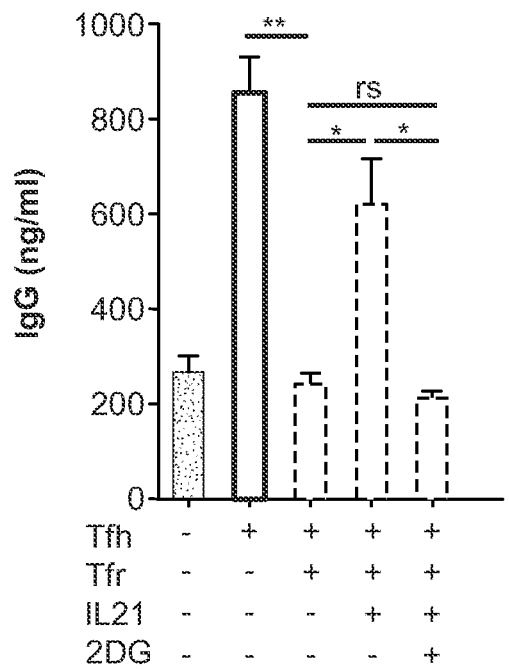
Figure 11H:
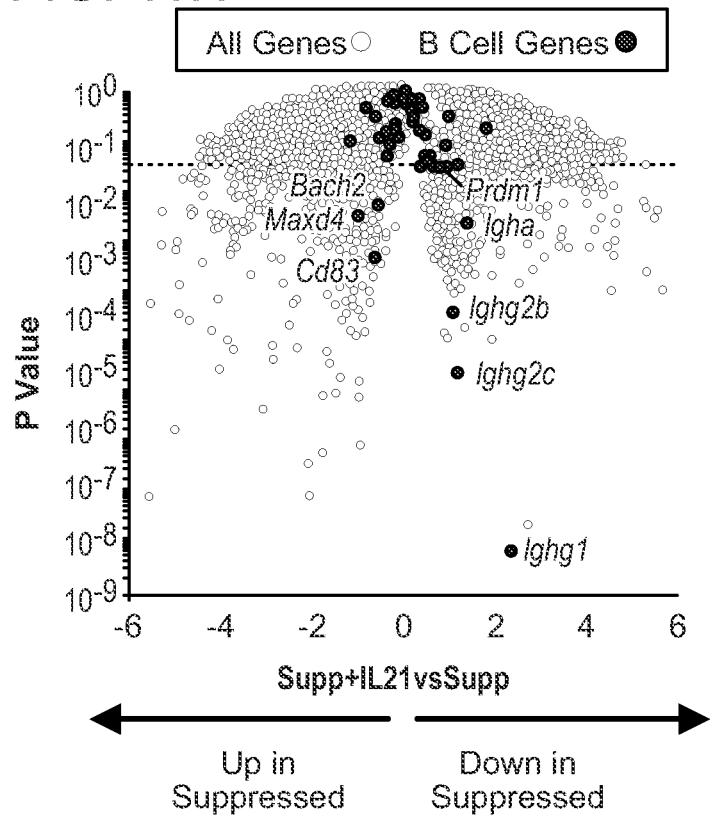
Figure 11I:
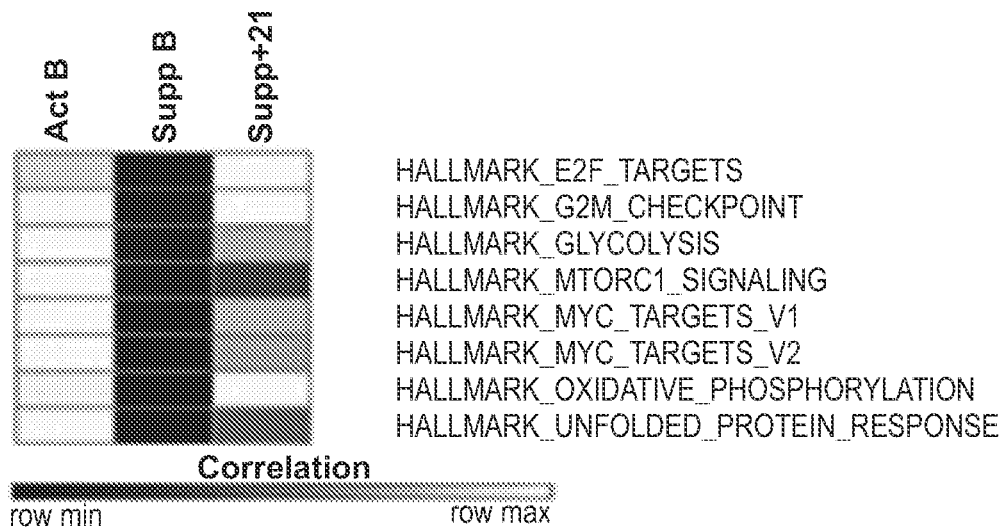
Figure 11J:
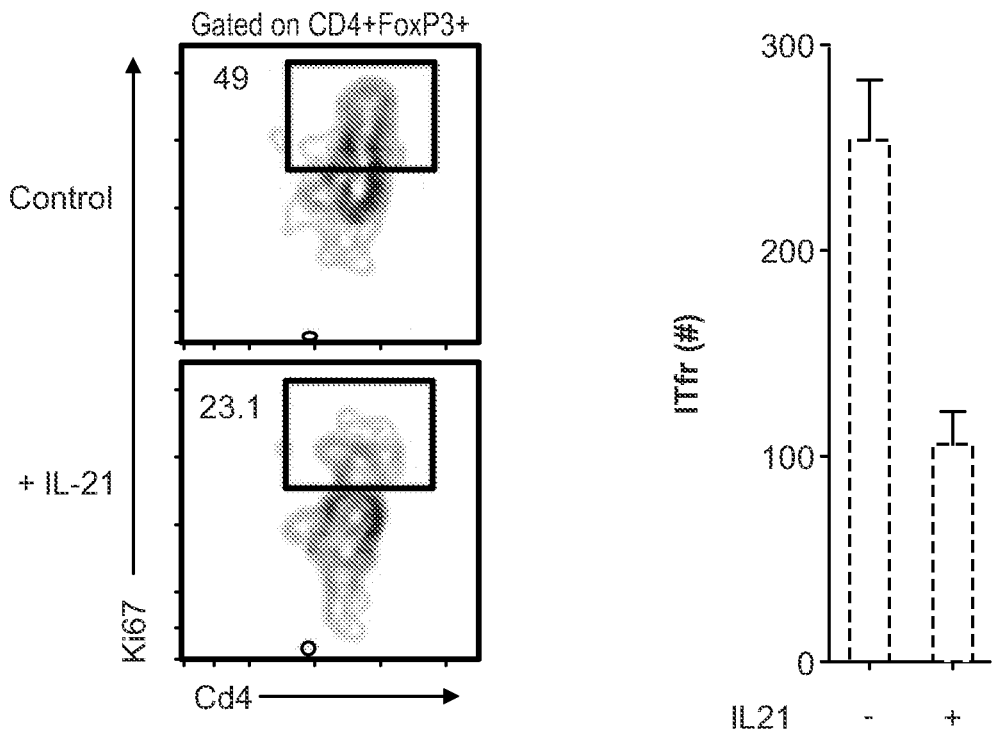
Figure 35:
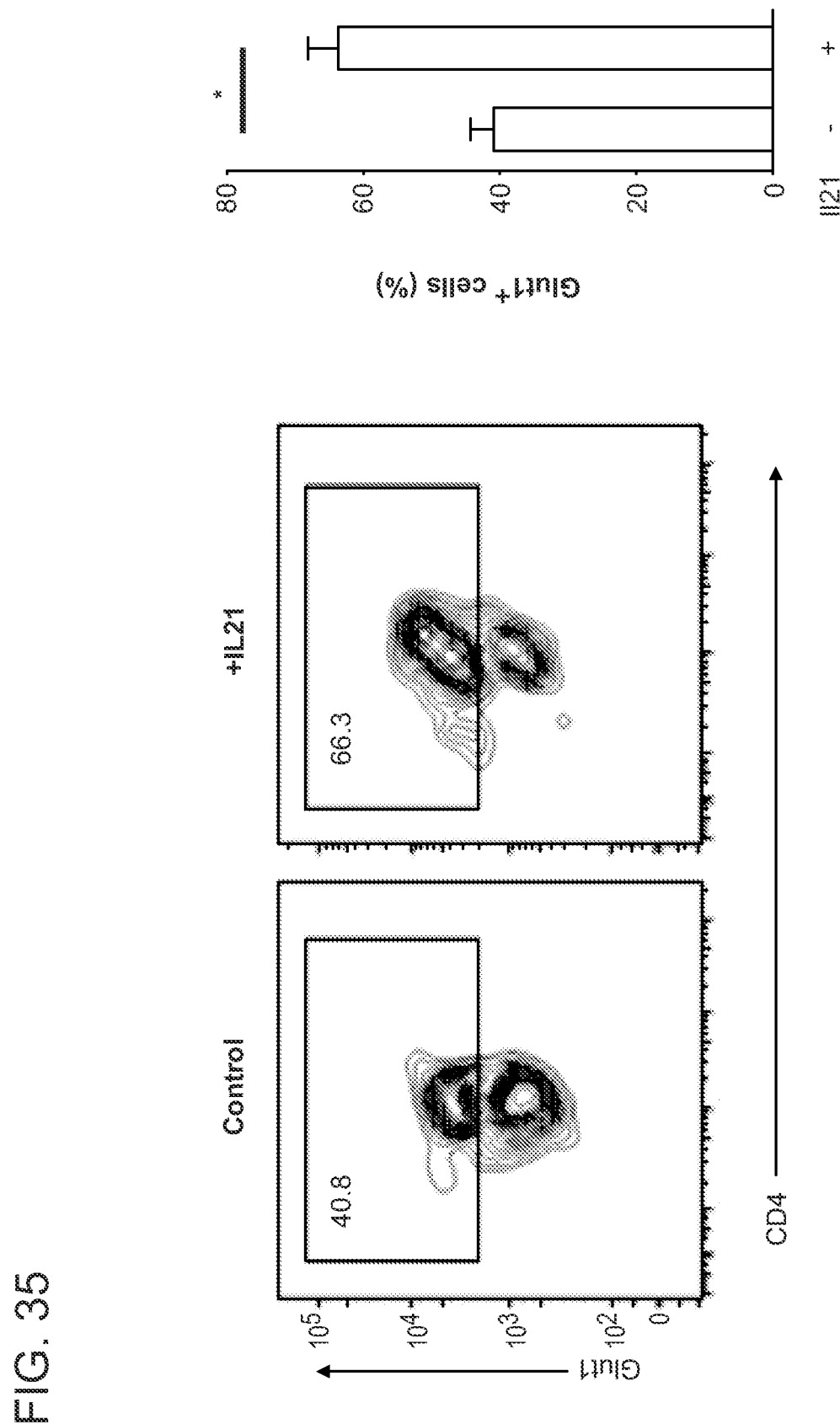

FIG. 35 shows the Glut1 expression in $T_{FR}$ cells from cultures as in FIG. 11J (left), and frequency of Glut+ $T_{FR}$ cells from cultures (right).

FIG. 36A-FIG. 36C show the Sorting gates for $T_{FH}$ cells, $T_{FR}$ cells and B cells. FIG. 36A shows a schematic of Suppression assay. FoxP3-GFP reporter mice were immunized with NP-OVA and 7 days later dLN were harvested and CD19+ B cells and CD4+CXCR5+ICOS+FoxP3−CD19− $T_{FH}$ cells were cultured with or without CD4+CXCR5+ICOS+FoxP3+CD19− $T_{FR}$ cells in the presence of anti-CD3/IgM. FIG. 36B shows the sort strategy for sorting $T_{FH}$ and $T_{FR}$ cells. FIG. 36C shows the class switch to IgG1 in suppression assays in which B and $T_{FH}$ cells were cultured with or without $T_{FR}$ cells along with either anti-CD3/IgM or NP-OVA.

Figure 37A:
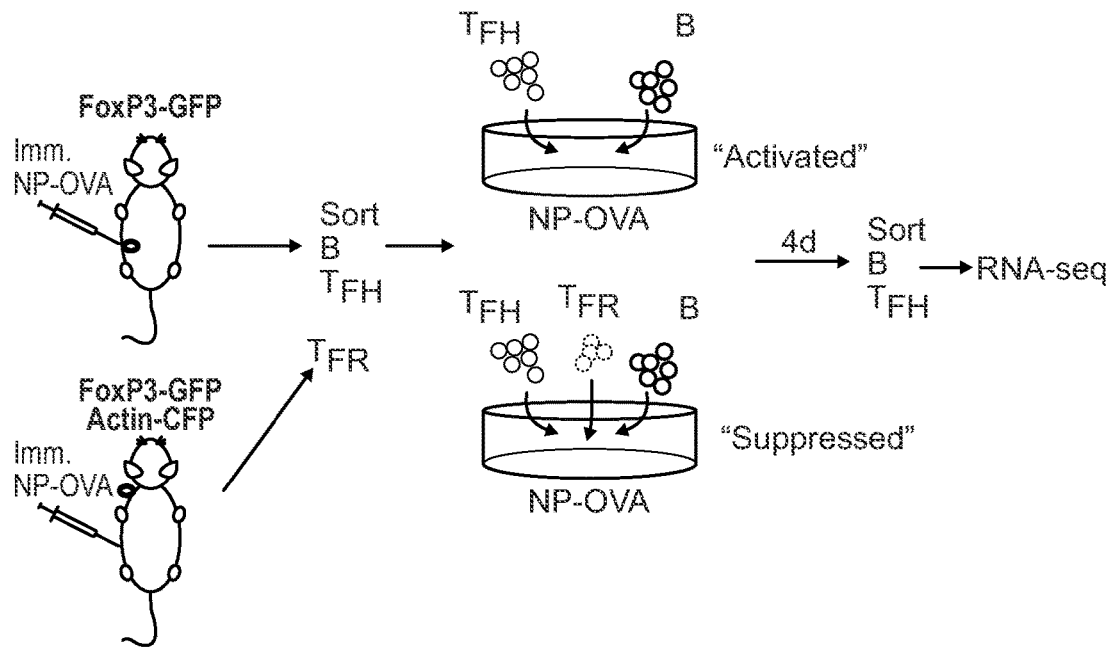
Figure 37B:
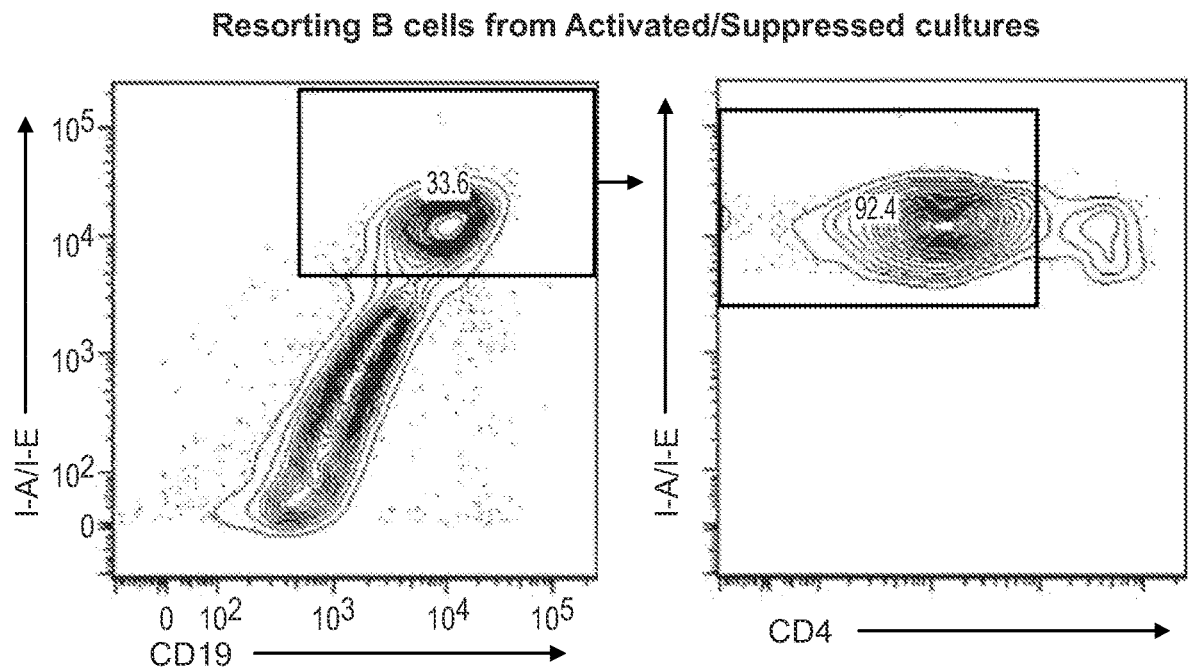
Figure 37C:
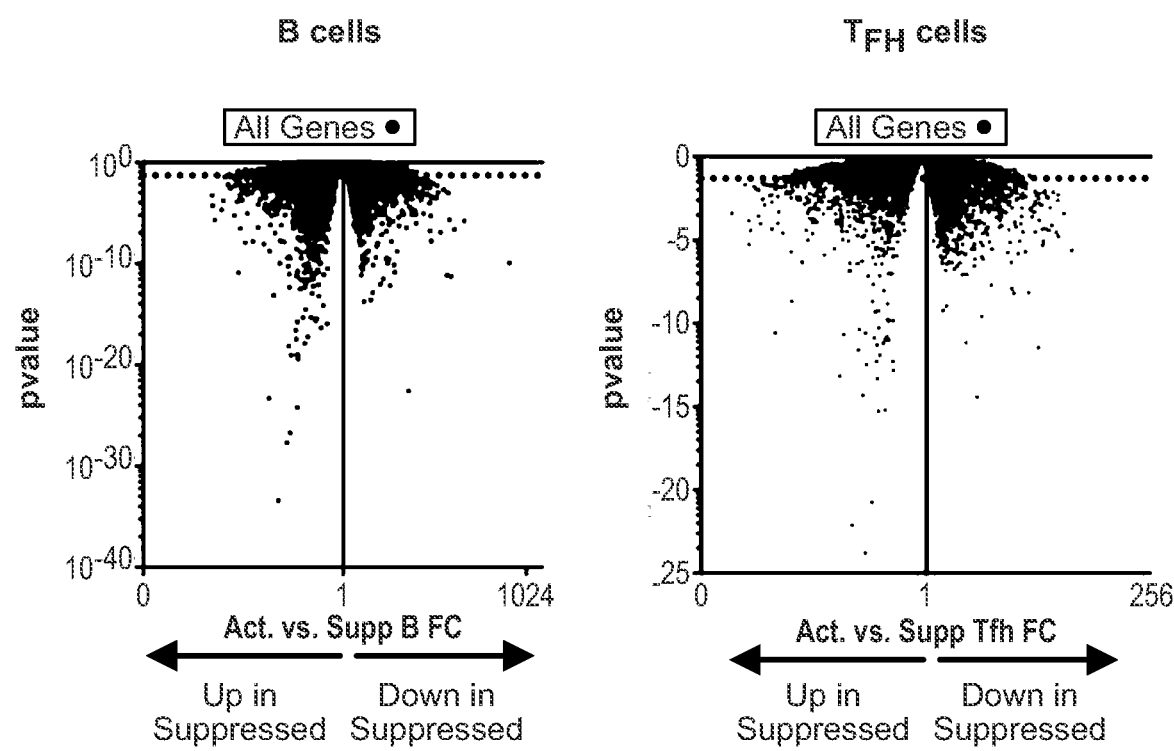
Figure 37D:
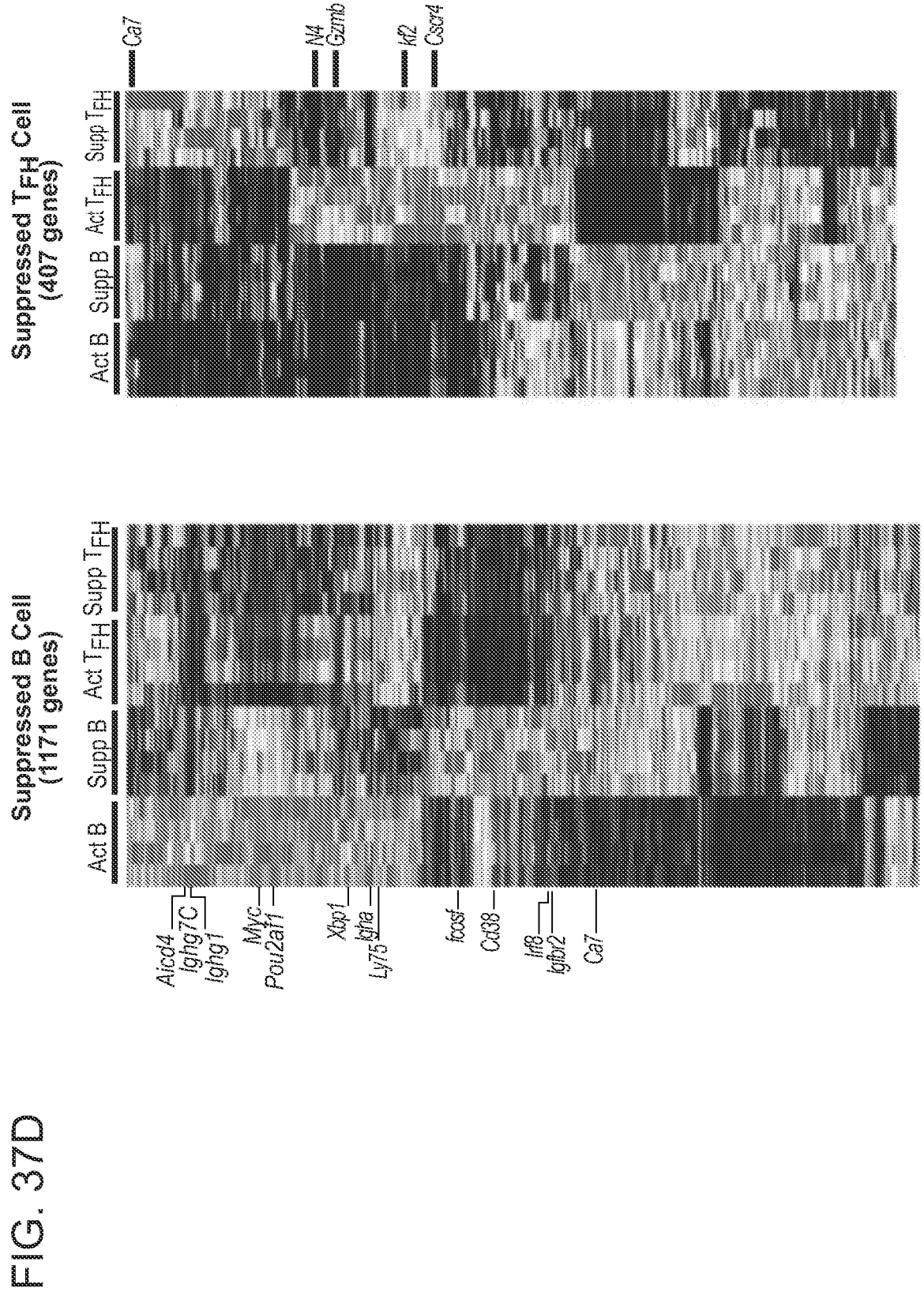
Figure 37E:
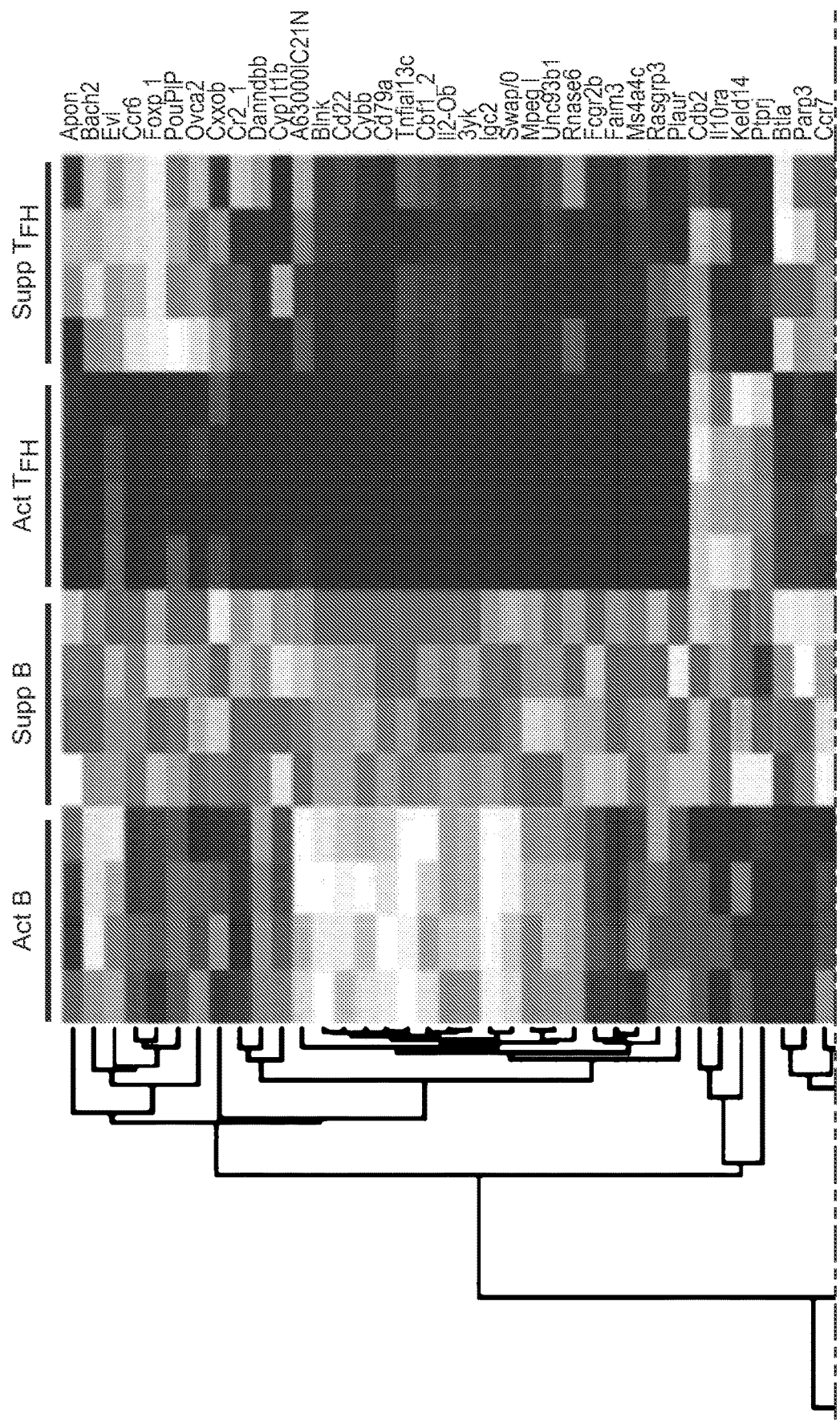
Figure 37E:
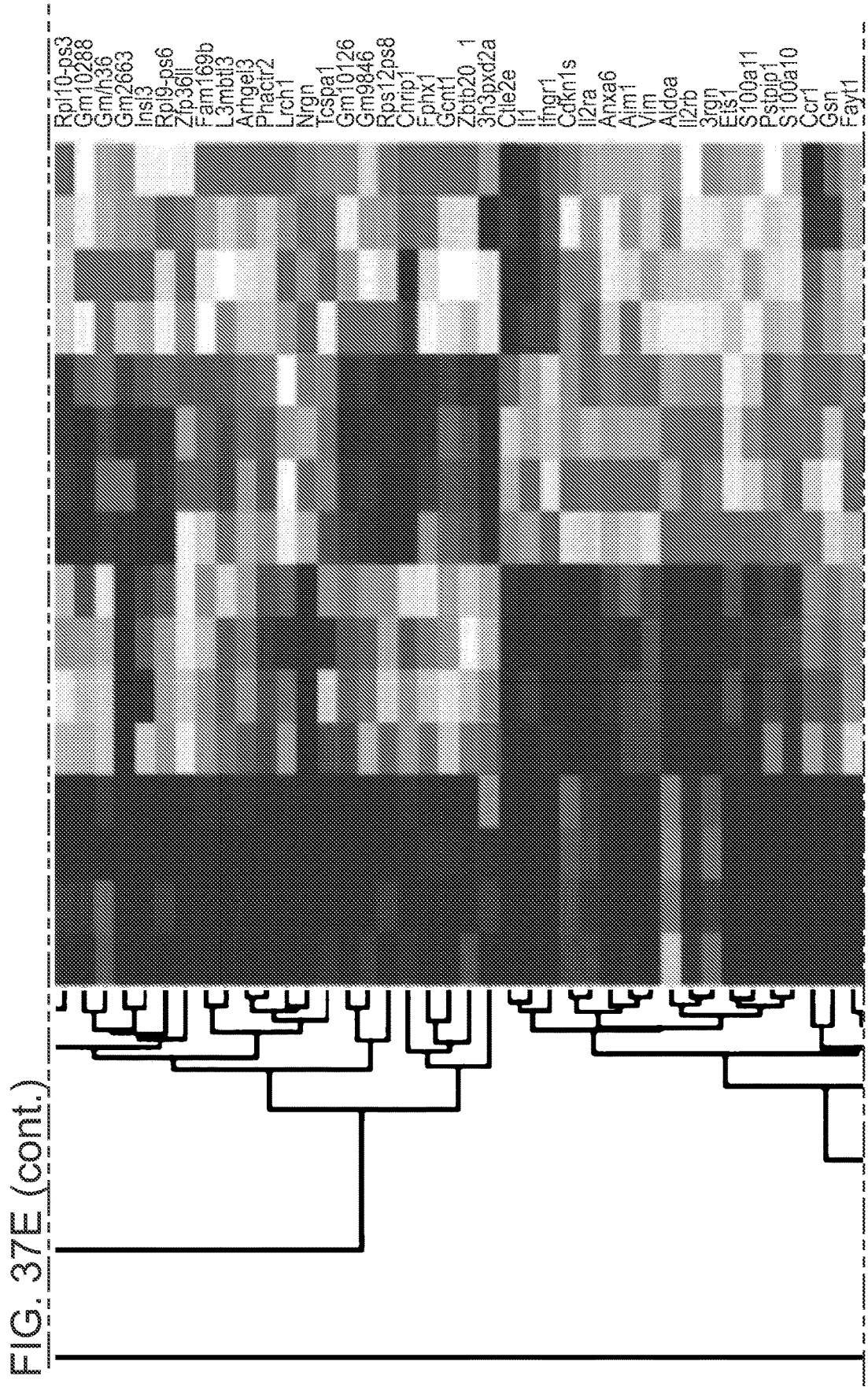
Figure 37E:
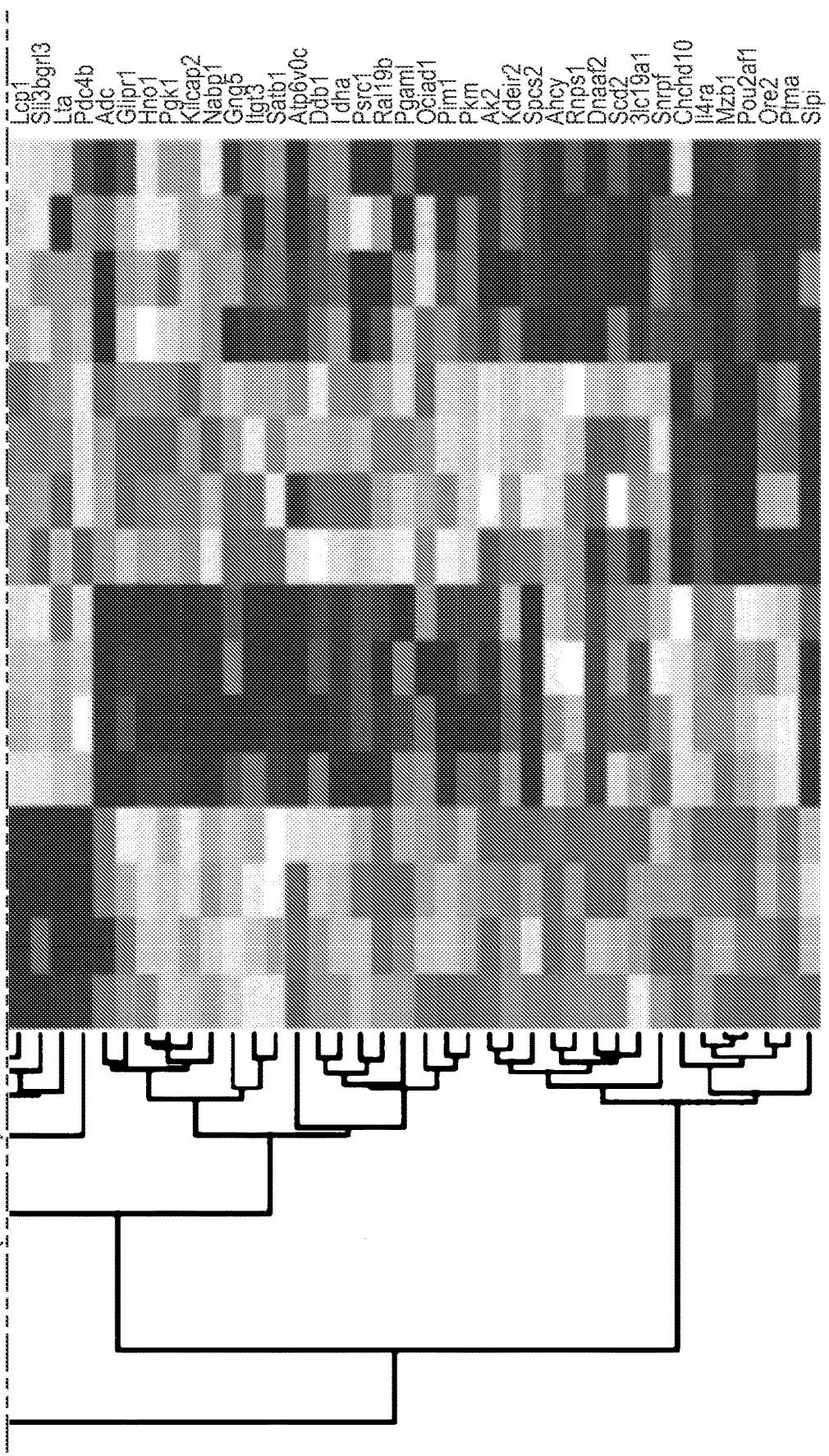

FIG. 37A-FIG. 37E show additional characterization of activated and suppressed B cells based on RNA-seq analysis. FIG. 37A shows a schematic of experiment. B and $T_{FH}$ cells, sorted from NP-OVA immunized FoxP3$^{GFP}$ mice, were cultured alone ("Activated") or with $T_{FR}$ cells ("Suppressed") sorted from FoxP3$^{GFP}$ Actin$^{CFP}$ mice, in the presence of NP-OVA. After 4 days CD19+IA+CD4−CFP− B and CD4+CD19−IA−CFP− $T_{FH}$ cells were sorted and processed for RNA-seq analysis. FIG. 37B shows the sorting gates for B cells. FIG. 75C shows volcano plots showing genes in B and $T_{FH}$ cells in the context of activated or suppressed cultures. FIG. 37D shows the heat map of genes differentially expressed (FDR corrected p<0.05) in B and $T_{FH}$ cells from activated versus suppressed cultures. FIG. 37E shows genes differentially expressed in both T and B cells in activated versus suppressed cultures.

Figure 38:
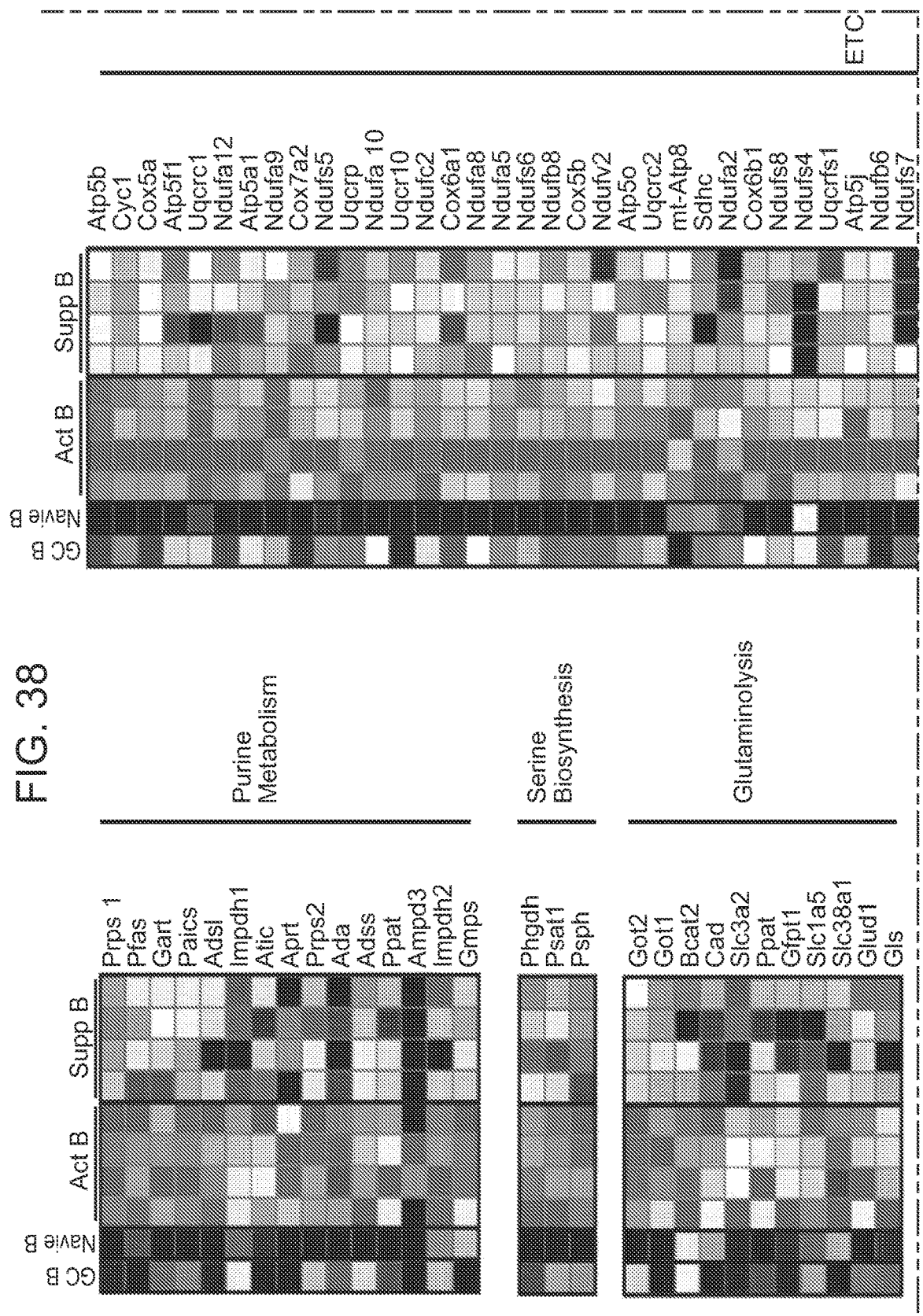
Figure 38:
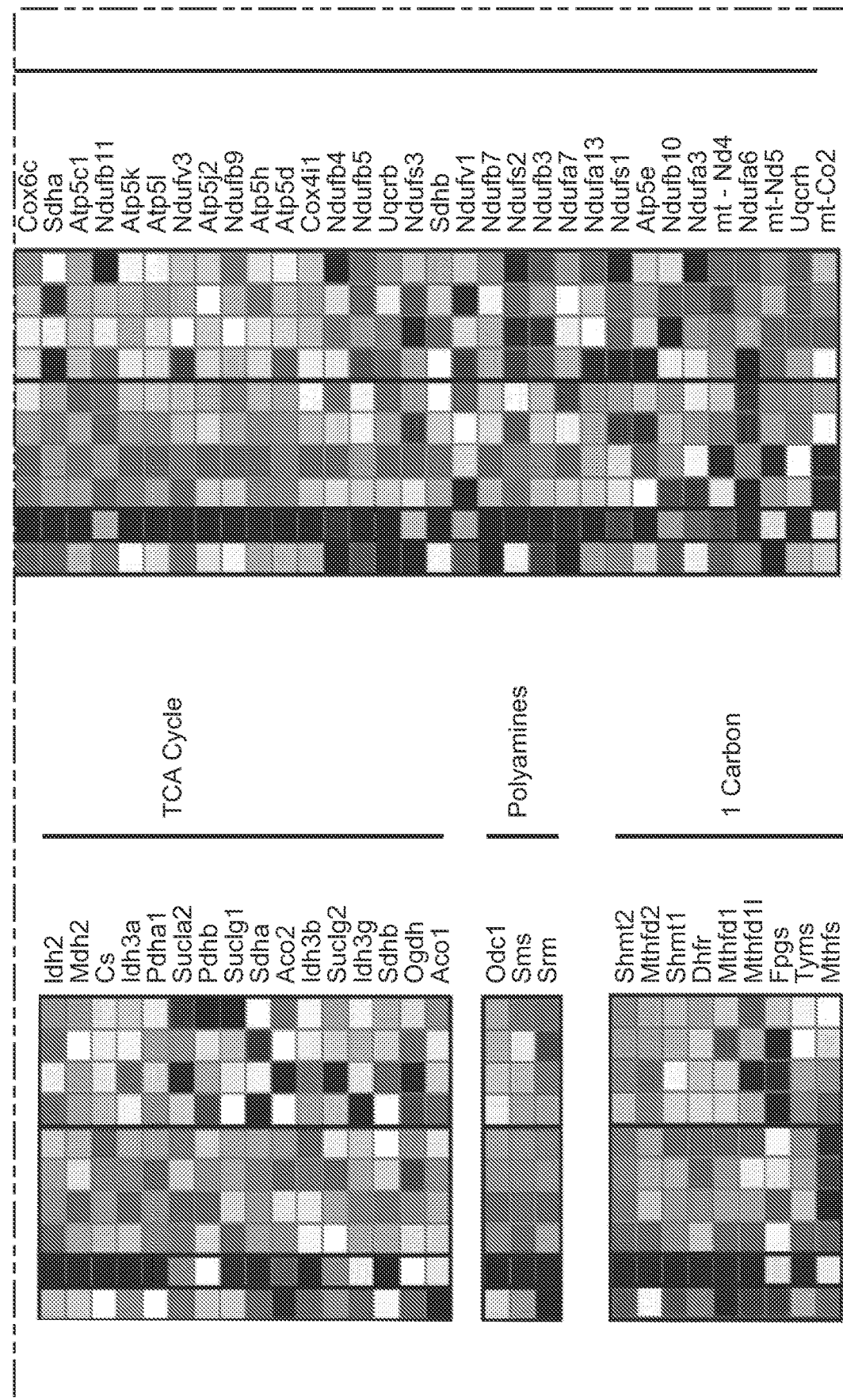
Figure 38:
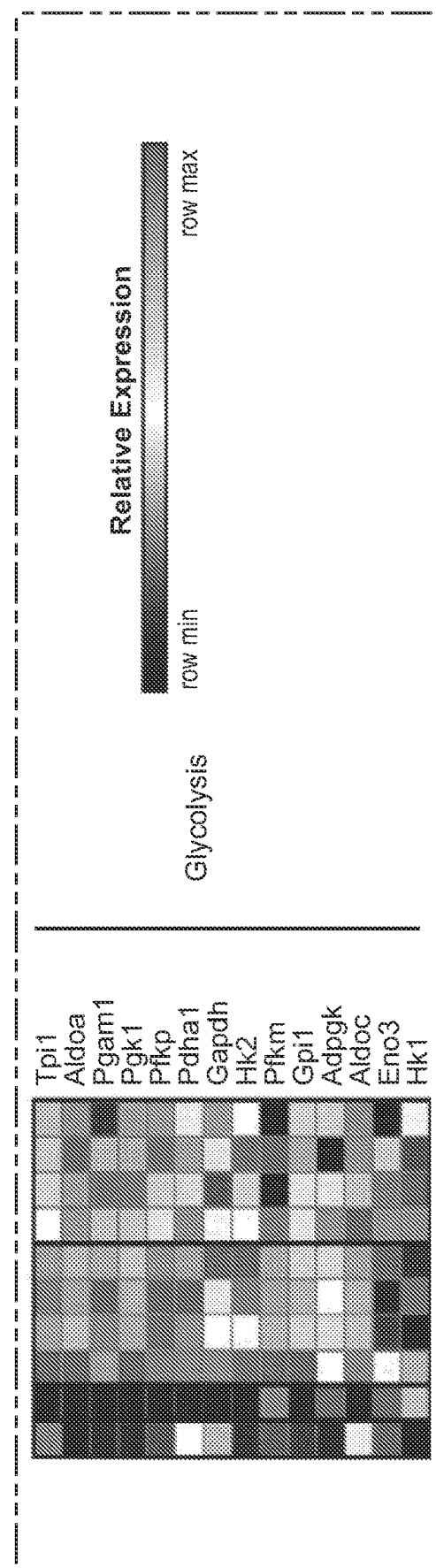
Figure 38:
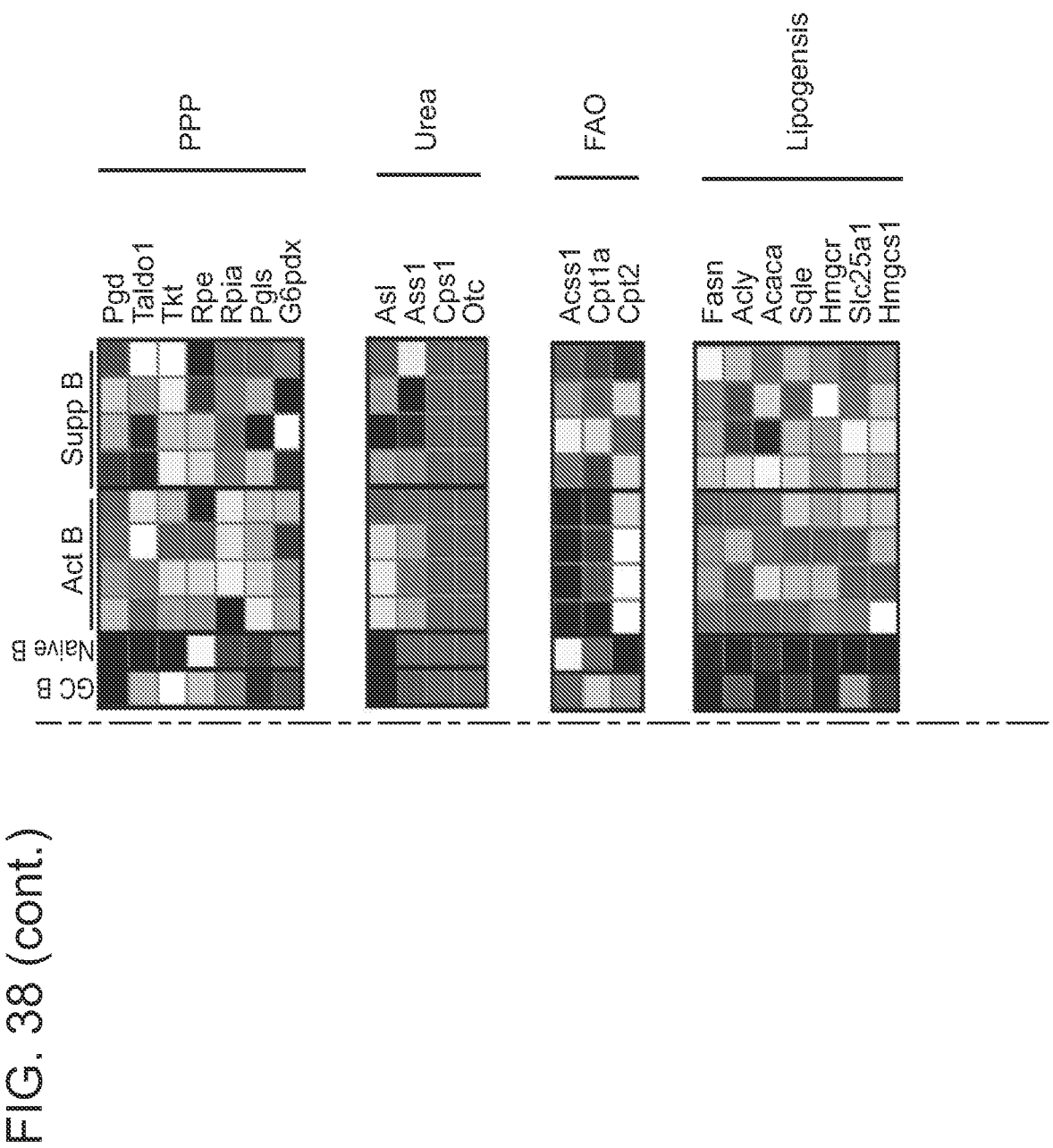

FIG. 38 shows the heat maps of individual genes in metabolic pathways (shown in FIG. 7A) from suppression assays in which B and TFH (Act B) or B, TFH and TFR were cultured.

Figure 4:
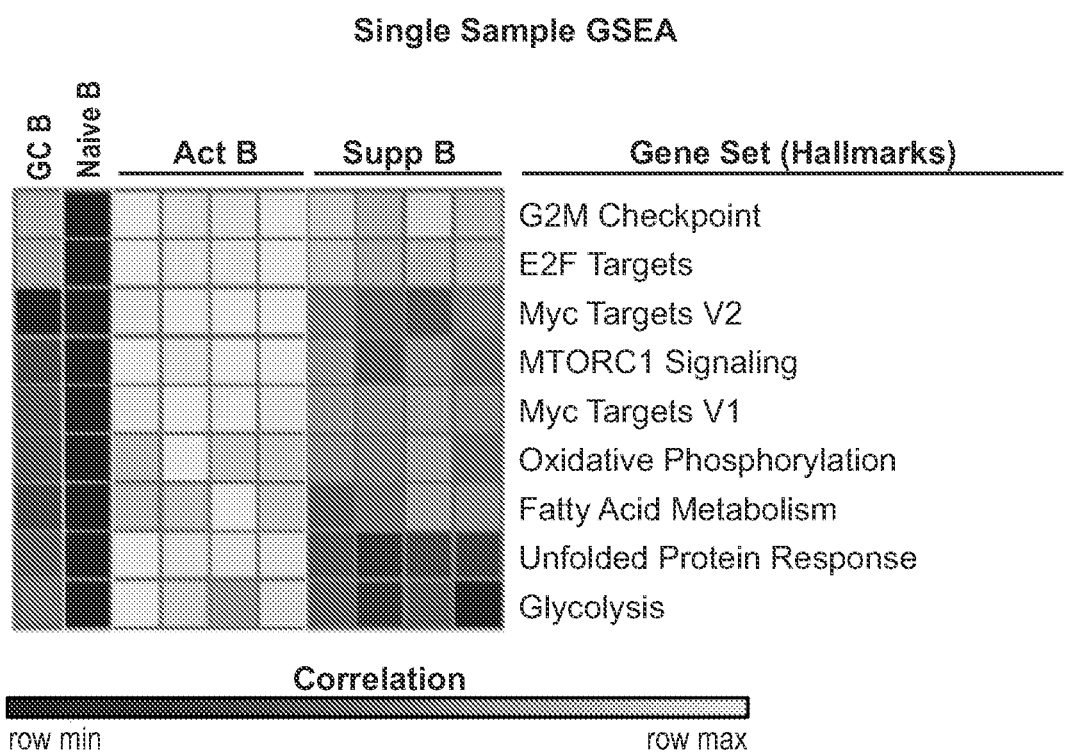
FIG. 4 shows the GSEA on genes differentially expressed during suppression.
Figure 39A:
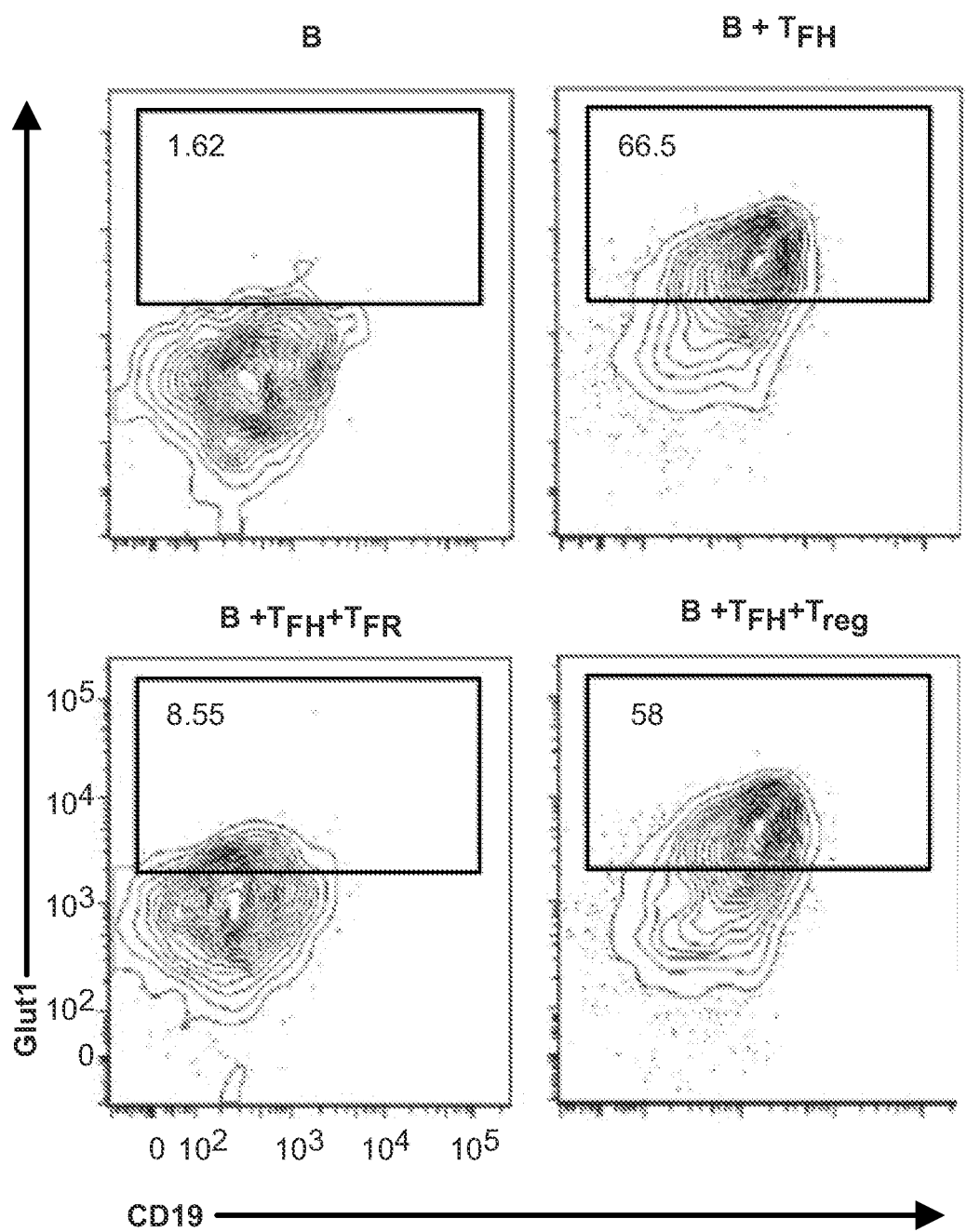
Figure 39B:
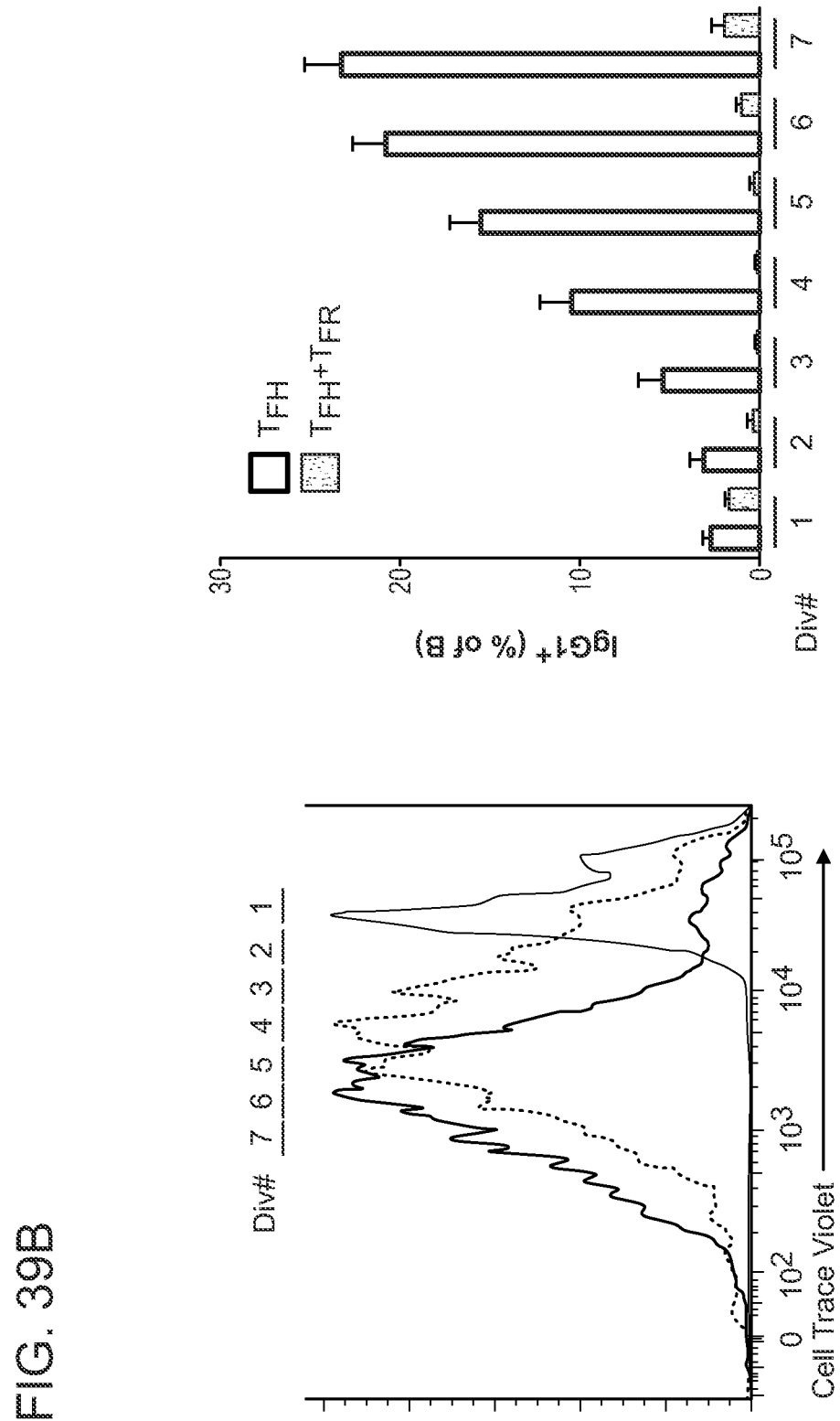
Figure 39C:
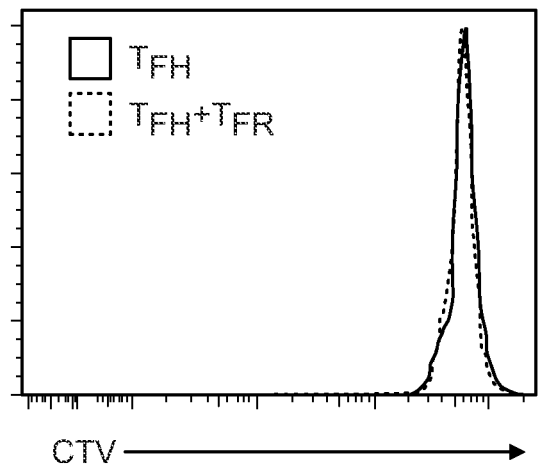
Figure 39C:
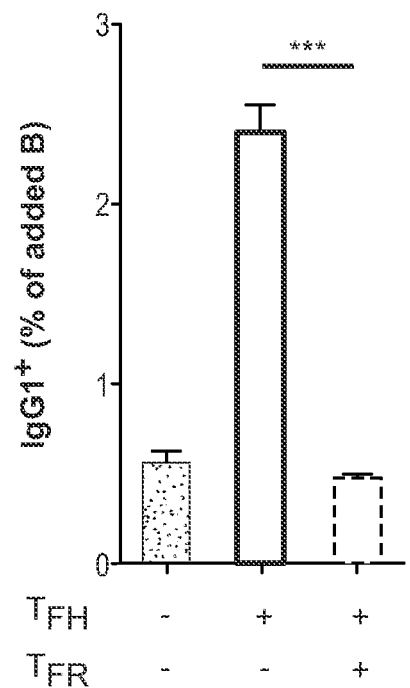
Figure 39D:
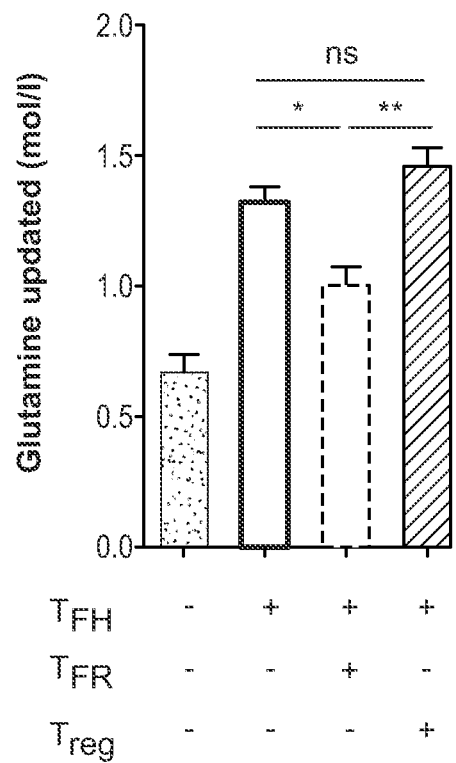
Figure 39E:
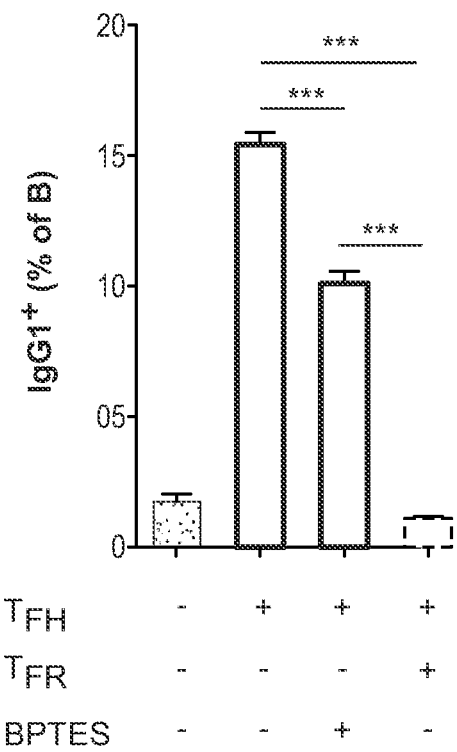

FIG. 39A-FIG. 39E show additional analysis of altered metabolic pathways in TFR cell-suppressed B cells. FIG. 39A shows Glut1 staining in B cells for experiments shown in FIG. 4b. FIG. 39B shows (left) Gating of division number for experiments shown in FIG. 4c. (right) IgG1+ staining in B cells gated by division number. FIG. 39C shows IgG1+ staining in B cells that were added to 3 day cultures and harvested 20 hours later as in FIG. 4d. FIG. 39D shows glutamine uptake measured from culture supernatants from cultures as in FIG. 4b. CD4$^+$ICOS$^-$CXCR5$^-$FoxP3$^+$ T$_{reg}$ cells were added in some conditions. FIG. 39A shows IgG1+B cells in culture supernatants from cultures as in FIG. 39A with the addition of glutaminolysis inhibitor BPTES.

Figure 40B:
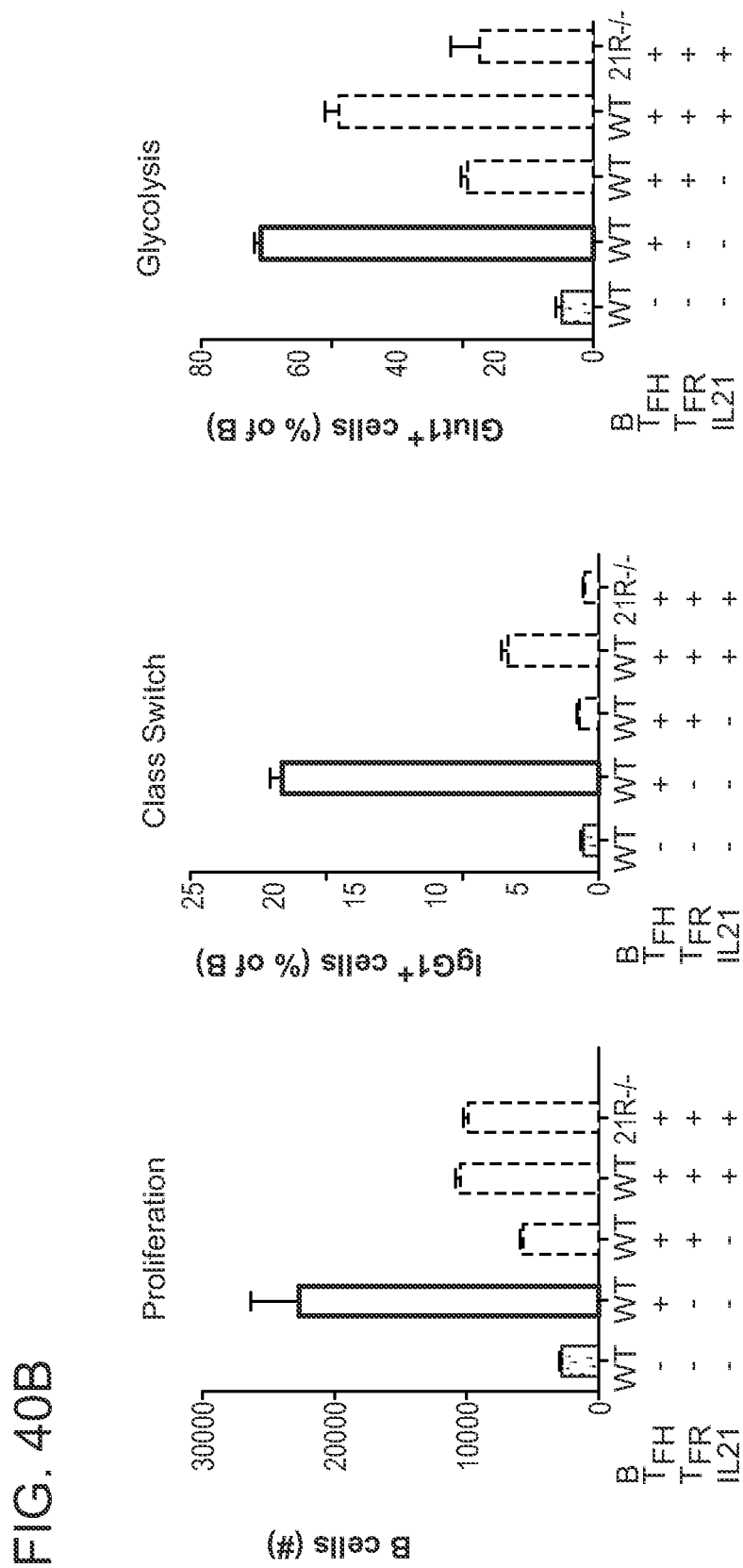

FIG. 40A-FIG. 40C show expanded analysis of 'IL-21 rescue'. FIG. 40A shows the cell count (left), IgG1+ staining (middle) and Glut1 expression (right) on B cells from suppression assays in which IL21, IL6 or IL4 were added. FIG. 40 B shows the cell count (left), IgG1+ staining (middle) and Glut1 expression (right) on B cells from suppression assays in which WT or Il21r$^{-/-}$ B cells were cultured as well as IL-21. FIG. 40C shows the heat map of genes downregulated in activated versus suppressed B cells, but not rescued with the addition of IL-21

DETAILED DESCRIPTION

U.S. application Ser. No. 14/707,596, PCT/US2013/069197, filed Nov. 8, 2013, and U.S. provisional application No. 61/724,424, filed Nov. 9, 2012, are hereby incorporated by reference in there entirety.

I. Definitions

So that the invention may be more readily understood, certain terms are first defined.

T follicular regulatory (TFR) cells as used herein include, but are not limited to, the following cell surface markers: CD4+ICOS+CXCR5+FoxP3+CD19− or CD4+ICOS+CXCR5+GITR+CD19−, or CD4+ICOS+CXCR5+CD25hiCD19−. In one embodiment, TFR cells have the following cell surface markers: CD4+CXCR5+ICOS+ and at least one surface marker selected from: GITR+, CD25hi, CD6, TIGIT, CD162, CD27, CD95, CD9, CD43, CD50, CD45RB, CD102, CD61, CD58, CD196, CD38, CD31, CD15, CD25, CD13, CD66a/c/e, CD11b CD63, CD32, CD97, HLA-HQ, CD150, Siglec-9, Integrinβ7, CD71, CD180, CD218a, CD193, CD235ab, CD35, CD140a, CD158b, CD33, CD210, HLA-G, CD167a, CD119, CX3CR1, CD146, HLA-DR, CD85, CD172b, SSEA-1, CD49c, CD170, CD66b, and CD86. In one embodiment, TFR cells have the following cell surface markers: CD4+CXCR5+ICOS+ and at least one surface marker selected from: CD27, CD278 (ICOS), CD150, Siglec-9, CD140a, CD158b, CD33.

T follicular helper (TFH) cells as used herein include, but are not limited to the following cell surface markers: CD4+ICOS+CXCR5+FoxP3−CD19−. In one embodiment, TFH cells have the following cell surface markers: CD4, CXCR5, ICOS positive and at least one marker selected from CD163, CD127, CD8a, CD89, CD197, CD161, CD6, CD229, CD96, CD272, CD148, CD107a, CD100, CD82, CD126, CD45RO, CD279, CD5, and CD99 and optionally wherein the TFH cells are negative for one or more of the following receptors GITR, CD25, CD162, CD27, CD95, CD9, CD43, CD50, CD45RB, CD102, CD61, CD58, CD196, CD38, CD31, CD15, CD25, CD13, CD66a/c/e, CD11b CD63, CD32, CD97, HLA-HQ, CD150, Siglec-9, Integrinβ7, CD71, CD180, CD218a, CD193, CD235ab, CD35, CD140a, CD158b, CD33, CD210, HLA-G, CD167a, CD119, CX3CR1, CD146, HLA-DR, CD85, CD172b, SSEA-1, CD49c, CD170, CD66b, and CD86. In one embodiment, TFH cells have the following cell surface markers: CD4, CXCR5, ICOS positive and at least one marker selected from CD163, CD127, CD161, CD6, CD229, CD272, CD100, CD126, PD-1 (CD279), and optionally wherein the TFH cells are negative for one or more of the following receptors GITR, CD25, CD162, CD27, CD95, CD9, CD43, CD50, CD45RB, CD102, CD61, CD58, CD196, CD38, CD31, CD15, CD25, CD13, CD66a/c/e, CD11b CD63, CD32, CD97, HLA-HQ, CD150, Siglec-9, Integrinβ7, CD71, CD180, CD218a, CD193, CD235ab, CD35, CD140a, CD158b, CD33, CD210, HLA-G, CD167a, CD119, CX3CR1, CD146, HLA-DR, CD85, CD172b, SSEA-1, CD49c, CD170, CD66b, and CD86.

In one embodiment, TFH cells have the following cell surface markers: CD4, CXCR5, ICOS positive and at least one marker selected from CD163, CD127, CD161, CD6, CD229, CD272, CD100, CD126, PD-1 (CD279), and optionally wherein the following markers are expressed a lower levels on TFH cells as compared to the levels of expression on TFR cells wherein such receptors are selected from: GITR, CD25, CD162, CD27, CD95, CD9, CD43, CD50, CD45RB, CD102, CD61, CD58, CD196, CD38, CD31, CD15, CD25, CD13, CD66a/c/e, CD11b CD63, CD32, CD97, HLA-HQ, CD150, Siglec-9, Integrinβ7, CD71, CD180, CD218a, CD193, CD235ab, CD35, CD140a, CD158b, CD33, CD210, HLA-G, CD167a, CD119, CX3CR1, CD146, HLA-DR, CD85, CD172b, SSEA-1, CD49c, CD170, CD66b, and CD8.

T regulatory cells (Tregs) as used herein include, but are not limited to the following cell surface markers: CD4+ GITR+CXCR5− or CD4+FoxP3+CXCR5− or CD4+ CD25hi CXCR5−.

Populations of TFH or TFR cells referred to herein as "isolated" or purified" from blood refers to cells that have been removed from the body as part of a sample taken from the peripheral blood, organs or tissues of a subject. "Isolated" and "purified" cell compositions may further be enriched for the desired cell type via known procedures for separating desired cell types from other cell populations in a sample including cell sorting. As used herein "enriched" means that the resulting sample comprises more of the desired cell type than other cell types in the sample.

The terms "inhibit", "inhibition, "suppress" and "suppression" in terms of an immune response includes the decrease, limitation or blockage of, for example a particular action, function or interaction (e.g. antibody suppression).

The terms "enhance", "promote" or "stimulate" in terms of an immune response includes an increase, facilitation, proliferation, for example a particular action, function or interaction associated with an immune response (e.g. increase in antibody production).

As used herein, the term "modulate" includes up-regulation and down-regulation, e.g., enhancing or inhibiting an immune response. The term "modulate" when used with regard to modulation of a receptor includes up-regulation or down-regulation of the biological activity associated with that receptor when the receptor is activated, for example, by its ligand or inhibited, for example, with a blocking antibody.

As used herein, the term "immune cell" refers to cells that play a role in the immune response. Immune cells are of hematopoietic origin, and include lymphocytes, such as B cells and T cells; natural killer cells; myeloid cells, such as monocytes, macrophages, eosinophils, mast cells, basophils, and granulocytes.

As used herein, the term "T cell" includes CD4+ T cells and CD8+ T cells. The term "antigen presenting cell" includes professional antigen presenting cells (e.g., B lymphocytes, monocytes, dendritic cells, Langerhans cells) as well as other antigen presenting cells (e.g., keratinocytes, endothelial cells, astrocytes, fibroblasts, oligodendrocytes).

The term "native" cells or "wild-type" cells as used herein with reference to, for example, TFR cells, TFH cells or other cells, means that the cells are essentially phenotypically and functionally the same as those cells of the same cell-type generally found at the original source of the native or wild type cells, such as, for example, TFR cells normally found in the blood, organs or tissue of a subject.

The term TFR cells with "enhanced suppressive capacity" or "enhanced immune suppressive activity" or "enhanced regulatory capacity" refers to TFR cells that have been modulated in such a way (for instance activated during PD-1 blockade) so they are more potent in their ability to inhibit B cell responses. Enhanced immune suppressive activity may be measured by standard in vivo and in vitro assays such as antibody suppression assays as are known in the art and described herein.

The term TFH cells with "enhanced stimulatory capacity", "enhanced immune stimulatory capacity" or "enhanced antibody stimulatory capacity" refers to TFH cells that have been modulated in such a way (for instance activated during PD-1 blockade or activated in the presence of IL-21) so they have more potent ability to stimulate B cell responses. Enhanced stimulatory capacity may be measured, for example, by the novel in vivo and in vitro antibody proliferation assays of the invention as described herein.

As used herein, the term "immune response" includes T cell mediated and/or B cell mediated immune responses and include those immune responses that are mediated by TFR cells or TFH cells. Exemplary immune responses include T cell responses, e.g., cytokine production, and cellular cytotoxicity. In addition, the term immune response includes immune responses that are indirectly affected by T cell activation, e.g., antibody production (humoral responses) and activation of cytokine responsive cells, e.g., macrophages.

A "subject" is preferably a human subject but can also be any mammal, including an animal model, in which modulation of an autoimmune reaction is desired.

Mammals of interest include, but are not limited to: rodents, e.g. mice, rats; livestock, e.g. pigs, horses, cows, etc., pets, e.g. dogs, cats; and primates. A subject may also be a donor of peripheral blood T cells who is not the subject in which modulation of an autoimmune reaction is desired also referred to herein as a "healthy donor". A subject may also be referred to herein as a "patient".

The terms "treatment" "treat" and "treating" encompasses alleviation, cure or prevention of at least one symptom or other aspect of a disorder, disease, illness or other condition (collectively referred to herein as a "condition"), or reduction of severity of the condition, and the like. A composition of the invention need not affect a complete cure, or eradicate every symptom or manifestation of a disease, to constitute a viable therapeutic agent. As is recognized in the pertinent field, drugs employed as therapeutic agents may reduce the severity of a given disease state, but need not abolish every manifestation of the disease to be regarded as useful therapeutic agents. Beneficial or desired clinical results include, but are not limited to, alleviation of symptoms, diminishment of extent of disease, stabilization (i.e., not worsening) of disease, delay or slowing of disease progression, amelioration or palliation of the disease state, remission (whether partial or total, whether detectable or undetectable) and prevention of relapse or recurrence of disease. Similarly, a prophylactically administered treatment need not be completely effective in preventing the onset of a condition in order to constitute a viable prophylactic agent. Simply reducing the impact of a disease (for example, by reducing the number or severity of its symptoms, or by increasing the effectiveness of another treatment, or by producing another beneficial effect), or reducing the likelihood that the disease will occur or worsen in a subject, is sufficient.

"Treatment" can also mean prolonging survival as compared to expected survival if not receiving treatment. In one embodiment, an indication that a therapeutically effective amount of a composition has been administered to the patient is a sustained improvement over baseline of an indicator that reflects the severity of the particular disorder.

By a "therapeutically effective amount" of a composition of the invention is meant an amount of the composition which confers a therapeutic effect on the treated subject, at a reasonable benefit/risk ratio applicable to any medical treatment. The therapeutic effect is sufficient to "treat" the patient as that term is used herein.

As used herein, "cell therapy" is a method of treatment involving the administration of live cells.

"Adoptive immunotherapy" is a treatment process involving removal of cells from a subject, the processing of the cells in some manner ex-vivo and the infusion of the processed cells into the same subject as a therapy.

As used herein, a vaccine is a composition that provides protection against a viral infection, cancer or other disorder or treatment for a viral infection, cancer or other disorder. Protection against a viral infection, cancer or other disorder will either completely prevent infection or the tumor or other disorder or will reduce the severity or duration of infection, tumor or other disorder if subsequently infected or afflicted with the disorder. Treatment will cause an amelioration in one or more symptoms or a decrease in severity or duration. For purposes herein, a vaccine results from co-infusion (either sequentially or simultaneously) of an antigen and a composition of cells produced by the methods herein. As used herein, amelioration of the symptoms of a particular disorder by administration of a particular composition refers to any lessening, whether permanent or temporary, lasting or transient that can be attributed to or associated with administration of the composition.

As used herein a "vaccination regimen" means a treatment regimen wherein a vaccine comprising an antigen and/or adjuvant is administered to a subject in combination with for example, composition of the invention comprising TFR cells and/or TFH cells, simultaneously, in either separate or combined formulations, or sequentially at different times separated by minutes, hours or days, but in some way act together to provide the desired enhanced immune response to the vaccine in the subject as compared to the subject's immune response in the absence of a TFR and/or TFH composition in accordance with the invention.

The term "adjuvant" is used in its broadest sense as any substance which enhances, increases, upwardly modulates or otherwise facilitates an immune response to an antigen. The immune response may be measured by any convenient means such as antibody titre or level of cell-mediated response.

"Immune-related disease" means a disease in which the immune system is involved in the pathogenesis of the disease. Subsets of immune-related diseases are autoimmune diseases. Autoimmune diseases include, but are not limited to, rheumatoid arthritis, myasthenia gravis, multiple sclerosis, psoriasis, systemic lupus erythematosus, autoimmune thyroiditis (Hashimoto's thyroiditis), Graves' disease, inflammatory bowel disease, autoimmune uveoretinitis, polymyositis, and certain types of diabetes. Other immune-related diseases are provided infra. In view of the present disclosure, one skilled in the art can readily perceive other autoimmune diseases treatable by the compositions and methods of the present invention.

A disease or condition wherein modulation of, and preferably selective modulation of, TFR cells and/or TFH cells is therapeutic, includes diseases wherein suppression of a pathogenic antibody response is desired and diseases where enhancement of a protective antibody response is desired. In some instances, for example, in a disease in which suppression of a pathogenic antibody response is therapeutic, it is contemplated herein that the disease may be treated by selectively up-regulating TFR cell-mediated antibody suppression while simultaneously selectively down-regulating TFH cell-mediated immune response.

Examples of diseases or conditions wherein suppression of a pathological antibody response is desired include diseases in which antibodies contribute to, or are primarily responsible for pathogenesis. Such diseases or conditions in which antibodies contribute to and/or are primarily responsible for pathogenesis include, but are not limited to, diabetes (Type 1), multiple sclerosis, systemic lupus erythematosus, allergy, asthma, multiple sclerosis, myasthenia gravis, lupus erythematosus, autoimmune hemolytic, scleroderma and systemic sclerosis, Sjogren's syndrom, undifferentiated connective tissue syndrome, antiphospholipid syndrome, vasculitis (polyarteritis nodosa, allergic granulomatosis and angiitis, Wegner's granulomatosis, hypersensitivity vasculitis, polymyositis systemic lupus erythematosus, collagen diseases, autoimmune hepatitis, primary (autoimmune) sclerosing cholangitis or other hepatic diseases, thyroiditis, glomerulonephritis, Devic's disease, autoimmune throbocytopenic purpura, pemphigus vulgaris, vasculitis caused by ANCA, Goodpasture's syndrome, rheumatic fever, Grave's disease (hyperthyroidism), insulin resistant diabetes, pernicious anemia, celiac disease, hemolytic disease of the newborn, cold aggutinin disease, IgA nephropathology, glomerulonephritis (including post-streptococcal), primary biliary cirrhosis, and serum sickness. In one embodiment diseases in which pathogenic antibodies contribute to and/or are primarily responsible for pathogenesis are selected from multiple sclerosis, systemic lupus erythematosus, allergy, myasthenia gravis, collagen diseases, glomerulonephritis, Devic's disease, vasculitis caused by ANCA, and celiac disease.

Examples of diseases or conditions wherein enhancement of a protective antibody response is desired includes those diseases in which the presence of a robust antibody response reduces or eliminates the causes or pathogenesis of the disease. Examples of diseases or conditions benefiting from a protective antibody response include, but are not limited to viral, pathogenic, bacterial, or fungal infections and cancer.

Viral infectious diseases including human papilloma virus (HPV), hepatitis A Virus (HAV), hepatitis B Virus (HBV), hepatitis C Virus (HCV), Zika Virus, retroviruses such as human immunodeficiency virus (HIV-1 and HIV-2), herpes viruses such as Epstein Barr Virus (EBV), cytomegalovirus (CMV), HSV-1 and HSV-2, influenza virus, Hepatitis A and B, FIV, lentiviruses, pestiviruses, West Nile Virus, measles, smallpox, cowpox, ebola, coronavirus, retrovirus, herpesvirus, potato S virus, simian Virus 40 (SV40), Mouse Mammary Tumor Virus (MMTV) promoter, Moloney virus, ALV, Cytomegalovirus (CMV), Epstein Barr Virus (EBV), or Rous Sarcoma Virus (RSV). In addition, bacterial, fungal and other pathogenic diseases are included, such as *Aspergillus, Brugia, Candida, Chikungunya, Chlamydia, Coccidia, Cryptococcus, Dengue, Dirofilaria, Gonococcus, Histoplasma, Leishmania, Mycobacterium, Mycoplasma, Paramecium, Pertussis, Plasmodium, Pneumococcus, Pneumocystis, P. vivax* in *Anopheles* mosquito vectors, *Rickettsia, Salmonella, Shigella, Staphylococcus, Streptococcus, Toxoplasma* and Vibriocholerae. Exemplary species include *Neisseria gonorrhea, Mycobacterium tuberculosis, Candida albicans, Candida tropicalis, Trichomonas vaginalis, Haemophilus vaginalis*, Group B *Streptococcus* sp., *Microplasma hominis, Hemophilus ducreyi, Granuloma inguinale, Lymphopathia venereum, Treponema pallidum, Brucella abortus. Brucella melitensis, Brucella suis, Brucella canis, Campylobacter fetus, Campylobacter fetus intestinalis, Leptospira pomona, Listeria monocytogenes, Brucella ovis, Chlamydia psittaci, Trichomonas foetus, Toxoplasma gondii, Escherichia coli, Actinobacillus equuli, Salmonella abortus ovis, Salmonella abortus equi, Pseudomonas aeruginosa, Corynebacterium equi, Corynebacterium pyogenes, Actinobacillus seminis, Mycoplasma bovigenitalium, Aspergillus fumigatus, Absidia ramosa, Trypanosoma equiperdum, Clostridium tetani, Clostridium botulinum*; or, a fungus, such as, e.g., *Paracoccidioides brasiliensis*; or other pathogen, e.g., *Plasmodium falciparum*. Also included are National Institute of Allergy and Infectious Diseases (NIAID) priority pathogens. These include Category A agents, such as variola major (smallpox), *Bacillus anthracis* (anthrax), *Yersinia pestis* (plague), *Clostridium botulinum* toxin (botulism), *Francisella tularensis* (tularaemia), filoviruses (Ebola hemorrhagic fever, Marburg hemorrhagic fever), arenaviruses (Lassa (Lassa fever), Junin (Argentine hemorrhagic fever) and related viruses); Category B agents, such as *Coxiella burnetti* (Q fever), *Brucella* species (brucellosis), *Burkholderia mallei* (glanders), alphaviruses (Venezuelan encephalomyelitis, eastern & western equine encephalomyelitis), ricin toxin from *Ricinus communis* (castor beans), epsilon toxin of *Clostridium perfringens; Staphylococcus* enterotoxin B, *Salmonella* species, *Shigella dysenteriae, Escherichia coli* strain o157:H7, *Vibrio cholerae, Cryptosporidium parvum*; Category C agents, such as nipah virus, hantaviruses, yellow fever in *Aedes* mosquitoes, and multidrug-resistant tuberculosis; helminths, such as *Schistosoma* and *Taenia*; and protozoa, such as *Leishmania* (e.g., *L. mexicana*) in sand flies, *Plasmodium*, Chagas disease in assassin bugs.

Bacterial pathogens include, but are not limited to, bacterial pathogenic gram-positive cocci, which include but are not limited to: pneumococci; staphylococci; and streptococci. Pathogenic gram-negative cocci include: meningococci; and gonococci. Pathogenic enteric gram-negative bacilli include: enterobacteriaceae; *pseudomonas*, acinetobacteria and eikenella; melioidosis; *salmonella*; shigellosis; hemophilus; chancroid; brucellosis; tularemia; *yersinia* (*pasteurella*); *streptobacillus moniliformis* and spirilum; *listeria monocytogenes*; erysipelothrix rhusiopathiae; diphtheria; cholera; anthrax; and donovanosis (granuloma inguinale). Pathogenic anaerobic bacteria include; tetanus; botulism; other clostridia; tuberculosis; leprosy; and other mycobacteria. Pathogenic spirochetal diseases include: syphilis; treponematoses: yaws, pinta and endemic syphilis; and leptospirosis. Other infections caused by higher pathogen bacteria and pathogenic fungi include: actinomycosis;

nocardiosis; cryptococcosis, blastomycosis, histoplasmosis and coccidioidomycosis; candidiasis, aspergillosis, and mucormycosis; sporotrichosis; paracoccidiodomycosis, petriellidiosis, torulopsosis, mycetoma and chromomycosis; and dermatophytosis. Rickettsial infections include rickettsial and rickettsioses. Examples of *mycoplasma* and chlamydial infections include: *mycoplasma pneumoniae*; lymphogranuloma venereum; psittacosis; and perinatal chlamydial infections. Pathogenic protozoans and helminths and infections eukaryotes thereby include: amebiasis; malaria; leishmaniasis; trypanosomiasis; toxoplasmosis; *pneumocystis carinii*; giardiasis; trichinosis; filariasis; schistosomiasis; nematodes; trematodes or flukes; and cestode (tapeworm) infections. While not a disease or condition, enhancement of a protective antibody response is also beneficial in a vaccine or as part of a vaccination regimen as is described herein.

The term "cancer" as used herein refers to an abnormal growth of cells which tend to proliferate in an uncontrolled way and, in some cases, to metastasize (spread). The types of cancer include, but is not limited to, solid tumors (such as those of the bladder, bowel, brain, breast, endometrium, heart, kidney, lung, uterus, lymphatic tissue (lymphoma), ovary, pancreas or other endocrine organ (thyroid), prostate, skin (melanoma or basal cell cancer) or hematological tumors (such as the leukemias and lymphomas) at any stage of the disease with or without metastases.

Additional non-limiting examples of cancers include, acute lymphoblastic leukemia, acute myeloid leukemia, adrenocortical carcinoma, anal cancer, appendix cancer, astrocytomas, atypical teratoid/rhabdoid tumor, basal cell carcinoma, bile duct cancer, bladder cancer, bone cancer (osteosarcoma and malignant fibrous histiocytoma), brain stem glioma, brain tumors, brain and spinal cord tumors, breast cancer, bronchial tumors, Burkitt lymphoma, cervical cancer, chronic lymphocytic leukemia, chronic myelogenous leukemia, colon cancer, colorectal cancer, craniopharyngioma, cutaneous T-Cell lymphoma, embryonal tumors, endometrial cancer, ependymoblastoma, ependymoma, esophageal cancer, ewing sarcoma family of tumors, eye cancer, retinoblastoma, gallbladder cancer, gastric (stomach) cancer, gastrointestinal carcinoid tumor, gastrointestinal stromal tumor (GIST), gastrointestinal stromal cell tumor, germ cell tumor, glioma, hairy cell leukemia, head and neck cancer, hepatocellular (liver) cancer, Hodgkin lymphoma, hypopharyngeal cancer, intraocular melanoma, islet cell tumors (endocrine pancreas), Kaposi sarcoma, kidney cancer, Langerhans cell histiocytosis, laryngeal cancer, leukemia, Acute lymphoblastic leukemia, acute myeloid leukemia, chronic lymphocytic leukemia, chronic myelogenous leukemia, hairy cell leukemia, liver cancer, lung cancer, non-small cell lung cancer, small cell lung cancer, Burkitt lymphoma, cutaneous T-cell lymphoma, Hodgkin lymphoma, non-Hodgkin lymphoma, lymphoma, Waldenstrom macroglobulinemia, medulloblastoma, medulloepithelioma, melanoma, mesothelioma, mouth cancer, chronic myelogenous leukemia, myeloid leukemia, multiple myeloma, nasopharyngeal cancer, neuroblastoma, non-Hodgkin lymphoma, non-small cell lung cancer, oral cancer, oropharyngeal cancer, osteosarcoma, malignant fibrous histiocytoma of bone, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, retinoblastoma, rhabdomyosarcoma, salivary gland cancer, sarcoma, Ewing sarcoma family of tumors, sarcoma, kaposi, Sezary syndrome, skin cancer, small cell Lung cancer, small intestine cancer, soft tissue sarcoma, squamous cell carcinoma, stomach (gastric) cancer, supratentorial primitive neuroectodermal tumors, T-cell lymphoma, testicular cancer, throat cancer, thymoma and thymic carcinoma, thyroid cancer, urethral cancer, uterine cancer, uterine sarcoma, vaginal cancer, vulvar cancer, Waldenstrom macroglobulinemia, Wilms tumor.

An agent that is an "antagonist" of a cell surface receptor on a TFH cell or a TFR cell is an agent which down regulates or blocks the biological function of the cell surface receptor. As used herein, an agent which is an "antagonist" includes agents that bind or otherwise interfere with ligands of cell surface receptor thereby blocking the ability of the ligand to bind to the cell surface receptor and down-regulate or prevent the biological function of the cell surface receptor.

An agent that is an "agonist" of a cell surface receptor on a TFH cell or a TFR cell is an agent which upregulates or increases the biological function of the cell surface receptor.

II. Starting Population of Cells

In one embodiment TFR cells and TFR precursor cells, for example, T regulatory (Treg) progenitor cells are derived from a mixed cell population containing such cells (e.g. from peripheral blood, tissue or organs). Preferably the mixed cell population containing TFR cells or TFR cell precursors is enriched such that TFR cells or TFR cell precursors comprise more TFR cells than other cell types in the population. In one embodiment, an enriched composition of TFR cells is a composition wherein the TFR cells make up greater than about 50% (e.g., 55%, 60%, 65%, 70%, 75%, 80%, 85%, 90%, 95%, 98%, 99%, 99.5%, 99.9% or more) of the cell population in the composition. In some embodiments, the TFR cells comprise about 90%, 95%, 98%, 99%, 99.5%, 99.9% or more of the cells in the composition, and such compositions are referred to herein as "highly purified" or "substantially homogenous" TFR cell compositions.

While a starting population of TFR cells is described above, it is understood that similar procedures may be applied to obtaining a starting population of TFH cells.

Accordingly in some embodiments a mixed cell population containing TFH is enriched such that the composition comprises more TFH cells than other cell types in the population. In one embodiment, an enriched composition of TFH cells is a composition wherein the TFH cells make up greater than about 50% (e.g., 55%, 60%, 65%, 70%, 75%, 80%, 85%, 90%, 95%, 98%, 99%, 99.5%, 99.9% or more) of the cell population in the composition. In some embodiments, the TFH cells comprise about 90%, 95%, 98%, 99%, 99.5%, 99.9% or more of the cells in the composition, and such compositions are referred to herein as "highly purified" or "substantially homogenous" TFH cell compositions. In some embodiments, TFR cells or TFH cells are enriched from a population of cells prior to an activating and/or expanding step. In some embodiments TFR cells or TFH cells are enriched from a population of cells after the activating and/or expanding step.

Such highly purified or substantially homogenous populations of TFR cells or TFH cells may be used for in-vivo and in-vitro diagnoses and examination of TFR cell-mediated, or TFH cell-mediated diseases.

TFR cells can be enriched by targeting for selection of cell surface markers specific for immune suppressive TFR cells and separating using automated cell sorting such as fluorescence-activated cell sorting (FACS), solid-phase magnetic beads, etc. To enhance enrichment, positive selection may be combined with negative selection against cells comprising surface makers specific to non-T-regulatory cell types, such as depletion of CD8, CD11b, CD16, CD19, CD36 and CD56-bearing cells.

In one embodiment TFR cells are sorted via flow cytometry based on surface markers of CD4+CXCR5+ICOS+GITR+, or CD4+CXCR5+ICOS+CD25+. In one embodiment, TFR cells are sorted via flow cytometry based on the following cell surface markers: CD4+CXCR5+ICOS+ and at least one surface marker selected from one or more of: GITR+, CD25hi, TIGIT, CD6, CD162, CD27, CD95, CD9, CD43, CD278, CD50, CD45RB, CD102, CD61, CD58, CD196, CD38, CD31, CD15, CD25, CD13, CD66a/c/e, CD11b CD63, CD32, CD97, HLA-HQ, CD150, Siglec-9, Integrinβ7, CD71, CD180, CD218a, CD193, CD235ab, CD35, CD140a, CD158b, CD33, CD210, HLA-G, CD167a, CD119, CX3CR1, CD146, HLA-DR, CD85, CD172b, SSEA-1, CD49c, CD170, CD66b, and CD86.

TFH cells may be sorted based on surface markers of CD4, CXCR5, ICOS positive; GITR negative, CD25 negative. In one embodiment, TFH cells are sorted via flow cytometry based on the following cell surface markers: CD4, CXCR5, ICOS positive and at least one marker selected from: CD163, CD127, CD8a, CD89, CD197, CD161, CD6, CD229, CD96, CD272, CD148, CD107a, CD100, CD82, CD126, CD45RO, CD279, CD5, and CD99, and optionally wherein the TFH cells are negative for one or more of the following receptors GITR, CD25, CD162, CD27, CD95, CD9, CD43, CD50, CD45RB, CD102, CD61, CD58, CD196, CD38, CD31, CD15, CD25, CD13, CD66a/c/e, CD11b CD63, CD32, CD97, HLA-HQ, CD150, Siglec-9, Integrinβ7, CD71, CD180, CD218a, CD193, CD235ab, CD35, CD140a, CD158b, CD33, CD210, HLA-G, CD167a, CD119, CX3CR1, CD146, HLA-DR, CD85, CD172b, SSEA-1, CD49c, CD170, CD66b, and CD86.

It is believed that these sorting methodologies also contribute to the enhanced functionality of TFH cells and TFR cells alone or in combination with activating such cells in the presence of an antagonist of cytokines or metabolic modulators.

In one embodiment, an initial population of TFR cells may also be isolated from the peripheral blood of a subject and further enriched for TFR cells. In one embodiment, an initial population of TFH cells may also be isolated from the peripheral blood of a subject and further enriched for TFH cells. Methods of purifying TFR cells or TFH cells from other PBMCs in the blood, using methods such as differential sedimentation through an appropriate medium, e.g. Ficoll-Hypaque [Pharmacia Biotech, Uppsala, Sweden], and/or methods of cell sorting, are well known and examples of such methods are described herein.

In one embodiment the invention provides a composition of TFR cells derived from the peripheral blood of a subject (also referred to herein as "blood TFR cells") wherein the composition comprises about 90%, 95%, 98%, 99%, 99.5%, 99.9% or more of the cells in the composition.

In one embodiment the invention provides a composition of TFH cells derived from the peripheral blood of a patient (also referred to herein as "blood TFH cells") wherein the composition comprises about 90%, 95%, 98%, 99%, 99.5%, 99.9% or more of the cells in the composition. Such high purity compositions of blood TFR cells or blood TFH cells may be used directly in methods of modulating the immune system as described herein. Alternatively such compositions may be further activated and/or expanded prior to use in modulating the immune system as described herein.

III. Activation/Expansion of Starting Population of Cells

In one embodiment, the activation of a starting cell population is achieved by contacting the starting population of TFH cells or TFR cells with T cell stimulatory composition and/or in the presence of cytokines such as IL-21 and IL-6 or metabolic modulators. The activating step may further include an expanding step or the cell population may be expanded separately from the activating step. If an expanding step is desired, the cells are preferably expanded at least 50-fold, and preferably at least 100, 200, 300, 500 and 800-fold.

Exemplary metabolic modulators include but are not limited to 2-deoxyglucose, metformin, methotrexate, azathioprine, rapamycin, dichloroacetate, lonidamine, alpha-tocopheryl succinate, methyl jasmonate, betulinic acid, and resveratrol.

Preferred stimulatory compositions stimulate the T cells by binding and activating the T cell receptor complex on the cells. In one embodiment, stimulatory compositions may include agents capable of binding and activating selective TFR and/or selective TFH receptors as described herein. In one embodiment the stimulatory compositions comprise physiological antigen presenting cells (APCs), such as CD19+ B cells (preferably autologous from blood) a TCR/CD3 activator such as a multivalent antibody or ligand for TCR/CD3; a TCR costimulator activator such as multivalent antibody or ligand for CD28, GITR, CD5, ICOS, OX40 or CD40L; and optionally an interleukin such as IL-2, IL-21 or IL-6. In one embodiment, the TCR/CD3 activator is an anti-CD3 antibody, and the TCR costimulator activator is an anti-CD28 antibody. The anti-CD3 and anti-CD28 antibodies are optionally immobilized on beads as are known in the art and provided in a cell:bead ratio of between 1:1 and 1:2.

In certain embodiments, the stimulatory composition may further include one or more additional agents, e.g., a costimulatory agent, a second regulatory T cell stimulatory agent, or agents that generally promote the survival and/or growth of T cells.

In certain embodiments, the costimulatory agent is an antibody or ligand specific for a T cell costimulator, such as CD28 or ICOS, as described below. In particular embodiments, the costimulatory agent is an agonist antibody, such as an agonist antibody which binds to CD28. The stimulatory composition alternatively comprises a second regulatory T cell stimulatory agent. Exemplary stimulatory agents include granulocyte colony stimulating factor, interleukins such as IL-2, IL-6, IL-7, IL-13, and IL-15, and hepatocyte growth factor (HGF).

In particular embodiments, one or more components of the stimulatory composition is immobilized on a substrate, such as a cell or bead. Cells suitable for use as substrates include artificial antigen-presenting cells (AAPCs) (Kim, J V et al, Nat Biotechnol. April 2004; 22(4):403-10; and Thomas, A K et al, Clin Immunol. December 2002; 105(3): 259-72). Beads can be plastic, glass, or any other suitable material, typically in the 1-20 micron range.

Examples of PD-1 and PD-1 ligand antagonists are disclosed in U.S. Pat. No. 7,722,868, incorporated herein by reference. Suitable PD-1 and PD-1 ligand antagonists include a PD1-ligand antibody, an anti-PD-1 antibody, a peptide or a small molecule wherein the agent inhibits the interaction between PD-1 and a PD-1 ligand. Other examples of PD-1 or PD-1 ligand antagonists are disclosed, for example in U.S. Pat. Nos. 8,168,757; 8,114,845; 8,008,449; 7,595,048; 7,488,802; and 7,029,674.

Optimal concentrations of each component of the stimulatory compositions, culture conditions and duration can be determined empirically using routine experimentation.

Populations of TFR cells expanded/activated in the presence of a PD-1 or PD-1 ligand antagonist have enhanced suppressive activity as demonstrated by their ability to inhibit TFH-mediated antibody production in vitro and in vivo as demonstrated in appropriate assays as are described herein.

Populations TFH cells expanded/activated in the presence of a PD-1 or PD-1 ligand antagonist have enhanced antibody stimulatory activity as demonstrated by their ability to enhance TFH-mediated antibody production in vitro and in vivo as demonstrated in appropriate assays described herein. Such TFH cells are referred to herein as "TFH cells having enhanced stimulatory capacity".

IV. Modulation of the Immune System

The expanded and/or activated TFR cells and compositions thereof as described herein may be introduced into the subject to treat immune related diseases, for example, by modulating an autoimmune reaction. For example, the subject may be afflicted with a disease or disorder characterized by having an ongoing or recurring autoimmune reaction, such as the diseases/disorders including, but not limited to, lupus erythematosus; myasthenia gravis; autoimmune hepatitis; rheumatoid arthritis; multiple sclerosis; Grave's disease, and graft versus host disease (GVHD).

In one embodiment, if upregulation of an immune response in a subject is desired, such as for example, increasing antibody amount or quality in response to a vaccine, an enriched and optionally expanded and/or activated composition comprising a starting population of TFH cells may be administered to a subject.

In one embodiment modulation of the immune system is achieved when upon administration of a composition of the invention, the ratio of TFR cells to TFH cells in a subject is changed as compared to the ratio of TFR cells to TFH cells in a subject prior to administration of a composition of the invention. The ratios of TFR cells to TFH cells in a subject prior to, and after, administration of a composition of the invention may be measured by assaying for the presence of TFR cells or TFH cells in a patient's blood. Examples of suitable assays for measuring the ratio of TFR cells to TFH cells in a patient's blood are described herein.

In one embodiment, if downregulation of a subject's immune response is desired, such as, for example, when the subject has an autoimmune disease and inhibition of an antibody response is desired, a highly purified composition of blood derived TFR cells, or a composition enriched for TFR cells having enhanced suppressive activity may be administered to a patient. After administration of the composition, a blood sample from the patient may be tested to determine if the ratio of TFR cells to TFH cells is high.

In one embodiment, if upregulation of an immune response in a subject is desired, such as for example, increasing antibody proliferation in response to a vaccine, a highly purified composition of blood-derived TFH cells may be administered to a patient. After administration of TFH composition, a blood sample from the patient may be tested to determine if the ratio of TFH cells to TFR cells is high.

Accordingly, the invention provides methods and compositions for adoptive cellular immunotherapy comprising introducing into a patient in need thereof an effective amount of the subject's ex vivo expanded/activated TFR cells, for example. These applications generally involve reintroducing expanded/activated TFR cells extracted from the same patient, though the methods are also applicable to adoptive cellular immunotherapy for treatment of graft-versus-host disease associated with transplantation, particularly bone marrow transplantation using TFRs derived from donor tissue, and/or healthy individuals.

In an exemplary adoptive cell transfer protocol comprises a mixed population of cells is initially extracted from a target donor. Depending on the application, the cells may be extracted during a period of remission, or during active disease. Typically this is done by withdrawing whole blood and harvesting PMBCs by, for example, leukapheresis (leukopheresis). For example, large volume leukopheresis (LVL) has been shown to maximize blood leukocyte yield. Harvests reach $20 \times 10^6$ cells/L using a continuous flow apheresis device (Spectra, COBE BCT). Symptoms of hypocalcemia are avoided by a continuous infusion of calcium administrated throughout leukopheresis. Typically 15-45 liters of fluid corresponding to about 4 total blood volumes are harvested during a period of time ranging from about 100 to 300 minutes.

The harvested PMBCs may be separated by flow cytometry or other cell separation techniques based on Treg and/or TFR-specific cell markers such as CD4, CD25, CXCR5, ICOS, and GITR and expanded/activated as described herein, and then transfused to a patient, preferably by the intravenous route, typically the cell donor (except in GVHD where the donor and recipient are different), for adoptive immune suppression. Alternatively, the cells may be frozen for storage and/or transport prior to and/or subsequent to expansion.

Effective and optimized dosages and treatment regimens using the expanded and/or enriched and optionally highly pure TFH or TFR cells are known in the art based on previous clinical experience with existing T-cell infusion therapies, and can be further determined empirically.

The preferred route of administration of the TFR and TFH cell compositions to a subject in accordance with the invention is by the intravenous route. However, depending on the application, cell compositions in accordance with the invention may be administered by other routes including, but not limited to, parenteral, oral or by inhalation.

V. Vaccination

The present invention also contemplates a method for enhancing an immune response to an antigen comprising the administration to a subject as part of a vaccination regimen, TFR cells having enhanced suppressive activity, TFR cell compositions derived from peripheral blood, TFH cells having enhanced stimulation activity, or TFH cells derived from peripheral blood. The present invention is particularly useful in pharmaceutical vaccines and genetic vaccines in humans.

Adjuvants promote the immune response in a number of ways such as to modify the activities of immune cells that are involved with generating and maintaining the immune response. Additionally, adjuvants modify the presentation of antigen to the immune system. The compositions of the invention may be used as adjuvants in a vaccination regimen.

In one embodiment, compositions of TFH or TFR cells in accordance with the invention may be used in a vaccination regimen. Without being limited to a specific theory, it is believed that TFR cells inhibit GC B cells, resulting in reduced class switch recombination and antibody production and TFH cells stimulate GC B cells and antibody production.

In one embodiment compositions of TFH cells, particularly TFH cells derived from the peripheral blood of a patient (also referred to herein as "blood TFH cells") may be used in a vaccination regimen to enhance TFH cell mediated antibody responses. Without being limited to any particular theory, it is believed that TFH cells derived from the blood migrate to lymph nodes and interact with cognate B cells rapidly upon antigen exposure, wherein naïve T cells need at least two to four days to differentiate and upregulate CXCR5. Accordingly, TFH cells derived from blood have greater antibody stimulatory capacity.

In one embodiment, it may be desirable to upregulate an immune response or downregulate an immune response as part of a vaccination regimen. This can be accomplished by administering compositions enriched for or highly purified for TFR cells or compositions enriched for or highly purified TFH cells to change the ratio of TFR cells to TFH cells in a subject's blood in combination with the administration of a vaccine.

In some embodiments, the vaccine may comprise a composition of TFH cells and a cytokine (e.g., IL-21 or IL-6) or metabolic modulator.

The present invention also contemplates a method for enhancing an immune response to an antigen comprising the administration to a subject as part of a vaccination regimen a cytokine (e.g., IL-21 or IL-6) or metabolic modulator. Administering an antigen and/or adjuvant to a subject in combination with IL-21, IL-6 or metabolic modulators may inhibit the activity of the subjects TFR cells resulting in a similar effect as TFH/TFR compositions Exemplary metabolic modulators include but are not limited to 2-deoxyglucose, metformin, methotrexate, azathioprine, rapamycin, dichloroacetate, lonidamine, alpha-tocopheryl succinate, methyl jasmonate, betulinic acid, and resveratrol.

VI. Novel In-Vivo and In Vitro Assays

The invention also provides in vivo and in vitro assays to analyze the functions of the compositions of TFR cells and TFH cells in accordance with the invention.

In one exemplary embodiment the invention provides an assay to analyze the capacity of TFR cells to inhibit activation of CD4 T cell populations such as TFH cells. Briefly, WT and PD-1−/− mice are immunized with MOG/CFA and TFR cells are sorted from draining lymph nodes and plated 1:1:1 with CF SE-labeled CD4 naïve WT (CD4+CD62L+ FoxP3−) responder cells and WT GL7-B220+B cells from MOG/CFA immunized mice along with anti-CD3 and anti-IgM for 4 days. 3 days later samples are analyzed by flow cytometry. It is understood that any suitable antigen/adjuvant combinations may be used to immunize mice and that the cells may be stimulated by any suitable combinations of stimulatory factors for this assay.

In one exemplary embodiment the invention provides an assay to analyze capacity of TFR cells to inhibit activation of naïve CD4 T cells. WT and PD-1−/− mice are immunized with MOG/CFA and TFR cells and sorted from draining lymph nodes and plated 1:1:1 with CFSE-labeled CD4 naïve WT (CD4+CD62L+FoxP3−) responder cells and WT GL7-B220+B cells from MOG/CFA immunized mice along with anti-CD3 and anti-IgM for 4 days. 3 days later samples are analyzed by flow cytometry. T responders are analyzed for CD69 expression and proliferation by measuring CFSE dilution.

In one embodiment the invention provides an assay for an in vitro IgG suppression.

Briefly, TFR cells are sorted as in the assay to analyze capacity of TFR cells to inhibit activation of naïve CD4 T cells and are plated in a 1:1:1 ratio of TFR (CD4+ICOS+ CXCR5+GITR+CD19−), TFH (CD4+ICOS+CXCR5+ GITR-CD19−), and B (GL-7-B220+) cells from draining lymph nodes of MOG/CFA immunized mice in the presence of anti-CD3 and anti-IgM for 6 days. Total IgG was measured by ELISA from supernatants. In one embodiment the in-vitro suppression assay may be performed over a range of concentrations of anti-CD3. Naive (CD4+ICOS−CXCR5− CD19−) cells from immunized mice may be included as controls. It is understood that any suitable antigen/adjuvant combinations may be used to immunize mice and that the cells may be stimulated by any suitable combinations of stimulatory factors for this assay.

Novel assays of the invention are useful as a diagnostic tool for measuring a subject's TFR cell function and TFH cell function. Such assays are useful in the identification and typing of autoimmune diseases.

The assays of the invention are also useful in measuring the ratio of TFR cells to TFH cells in a patient's blood prior to or during an immune response and/or prior to and after administration of a composition of the invention. Such assays are useful as a diagnostic to assist in determining whether an immune response in a subject should be upregulated or down-regulated or whether an immune modulating treatment regimen has had the desired effect. This assay also may be useful in the diagnosis or progression of specific diseases.

In accordance with the invention, an exemplary assay comprises a method for assaying the TFR cell function or the TFH cell function or both, in a patient comprising the steps of:

a) Obtaining a sample of peripheral blood from a patient;
    b) Isolating a population of TFH cells and TFR cells from the blood sample;
    c) Contacting the TFH cells and TFR cells with a stimulatory composition comprising antigen present cells (e.g. B cells) in the presence of T-cell receptor stimulating factors and cofactors such as anti-CD3 and anti-IgM, for a time period sufficient to allow the production of antibody such as IgG; and
    d) measuring the total antibody produced using standard assays (e.g. ELISA).

VII. Modulation of TFR and TFH Cell-Mediated Immune Responses Via Selective TFR and TFH Cell Surface Receptors The data in FIG. 23 of PCT/US2013/069197, hereby incorporated by reference, shows that TFR cells are distinct in their gene expression as compared to Treg cells and TFH cells suggesting that TFR cells are capable of independently regulating immune responses. This knowledge may be applied to diagnose, monitor and treat diseases or conditions wherein TFR-immune responses may be selectively modulated such as in those diseases or conditions in which antibodies play a key role in the pathogenesis and enhanced immune suppression is therapeutic. Examples of such diseases are provided herein supra.

TFR cell function may be modulated by use of an agent such as an agonist or an antagonist of one or more of TFR cell surface receptors as described herein. Use of such an agent in an amount effective to inhibit or induce the differentiation of TFR cells and/or modulate the biological function of TFR cells can affect the TFR cell-mediated immune response.

In one embodiment, the invention provides a method suppressing a pathogenic antibody response in a patient in need thereof comprising, administering to the patient, an agent which modulates at least one receptor which is differentially expressed on TFR cells as compared to TFH cells at an increased mean fluorescence intensity (MFI) fold change of at least 1.17, and wherein the receptor has an MFI of at least 186 on TFR cells and wherein the agent administered in an amount that is effective to modulate the TFR receptor and increase TFR cell-mediated antibody suppression, as compared to the TFR cell-mediated antibody suppression in the absence of the agent. Such differentially expressed receptors are referred to herein as "selective TFR receptors". In one embodiment at least one selective TFR receptor is selected from one or more of: CD162, CD27, CD95, CD9, CD43, CD278 (ICOS), CD50, CD45RB, CD102, CD61, CD58, CD196, CD38, CD31, CD15, CD25, CD13, CD66a/c/e, CD11b CD63, CD32, CD97, HLA-HQ, CD150, Siglec-9, Integrinβ7, CD71, CD180, CD218a, CD193, CD235ab, CD35, CD140a, CD158b, CD33, CD210, HLA-G, CD167a, CD119, CX3CR1, CD146, HLA-DR, CD85, CD172b, SSEA-1, CD49c, CD170, CD66b, and CD86. In one embodiment, selective TFR receptors are selected from one or more of: CD27, CD278 (ICOS), CD150, Siglec-9, CD140a, CD158b, and CD33.

Methods of modulating TFR cell-mediated immune response through antagonizing or agonizing the biological function of a selective TFR receptor are useful in the treatment of diseases and conditions wherein a decreased or increased TFR cell-mediated immune response is useful. Examples of disorders or conditions which may be treated by increasing TFR cell-mediated immune response include those diseases and conditions in which antibodies contribute to and/or are primarily responsible for, pathogenesis such as in those diseases listed previously herein. In one embodiment the disease or condition in which antibodies contribute and/or are primarily responsible for pathogenesis include: multiple sclerosis, systemic lupus erythematosus, allergy, myasthenia gravis, collagen diseases, glomerulonephritis, Devic's disease, vasculitis caused by ANCA, and celiac disease.

In one embodiment, the agent is a blocking antibody capable of blocking/antagonizing a selective TFR receptor, or binding to the ligand of the receptor and thereby blocking its ability to bind its corresponding receptor. The agent may also be a small molecule, or a DNA or RNA molecule (e.g. dsRNA, or antisense molecule) capable of antagonizing or agonizing the biological function of the receptor, for example by causing overexpression of a receptor or by blocking expression of a receptor.

In addition to the known agonists and antagonists of various selective TFR receptors known generally, other agents may be tested for their ability to antagonize or agonize selective TFR receptors using known assays and screens.

Assays and screens of the invention useful for testing various agents for their ability to agonize or antagonize TFR cell surface receptors are used to identify agents of the invention. In one embodiment, the invention provides assays to specifically and sensitively determine the stimulatory function of TFH cells. Complementary assays are also provided which determine the inhibitory capacity of TFR cells. These assays which include both in vitro and in vivo experiments can be used to determine the functional consequences of sending agonist and/or antagonist signals through surface receptors on TFH and TFR cells.

In vitro murine TFH stimulation assays are performed by immunizing/vaccinating mice with an antigen/adjuvant. In some cases live or attenuated virus can be used. Seven to ten days later TFH cells defined as (CD4+ICOS+CXCR5+FoxP3+CD19−) or (CD4+ICOS+CXCR5+GITR+CD19−) (or alternative TFH marker) are sorted by flow cytometry. TFH cells are incubated with B cells along with anti-CD3 and anti-IgM (or alternatively with specific antigen). Agonists and/or antagonists for TFH surface receptors are also added into cultures. After 7 days antibody production and class switch recombination is assessed by either staining B cells from the culture for activation markers (B7-1, GL7, etc.) or intracellular for IgG isotypes. Activation status of the TFH cell can also be determined.

Alternatively, the supernatants can be assessed for presence of IgGs via ELISA. Examples of this assay are included in FIGS. 4, 20 and 21 of PCT/US2013/069197, hereby incorporated by reference. Similar assays are performed using human cells isolated from blood or other tissues.

In vivo murine TFH stimulation assays are performed by immunizing/vaccinating mice with an antigen/adjuvant. In some cases live or attenuated virus can be used.

Seven to ten days later TFH cells defined as (CD4+ICOS+CXCR5+FoxP3−CD19−) or (CD4+ICOS+CXCR5+GITR−CD19−) (or alternative TFH marker) are sorted by flow cytometry. Cells are either used right away, or incubated in vitro with agonists or antagonists as in in vitro assays. Cells are adoptively transferred intravenously to mice that are vaccinated or likewise challenged with antigen and/or virus. Ten days later serum is collected from mice and IgGs are detected by ELISA. Within these 10 days agonists or antagonists for TFH surface receptors can be administered.

Examples of this assay are in FIGS. 8 and 21 of PCT/US2013/069197, hereby incorporated by reference. These assays can also be used to determine how TFH cells change disease autoimmune pathology. As an example, mice can be immunized with collagen and then TFH cells can be sorted and transferred to a new mouse that is immunized with collagen. The resulting anti-collagen antibodies will cause arthritis which can be measured to determine how TFH cells function within this specific disease. Additionally, these assays can be used to determine TFH stimulation of B cell antibody production in the context of vaccination by using TFH cells from influenza infected mice and then adoptively transfer them to a new mouse that is infected with influenza. Extent of viral infection can be measured as a readout for antibody mediated clearance of virus.

In vitro murine TFR suppression assays are performed by immunizing/vaccinating mice with an antigen/adjuvant. In some cases live or attenuated virus can be used. Seven to ten days later TFH cells defined as (CD4+ICOS+CXCR5+FoxP3−CD19−) or (CD4+ICOS+CXCR5+GITR−CD19−) (or alternative TFH marker) and TFR cells defined as (CD4+ICOS+CXCR5+FoxP3+CD19−) or (CD4+ICOS+CXCR5+GITR+CD19−) (or alternative TFR marker) are sorted by flow cytometry. TFH and/or TFR cells are incubated with B cells along with anti-CD3 and anti-IgM (or alternatively with specific antigen). Agonists and/or antagonists for TFR surface receptors are also added into cultures. After 7 days antibody production and class switch recombination is assessed by either staining B cells from the culture for activation markers (B7-1, GL7, etc.) or intracellular for IgG isotypes. Activation status of the TFH cell can also be determined. Alternatively, the supernatants can be assessed for presence of IgGs via ELISA. Examples of this assay are included in FIGS. 4, 20 and 21 of PCT/US2013/069197, hereby incorporated by reference. Similar assays are performed using human cells isolated from blood or other tissues.

In vivo murine TFR suppression assays are performed by immunizing/vaccinating mice with an antigen/adjuvant. In some cases live or attenuated virus can be used. Seven to ten days later TFH cells defined as (CD4+ICOS+CXCR5+FoxP3+CD19−) or (CD4+ICOS+CXCR5+GITR+CD19−) (or alternative TFH marker) and TFR cells defined as (CD4+ICOS+CXCR5+FoxP3+CD19−) or (CD4+ICOS+CXCR5+GITR+CD19−) (or alternative TFR marker) are sorted by flow cytometry. Cells are either used right away, or incubated in vitro with agonists or antagonists as in in vitro assays. Cells are adoptively transferred intravenously to mice that are vaccinated or likewise challenged with antigen and/or virus. Ten days later serum is collected from mice and IgGs are detected by ELISA. Within these ten days agonists or antagonists for TFR surface receptors can be administered. These assays can also be used to determine how TFR cells change disease pathology. As an example, mice can be immunized with collagen and then TFH and TFR cells can be sorted and transferred to a new mouse that is immunized with collagen. The resulting anti-collagen antibodies will cause arthritis which can be measured to determine how TFR cells function to suppress the TFH mediated disease.

The present invention further provides agents identified in the assays described herein. Such agents are capable of up antagonizing or agonizing a selected TFR receptor and thereby modulate TFR cell-mediated immune function and to further treat diseases as described herein.

Animal model systems which can be used to screen the effectiveness of the selected agents and test agents of the present invention in protecting against or treating the disease are available. Methods for the testing of systemic lupus erythematosus (SLE) in susceptible mice are known in the art (Knight et al. (1978) J. Exp. Med., 147: 1653; Reinersten et al. (1978) New Eng. J. Med., 299: 515). Myasthenia Gravis (MG) is tested in SJL/J female mice by inducing the disease with soluble AchR protein from another species (Lindstrom et al. (1988) Adv. Immunol., 42: 233). Arthritis is induced in a susceptible strain of mice by injection of Type II collagen (Stuart et al. (1984) Ann. Rev. Immunol., 42: 233). A model by which adjuvant arthritis is induced in susceptible rats by injection of mycobacterial heat shock protein has been described (Van Eden et al. (1988) Nature, 331: 171). Thyroiditis is induced in mice by administration of thyroglobulin as described (Maron et al. (1980) J. Exp. Med., 152: 1115). Insulin dependent diabetes mellitus (IDDM) occurs naturally or can be induced in certain strains of mice such as those described by Kanasawa et al. (1984) Diabetologia, 27: 113. EAE in mouse and rat serves as a model for MS in human. In this model, the demyelinating disease is induced by administration of myelin basic protein (see Paterson (1986) Textbook of Immunopathology, Mischer et al., eds., Grune and Stratton, New York, pp. 179-213; McFarlin et al. (1973) Science, 179: 478: and Satoh et al. (1987) J. Immunol., 138: 179).

Generally, suitable agents identified and tested as described above will be used in purified form together with pharmacologically appropriate carriers. Typically, these carriers include aqueous or alcoholic/aqueous solutions, emulsions or suspensions, any including saline and/or buffered media. Parenteral vehicles include sodium chloride solution, Ringer's dextrose, dextrose and sodium chloride and lactated Ringer's. Suitable physiologically-acceptable adjuvants, if necessary to keep, for example, a polypeptide complex such as an antibody in suspension, may be chosen from thickeners such as carboxymethylcellulose, polyvinylpyrrolidone, gelatin and alginates. Intravenous vehicles include fluid and nutrient replenishers and electrolyte replenishers, such as those based on Ringer's dextrose. Preservatives and other additives, such as antimicrobials, antioxidants, chelating agents and inert gases, may also be present (Mack (1982) Remington's Pharmaceutical Sciences, 16th Edition).

The selected agents of the present invention may be used as separately administered compositions or in conjunction with other agents. These can include various immunotherapeutic drugs, such as cylcosporine, methotrexate, adriamycin or cisplatinum, and immunotoxins. Pharmaceutical compositions can include "cocktails" of various cytotoxic or other agents in conjunction with the agents of the present invention.

The route of administration of pharmaceutical compositions according to the invention may be any of those commonly known to those of ordinary skill in the art. For therapy, including without limitation immunotherapy, the selected agents can be administered to any patient in accordance with standard techniques. The administration can be by any appropriate mode, including parenterally, intravenously, intramuscularly, intraperitoneally, transdermally, via the pulmonary route, or also, appropriately, by direct infusion with a catheter. The dosage and frequency of administration will depend on the age, sex and condition of the patient, concurrent administration of other drugs, counterindications and other parameters to be taken into account by the clinician.

In certain therapeutic applications, an adequate amount to accomplish modulation of a TFR and/or TFH cell-mediated immune response will depend upon the severity of the disease and the general state of the patient's own immune system. Generally, if the agent is a blocking antibody, for example, a range from 0.01 mg-100 mg per kilogram of body weight, with doses of 1-10 mg/kg would be suitable.

A composition containing one or more selected agents according to the present invention may be used in prophylactic and therapeutic settings to aid in the modulation of a TFR and/or TFH cell-mediated response. In addition, the agents described herein may be used extracorporeally or in vitro to selectively modulate TFR and/or TFH cell-mediated immune responses.

The invention also provides agents and methods for modulating TFH cell-mediated immune responses. TFH cells are known in the prior art to be a subset of T helper cells that are genetically distinct from other types of T helper cells suggesting that TFH cells contribute to immune responses. This knowledge may be applied to diagnose, monitor and treat, for example, diseases or conditions wherein enhancement of a protective antibody response is therapeutic. Such diseases include but are not limited to treating viral infections and treating cancer. Enhancing and preferably selectively enhancing, TFH cell-mediated immune responses are also particularly beneficial as part of a vaccine or vaccination regimen.

TFH cell function may be modulated by use of an agent such as an agonist or an antagonist of one or more of TFH cell surface receptors as described herein. Use of such an agent in an amount effective to inhibit or induce the differentiation of TFH cells and/or modulate the biological function of TFH cells can affect the TFH cell-mediated immune response.

In one embodiment, the invention provides method of increasing a protective antibody response in a patient in need thereof comprising administering to the patient, an agent which modulates at least one receptor which is differentially expressed on TFH cells as compared to TFR cells at an increased mean fluorescence intensity (MFI) fold change of at least 1.17, and wherein the receptor has an MFI of at least 200 on TFH cells and wherein the agent is effective to modulate the receptor and increase the antibody response in the patient as compared to the antibody response when the agent is absent. Such differentially expressed receptors are referred to herein as "selective TFH receptors". In one embodiment at least one selective TFH receptor is selected from one or more of: CD163, CD127, CD8a, CD89, CD197, CD161, CD6, CD229, CD96, CD272, CD148, CD107a, CD100, CD82, CD126, CD45RO, PD-1 (CD279), CD5, and CD99. In one embodiment, at least one selective TFH receptor is selected from one or more of: CD163, CD127, CD161, CD6, CD229, CD272, CD100, CD126, PD-1 (CD279).

In one embodiment, the agent is a blocking/antagonizing antibody capable of blocking a selective TFH receptor, or binding to the ligand of the receptor and thereby blocking its ability to bind its corresponding receptor. The agent may also be a small molecule, or a DNA or RNA molecule (e.g. dsRNA, or antisense molecule) capable of antagonizing or agonizing the receptor.

In addition to the known agonists and antagonists the various selective TFH receptors described herein, other agents may be tested for their ability to antagonize or agonize selective TFH receptors using known assays and screens. Assays and screens for testing various agents for their ability to agonize or antagonize TFH cell surface receptors are described previously herein. Animal models may be used to test modulation of selective TFH receptors as described previously herein.

The present invention further provides agents identified in the assays described herein wherein such agents are capable of antagonizing or agonizing a selective TFH receptor and thereby modulate TFH cell-mediated immune function. Agents for modulating selective TFH receptors may be formulated and administered to patients as described above.

In one embodiment, the invention provides a method of decreasing a pathogenic antibody response in a patient in need thereof comprising administering to the patient a first agent capable of modulating a selective TFR receptor in an amount effective to increase TFR cell-mediated antibody suppression in the patient, alone or in combination with an second agent capable of modulating a selective TFH receptor in an amount effective to decrease TFH cell-mediated antibody production, wherein the pathogenic antibody response is decreased as compared to the pathogenic antibody response in the absence of the first or second agents.

In one embodiment, the invention provides a method of increasing a protective antibody response in a patient in need thereof comprising administering to the patient a first agent capable of modulating a selective TFR receptor in an amount effective to decrease TFR cell-mediated antibody suppression in the patient, alone or in combination with a second agent capable of modulating a selective TFH receptor in an amount effective to increase TFH cell-mediated antibody production, wherein the protective antibody response is increased as compared to the protective antibody response in the absence of the first or second agents.

VIII. Modulation of TFR and TFH Cell-Mediated Immune Responses Via PD-1 Receptors The inventors' discovery that PD-1:PD-L1 interactions limit TFR cell differentiation and function has also elucidated another novel approach to modulating both TFR cell-mediated and TFH cell-mediated immune responses in a patient.

Therefore, in one embodiment the invention provides a method of decreasing a pathogenic antibody response in a patient in need thereof comprising administering to the patient, an agent which modulates the PD-1 receptor on a TFR cell. In one embodiment, the agent is an antagonist of the PD-1 receptor on a TFR cell. In one embodiment, the agent is an antibody capable of blocking the PD-1 receptor on a TFR cell. In one embodiment, the agent is an antibody capable of binding to a ligand selected from PD-L1 or PD-L2 and preventing the ligand from binding to the PD-1 receptor. The agent may also be a small molecule, or a DNA or RNA molecule (e.g., dsRNA, or antisense molecule) capable of antagonizing or agonizing the receptor.

In one embodiment a disease or condition wherein suppression of a pathogenic antibody response is therapeutic includes those diseases listed previously in which antibodies contribute to, or are primarily responsible for pathogenesis.

In another embodiment, the invention provides a method of increasing a protective antibody response in a patient in need thereof comprising administering to the patient, an agent which modulates the PD-1 receptor on a TFH cell. In one embodiment the agent is an agonist of the PD-1 receptor on a TFH cell. The agent may also be a small molecule, or a DNA or RNA molecule (e.g. dsRNA, or antisense molecule) capable of agonizing the PD-1 receptor.

In one embodiment, the invention provides a method of decreasing a pathogenic antibody response in a patient in need thereof comprising administering to the patient a first agent capable of modulating a PD-1 receptor on a TFR cell in an amount effective to increase TFR cell-mediated antibody suppression in the patient, in combination with an second agent capable of modulating a PD-1 receptor on a TFH cell in an amount effective to decrease TFH cell-mediated antibody production, wherein the pathogenic antibody response is decreased as compared to the pathogenic antibody response in the absence of the first or second agents.

In one embodiment, the invention provides a method of increasing a protective antibody response in a patient in need thereof comprising administering to the patient a first agent capable of modulating a PD-1 receptor on a TFR cell in an amount effective to decrease TFR cell-mediated antibody suppression in the patient, in combination with a second agent capable of modulating a PD-1 receptor on a TFH receptor in an amount effective to increase TFH cell-mediated antibody production, wherein the protective antibody response is increased as compared to the protective antibody response in the absence of the first or second agents.

In addition to the known agonists and antagonists of the PD1 receptor generally, other agents may be tested for their ability to antagonize or agonize PD-1 on TFH and TFR cells using known assays and screens. Assays and screens for testing various agents for their ability to agonize or antagonize PD-1 receptors are previously described. Animal models may be used to test modulation of selective TFH receptors as described above.

The present invention further provides agents identified in the assays described herein wherein such agents are capable of antagonizing or agonizing PD-1 receptors and thereby modulate TFR or TFH cell-mediated immune function or both.

Agents for modulating PD-1 receptors on TFR or TFH cells may be formulated and administered to patients as described above.

The following examples are intended to promote a further understanding of the disclosure. While the disclosure is described herein, with reference to illustrated embodiments, it should be understood that the disclosure is not limited hereto. Those having ordinary skill in the art and access to the teachings herein will recognize additional modifications and embodiments within the scope thereof. Therefore, the disclosure is limited only by the claims attached herein.

EXAMPLES

Aspects and exemplifications relating to the 1) PD-1 Controls T Follicular Regulatory Cells; 2) PD-1 Deficient TFR cells are Capable of Homing to Germinal Center; 3) PD-1 deficient TFR cells More Potently Inhibit T Cell Activation; 4) PD-1 Controls Blood T Follicular Regulatory Cells; 5) Blood TFH and TFR cells require CD28 and ICOS Signals; 6) PD-1 deficient blood TFR cells more potently regulate antibody production in vivo; 7) T Follicular Regulatory cell (TFR) Cellular Therapy Strategies; 8) Differentiation of Circulating TFH and TFR cells Require Priming by Dendritic Cells; 9) Blood TFH and TFR Cells Exit the Lymph Node via S1P Signals; 10) Circulating TFH and TFR cells Migrate to Diverse Lymph Nodes and Tissues; 11) Circulating TFH and TFR cells are More Potently Activated After Transfer in vivo; 12) Circulating TFH cells Require Dendritic Cells for Restimulation and Have Memory Properties; 13) TFR cells Potently Suppress T Cell and B Cell Activation; 14) Weaker B cell Suppression by Blood TFR cells; 15) Comparison of TFR and Treg gene expression signatures; 16) Surface receptors differentially expressed by human blood TFR cells; 17) Surface receptors differentially expressed by human blood TFH cells; and 18) Blockade of the PD-1 pathway can heighten antibody stimulating capacity of TFH cells are provided in Ser. No. 14/707,596, PCT/US2013/069197, filed Nov. 8, 2013, and U.S. provisional application No. 61/724,424, filed Nov. 9, 2012, and are hereby incorporated by reference in there entirety.

Example 1—B Cells Suppressed by TFR Cells Undergo Early Activation

To determine the mechanisms of how TFH and B cells are altered during direct TFR suppression, an in vitro suppression assay in which TFR cells are cultured with TFH and B cells was utilized. See e.g., Sage et al., J Clin Invest 124, 5191-5204 (2014); Sage et al., Immunity 41, 1026-1039 (2014); Sage et al., Methods Mol Biol 1291, 151-160 (2015). For these assays, FoxP3IRES-GFP mice were immunized with NP-OVA (emulsified in CFA) subcutaneously and isolated draining lymph nodes 7 days later. TFR (sorted as CD4+ICOS+CXCR5+CD19− FoxP3+) cells were added to co-cultures of B (sorted as CD19+) and TFH (sorted as CD4+ICOS+CXCR5+CD19−FoxP3) cells along with anti-CD3 and anti-IgM for 2 to 6 days (FIG. 1A, FIG. 36A, and FIG. 36B). After 6 days of co-culture of B and TFH cells, robust upregulation of the GC B cell marker GL7 was found as well as class switch recombination to IgG1, the predominant class switched isotype in this model (FIG. 1B). In addition, robust quantities of secreted IgG were found in the culture supernatant when B cells were cultured with TFH cells, but not when B cells were cultured alone. However when TFR cells were added to B and TFH cultures, class switch recombination, GL7 expression and secretion of antibody was severely diminished, demonstrating that TFR cells potently suppress B cell effector functions. CD4+ CXCR5−ICOS−Foxp3+ Treg cells were not able to suppress as efficiently as TFR cells did (FIG. 15). TFR cells also suppressed CSR of B cells in response to specific antigen (FIG. 36C). Furthermore, the suppression of CSR by TFR cells required cell contact, as supernatant from TFR cultures did not suppress B cells (FIG. 16). Time-lapse microscopy of cultures revealed that TFR cells closely interacted with both TFH cells and B cells (FIG. 17). These data suggested that TFR cells might physically disrupt TFH cell- and B cell-linked recognition during suppression. Therefore, this culture system is a robust model to study TFR suppression of TFH and B cells.

Figure 1C:
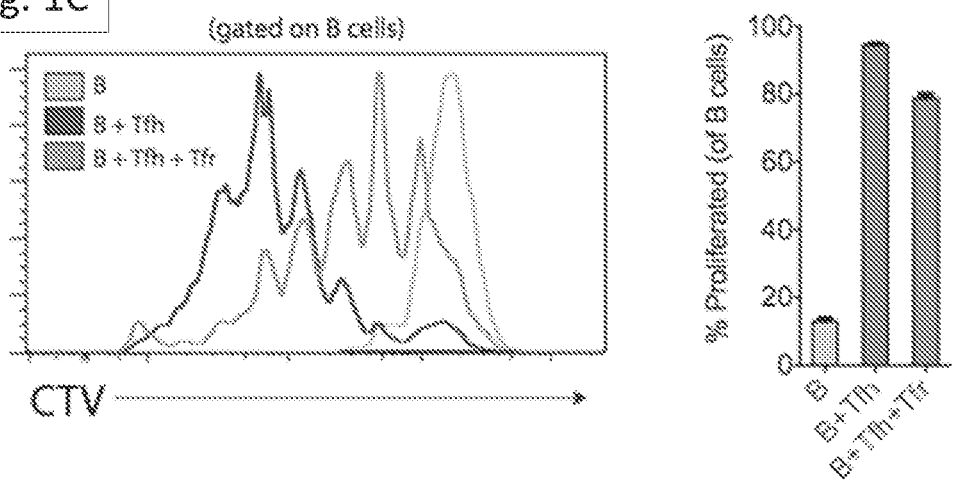
Figure 1D:
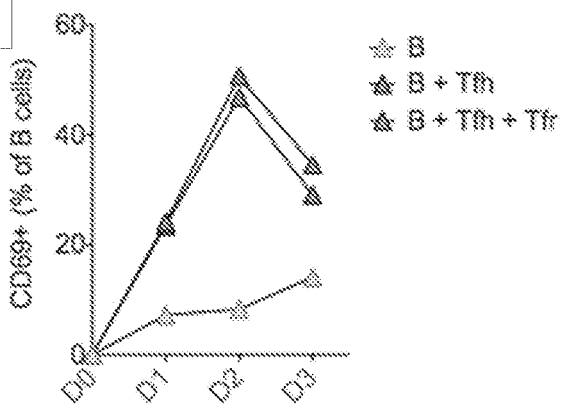

Next, it was determined whether TFR suppression of B cells results in a total lack of B cell activation, or if suppression is more targeted to downstream effector functions. Similar in vitro suppression assays were performed except B cells were labeled with a cell trace violet (CTV) proliferation dye. When B cell proliferation (by assessing CTV dilution) was analyzed after co-culture with or without TFR cells, it was found that despite a decrease the numbers of cell divisions, the vast majority of B cells had proliferated at least one cell cycle when TFR cells were present (FIG. 1C). Therefore, TFR cells suppression does not completely prevent proliferation of B cells in co-cultures of only TFR cells and B cells (without TFH cells) and lipopolysaccharide plus IL-4 (FIG. 18). To determine if early activation of B cells was affected by TFR cells, CD69 expression on B cells during the first few days of co-culture was analyzed. Surprisingly, CD69 was upregulated in B cells whether or not suppressive TFR cells were present within the first three days of culture, demonstrating that early activation of B cells still occurs during TFR cell suppression (FIG. 1D). Therefore, although TFR cells inhibit proliferation and effector functions of B cells, the suppressed B cells show evidence of some activation and proliferation.

Figure 1E:
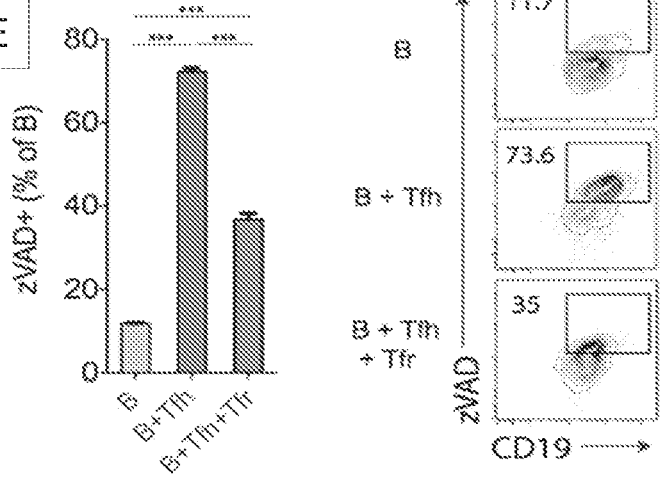
Figure 1F:
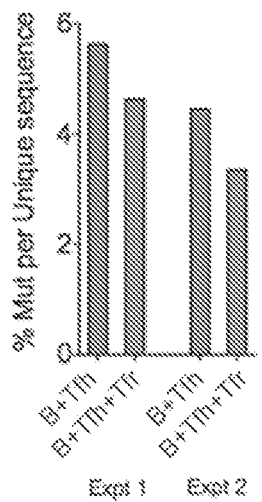

One possible explanation for defective effector functions of B cells during TFR suppression is that TFR cells may be inducing cell death in B cells. Therefore, cell death was assessed through staining B cells with the active caspase reagent, zVAD. In these co-culture experiments TFH cells induce cell death in B cells which is consistent with high amounts of cell death within germinal centers during affinity maturation in vivo (FIG. 1E). However, when TFR cells were present, cell death was dramatically decreased in B cells which suggests that TFR cells do not alter B cell responses through sensitizing B cells to undergo apoptosis. Affinity maturation of B cells in GCs occurs through a balance between somatic hypermutation and cell death. To determine if TFR cells can alter somatic hypermutation, in vitro suppression assays were performed and added specific antigen (NP-OVA) (instead of anti-CD3 and anti-IgM) to facilitate the testing of mutated B cell receptors in culture. B cells were sorted after 6 days of culture and sequenced the B cell receptor heavy chain and analyzed somatic hypermutation. A moderately low frequency of mutations per unique VDJ sequence in cultures of B cells with TFH cells was found (FIG. 1F). TFR cells (but not Treg cells) also suppressed the activation of TFH cells, as indicated by reduced expression of Bcl6 and the proliferation marker Ki67 (FIG. 19). However, when TFR cells were added, fewer mutations per unique VDJ sequence were found which demonstrates that TFR cells can suppress somatic hypermutation of B cells. Taken together, these data demonstrate the in vitro suppression assay robustly measures TFR suppression of B cells and that this suppression allows B cells to receive some activation signals.

Figure 2A:
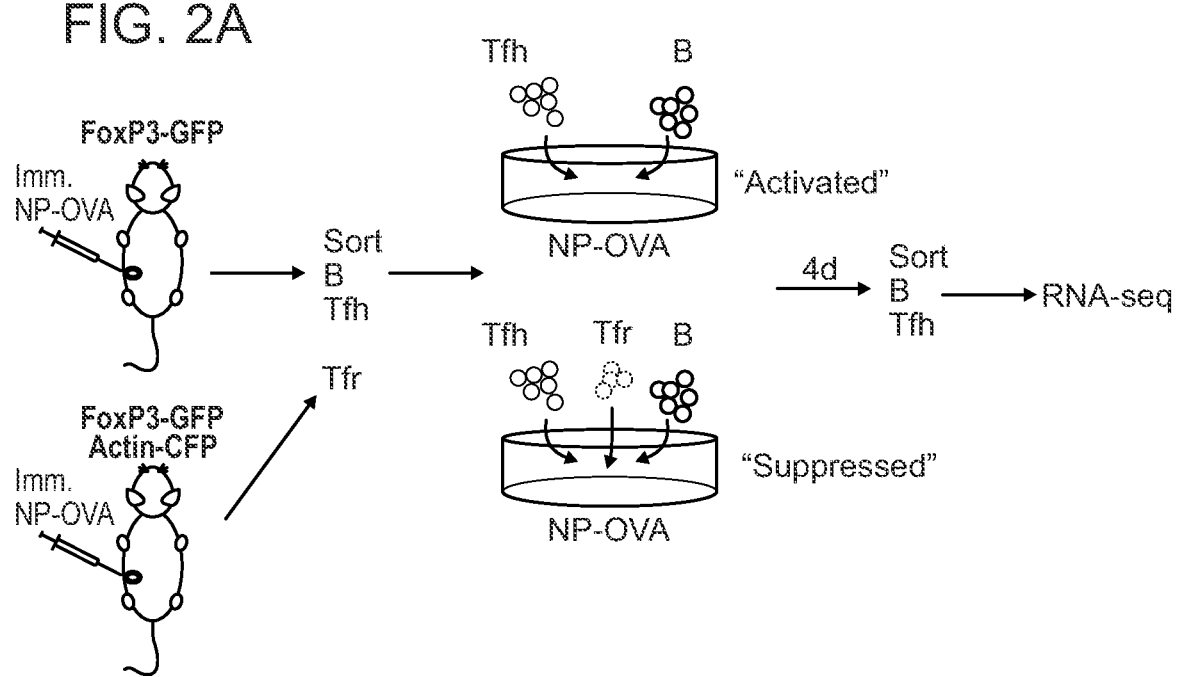
FIG. 2A-FIG. 2H show that suppressed TFH and B cells resemble effector populations except for downregulation of key effector genes.

Example 2—Suppressed B and TFH Cells Downregulate a Small Subset of Effector Genes but Still Resemble Effector Cells These findings suggested that TFR cells suppress B cells in a way that allows the B cell to receive some activation signals, yet is unable to perform effector functions such as class switch recombination, somatic hypermutation or antibody secretion. In order to determine how B and TFH cells effector states are altered during TFR mediated suppression assays were performed followed by RNA-seq transcriptome analysis. In these experiments B and TFH cells (from immunized FoxP3-IRES-GFP mice) were cultured with or without TFR cells (from immunized ActinCFP FoxP3-IRES-GFP mice) for 6 days in the presence of NP-OVA (the same antigen used to generate the B, TFH and TFR cells). After 4 days of culture, B (sorted as CD19+IA+CD4−) and TFH (sorted as CD4+IA−CD19−CFP−) cells were sorted from the "activated" culture (TFH and B cells alone) or from the "suppressed" culture (TFH, B and TFR cells) and RNAseq transcriptional analysis was performed (FIG. 2A, FIG. 37A and FIG. 37B).

Figure 2B:
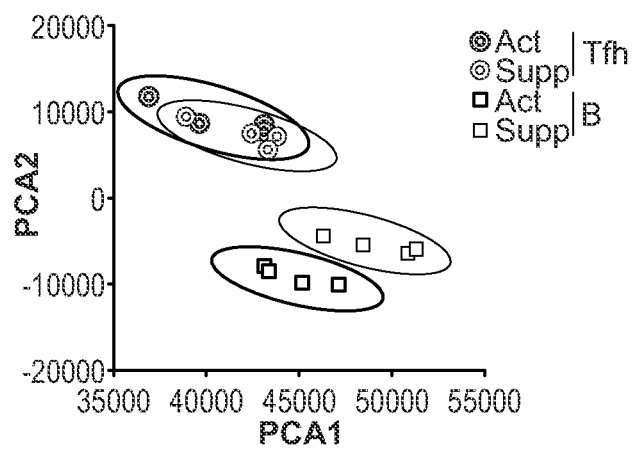
Figure 2C:
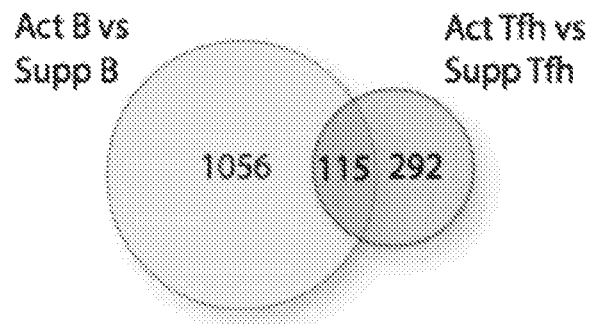
Figure 2D:
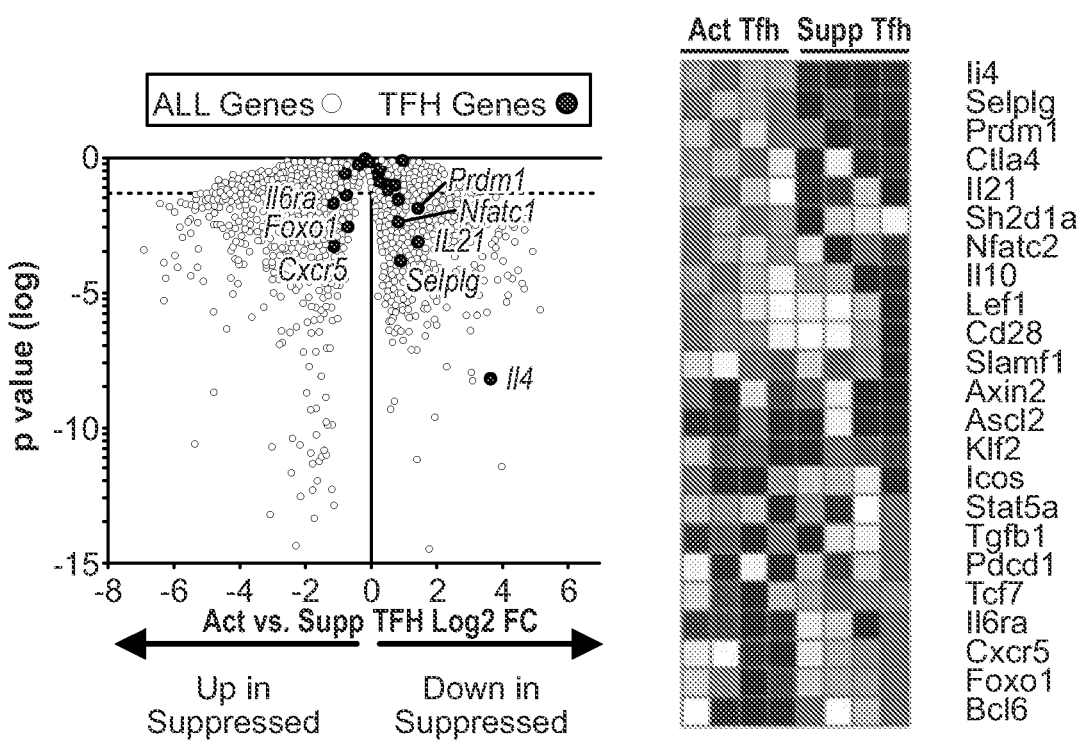

By principle component analysis (PCA), slight separation of activated and suppressed B cells was found, but not activated or suppressed TFH cells (FIG. 2B). TFH and B cell populations separated as expected since these are distinct lineage cells. 1171 genes were found that were differentially expressed (FDR adjusted p value<0.05) between activated and suppressed B cells, but only 407 genes that were differentially expressed between activated and suppressed TFH cells (FIG. 2C, and FIG. 37C-FIG. 37F). Therefore, TFR suppression elicits more transcriptional changes in B cells than in TFH cells.

Figure 2E:
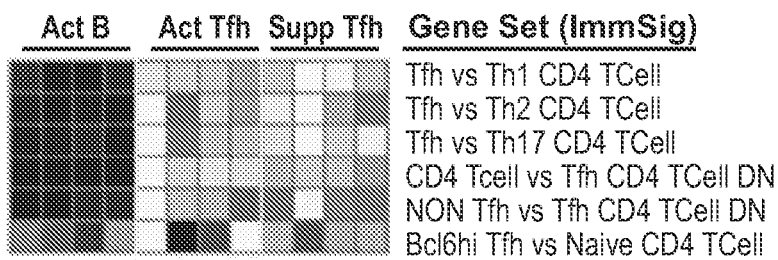

Next, whether TFR suppression affects TFH cell identity and function was determined. To do this, a list of TFH genes that regulate TFH cell differentiation/function was compiled and differences between activated or suppressed TFH cells were analyzed. Surprisingly, no downregulation of TFH transcription factors such as Bcl6 or Ascl2 associated with suppression was found (FIG. 2E). However, both IL-4 and IL-21 transcripts were potently downregulated in TFH cells during TFR suppression. This data suggests that after TFR mediated suppression, TFH cells still retain their TFH program, but have downregulation of key effector molecules. To confirm that suppressed TFH cells still retained a TFH-like transcriptional program, single sample gene set enrichment analysis (ssGSEA) was performed in which transcriptional states between activated and suppressed TFH cells was compared with published transcriptional signatures of TFH cells (from the Broad immSig C7 collection).

It was found that suppressed TFH cells qualitatively still retained their TFH-like transcriptional signature suggesting that these cells are not being converted to a different cell type during suppression and still have a TFH-like program.

Figure 2F:
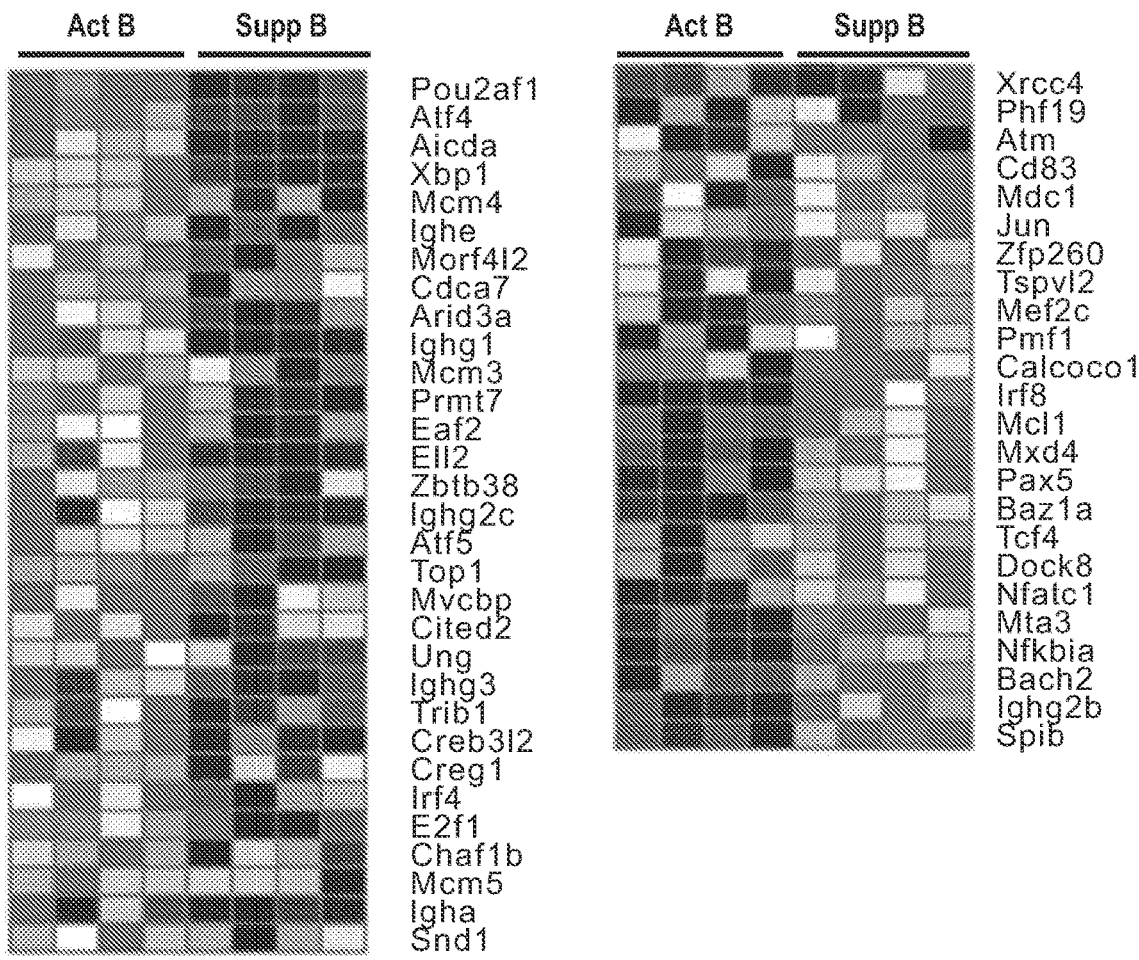
Figure 2G:
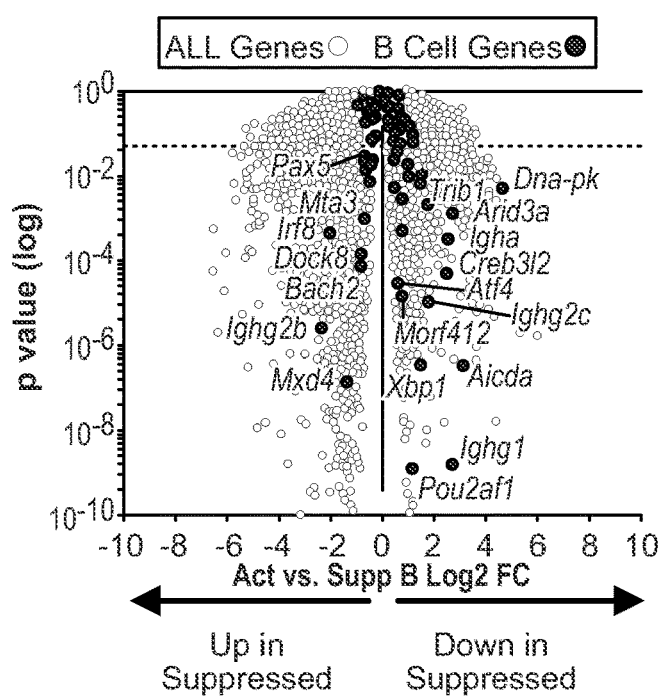

Next whether B cells, similar to TFH cells, retain their effector program during TFR cell suppression was determined. When B cell effector genes (from a curated list) in activated or suppressed B cells were compared, lower expression of transcripts was found for antibody isotypes including Ighg1 (IgG1, the dominant IgG isotype in these assays), Ighg2c and Igha (FIG. 2F-FIG. 2G). Ighg2b transcripts were upregulated upon suppression, however IgG2b was not increased by ELISA measurements in these assays. Three of the most downregulated transcripts in B cells upon TFR suppression were Pou2af1 (which encodes a transcription factor that is essential for GC B cell formation), Xbp1 (which encodes a regulator of protein folding and ER stress which is important for secretion of antibody by plasma cells) and Aicda (which encodes AID, an enzyme responsible for initiation of class switch recombination). Despite these dramatic changes in genes important for GC/plasma cell function, most other B cell effector genes were not changed in expression.

Figure 2H:
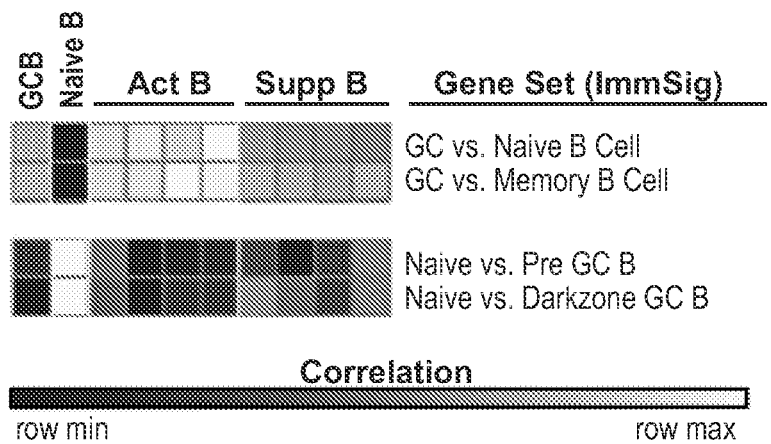
Figure 3:
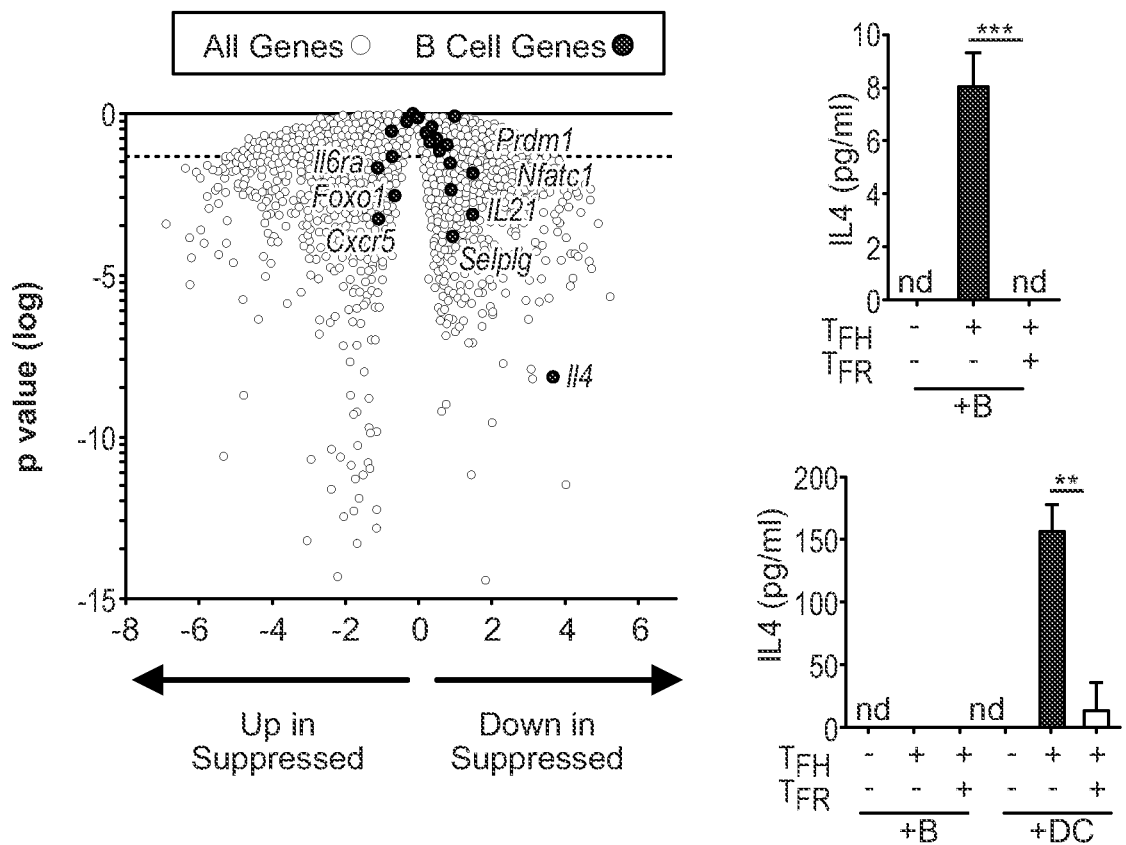
FIG. 3 shows that suppressed TFH cells have defective cytokine production but still express TFH program.

To determine if suppressed B cells still maintained an activated GC B cell transcriptional signature despite changes in a small subset of effector genes, ssGSEA analysis was performed. When the activated and suppressed B cells (along with GC B or naïve B sorted from immunized mice) were compared, it was found that suppressed B cells still mostly maintained their GC signature (FIG. 2H). Therefore, although suppressed TFH and B cells demonstrate downregulation of genes encoding effector molecules (IL-4 and IL-21 in TFH, and IgG1, Xbp1, Pou2af1 and AID in B cells), these cells still maintain a transcriptional signature similar to effector cells. Taken together, these data indicate that TFR cells allow B and TFH cells to maintain an activated transcriptional signature during suppression but downregulate key effector molecules that are important for downstream effector function, suggesting that TFR suppression is targeted to specific molecules.

To determine if any non-effector subset related pathways were altered in B and TFH cells during suppression basic GSEA was performed utilizing the hallmarks, gene ontology and transcription factor gene sets from the Broad Institute. It was found that activated B cells showed strong enrichment of gene sets for Myc targets, MTORc1 signaling, oxidative phosphorylation and glycolysis compared to suppressed B cells (Table 1). Activated TFH cells also showed enrichment of E2F targets, glycolysis and MTORc1 signaling compared to suppressed TFH cells, however this enrichment was not as strong as in B cells. Few gene sets were detected that enriched in suppressed B cells compared to activated B cells, with the exception of interferon alpha response and G protein signaling coupled to cAMP.

TABLE 1

| Collection | Gene Set | Size | NES | FDR q-val |
|---|---|---|---|---|
| Enriched in Act B vs. Supp B | | | | |
| Hall (50) | HALLMARK_MYC_TARGETS_V1 | 196 | 2.7671254 | <0.0001 |
| | HALLMARK_MYC_TARGETS_V2 | 58 | 2.3868976 | <0.0001 |
| | HALLMARK_MTORC1_SIGNALING | 192 | 2.346688 | <0.0001 |
| | HALLMARK_E2F_TARGETS | 193 | 2.2503338 | <0.0001 |
| | HALLMARK_OXIDATIVE_PHOSPHORYLATION | 191 | 2.1517582 | <0.0001 |
| | HALLMARK_UNFOLDED_PROTEIN_RESPONSE | 111 | 2.1171036 | <0.0001 |

TABLE 1-continued

| Collection | Gene Set | Size | NES | FDR q-val |
|---|---|---|---|---|
| | HALLMARK_GLYCOLYSIS | 192 | 1.8493669 | 0.00031 |
| | HALLMARK_G2M_CHECKPOINT | 196 | 1.6099535 | 0.00383 |
| | HALLMARK_DNA_REPAIR | 138 | 1.505335 | 0.01441 |
| | HALLMARK_FATTY_ACID_METABOLISM | 147 | 1.500412 | 0.01398 |
| GO (1011) | NUCLEOLUS | 110 | 2.0671701 | 0.00094 |
| | MITOCHONDRION | 319 | 2.06659 | 0.00047 |
| | MITOCHONDRIAL_PART | 138 | 2.0225444 | 0.00129 |
| | RIBONUCLEOPROTEIN_COMPLEX | 142 | 1.9865174 | 0.00264 |
| | RIBONUCLEOPROTEIN_COMPLEX_BIOGENESIS_AND_ASSEMBLY | 81 | 1.9715921 | 0.00249 |
| | PROTEASOME_COMPLEX | 22 | 1.9145986 | 0.00636 |
| | RNA_SPLICING | 89 | 1.9071435 | 0.00599 |
| | TRANSLATION_INITIATION_FACTOR_ACTIVITY | 21 | 1.8895354 | 0.00679 |
| | RNA_PROCESSING | 166 | 1.883764 | 0.00656 |
| | RIBOSOME_BIOGENESIS_AND_ASSEMBLY | 18 | 1.8799101 | 0.00648 |
| | ISOMERASE_ACTIVITY | 35 | 1.8725868 | 0.00701 |
| | NUCLEOLAR_PART | 18 | 1.8698697 | 0.00651 |
| | MITOCHONDRIAL_MATRIX | 45 | 1.8656288 | 0.00660 |
| | MITOCHONDRIAL_LUMEN | 45 | 1.8638681 | 0.00626 |
| TF (773) | V$MYC_Q2 | 169 | 1.7301639 | 0.02973 |
| | SGCGSSAAA_V$E2F1DP2_01 | 153 | 1.6884224 | 0.02908 |
| | V$E2F1_Q3 | 219 | 1.683651 | 0.01995 |
| | V$E2F_Q5 | 214 | 1.6622303 | 0.02027 |
| | V$E2F4DP1_01 | 216 | 1.6378138 | 0.02317 |
| | V$E2F1_Q6 | 214 | 1.6301547 | 0.02114 |
| | V$MYCMAX_01 | 230 | 1.6162086 | 0.02279 |
| | Enriched in Act Tfh vs. Supp Tfh | | | |
| Hall (50) | HALLMARK_E2F_TARGETS | 193 | 1.9549149 | <0.0001 |
| | HALLMARK_HYPOXIA | 193 | 1.8284913 | 0.00152449 |
| | HALLMARK_G2M_CHECKPOINT | 196 | 1.7426534 | 0.00319641 |
| | HALLMARK_GLYCOLYSIS | 192 | 1.7223264 | 0.00311881 |
| | HALLMARK_MTORC1_SIGNALING | 192 | 1.709111 | 0.00276171 |

Example 3—TFR Suppression Alters the Myc and MTOR Pathways in B Cells

Figure 5A:
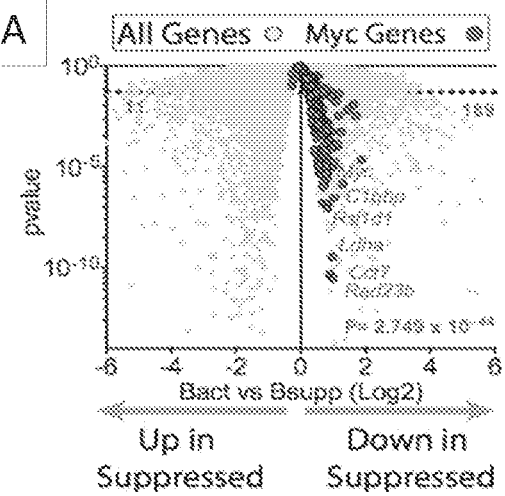
FIG. 5A-FIG. 5E show inhibition of c-MYC inhibits B cells similarly to TFR Cells.
Figure 5B:
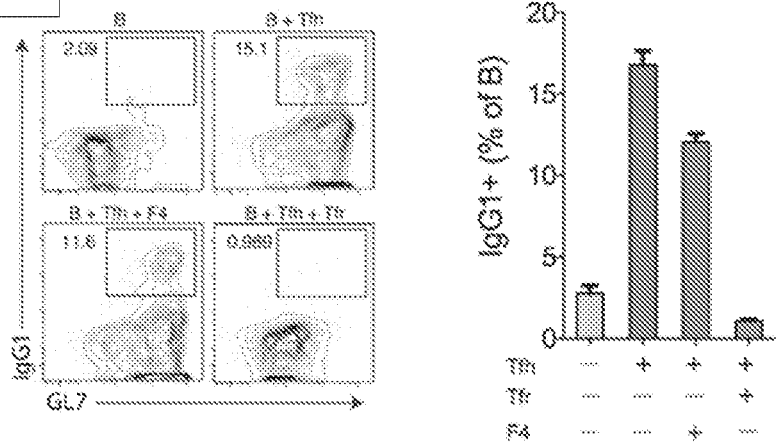
Figure 5C:
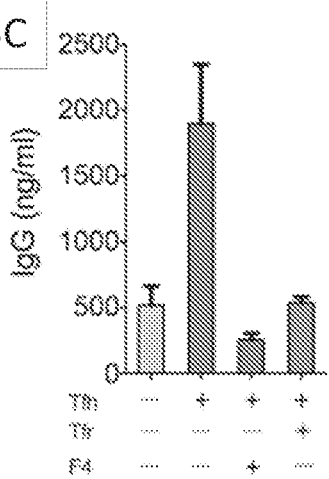

Whether Myc pathway genes were altered in B cells upon TFR suppression was determined since it was one of the most downregulated gene sets in suppressed B cells. Almost all Myc target genes in B cells showed evidence of downregulation at the transcriptional level during TFR suppression (FIG. 5A). To determine if suppressing Myc in activated B cells could recapitulate TFR suppression, in vitro suppression assays were performed in which B cells were cultured with TFH cells, TFH and TFR cells, or TFH cells and the Myc inhibitor 10058-F4 (F4w). In these assays, TFH cells stimulated robust class switch recombination to IgG1 which was almost completely suppressed by the addition of TFR cells (FIG. 5B). Addition of the Myc inhibitor to the activated culture (B+ TFH) resulted in a slight diminishment of class switch recombination. When the culture supernatants from these experiments were analyzed, it was found that the Myc inhibitor robustly attenuated the amount of secreted antibody even greater than TFR cells (FIG. 5C). Therefore, inhibiting the Myc pathway results in suppression of class switch recombination and antibody secretion.

Figure 5D:
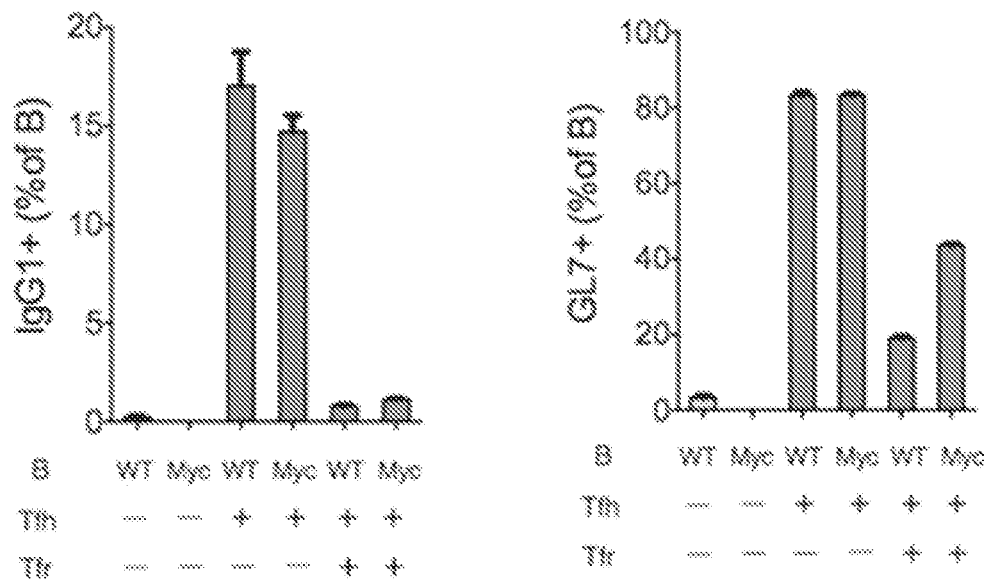
Figure 5E:
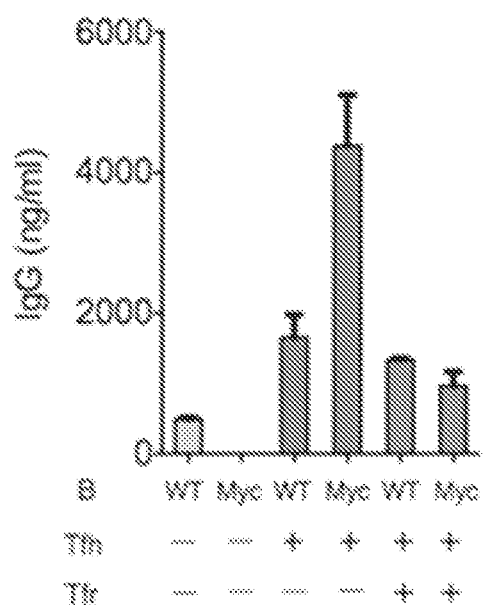

Since the Myc pathway may be a key pathway in B cells that is modulated during TFR suppression, whether overexpression of Myc could cause B cells to become resistant to TFR suppression was determined. WT or Igh-Myc (i.e. Eμ-Myc, Myc overexpressing) mice were cultured with TFH and TFR cells. Interestingly, Myc overexpression did not result in rescue of class switch recombination nor secreted antibody (FIG. 5D and FIG. 5E). However, GL7 expression in B cells was partially rescued in conditions of Myc overexpression, suggesting that Myc overexpression can prevent some suppression by TFR cells, although this may be minor. Taken together, these data demonstrate that TFR cells suppress the Myc pathway in B cells which may be partially responsible for defective antibody production.

Figure 6F:
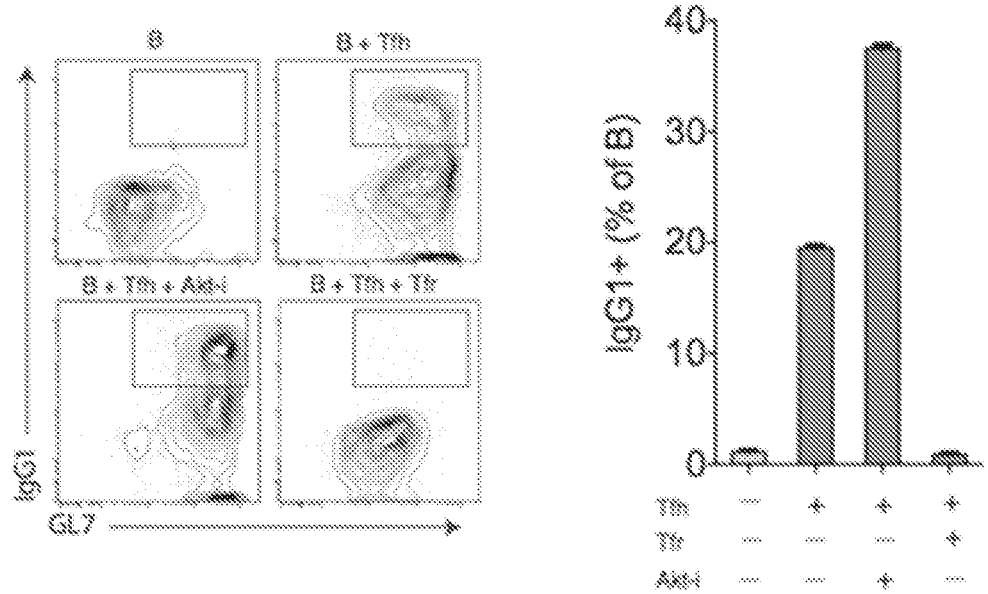
Figure 6G:
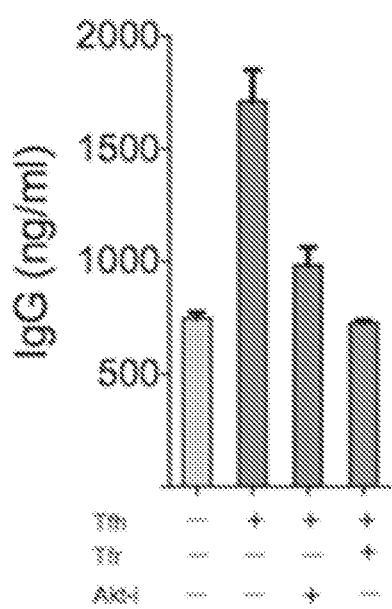

The mTOR pathway promotes protein synthesis during activation and has been linked to enhancing cellular metabolism. Since evidence of the mTORc1 pathway being downregulated at the transcript level in both B and TFH cells during TFR suppression (FIG. 4A) was found, whether blocking the mTOR pathway could lead to suppression of antibody production was determined. In vitro cultures of B and TFH cells were performed along with either the mTORc1 inhibitor rapamycin or TFR cells. Addition of rapamycin to cultures resulted in severely diminished class switch recombination as well as antibody production in similar magnitude as addition of TFR cells (FIG. 6B and FIG. 6C). Similar results were also obtained when the mTORc1/mTORc2 inhibitor PP242 was used (FIG. 6D and FIG. 6E). Therefore, inhibiting the mTOR pathway results in suppression of class switch recombination and antibody production, similar to TFR cells. Akt can act both upstream and downstream of mTOR to mediate activation signaling. When Akt was inhibited with an Akt1/2 inhibitor in the B and T cell cocultures, it was found that inhibiting Akt surprisingly caused an increase in class switch recombination (FIG. 6F). However, Akt inhibition resulted in diminishment of antibody secretion in coculture experiments. Taken together, these data indicate that suppressing the PI3K/Akt/mTOR pathway can result in suppression of TFH-mediated B cell antibody production with a similar magnitude and features of TFR mediated suppression.

Example 4—TFR Cells Suppress B Cell Metabolism

Figure 7A:
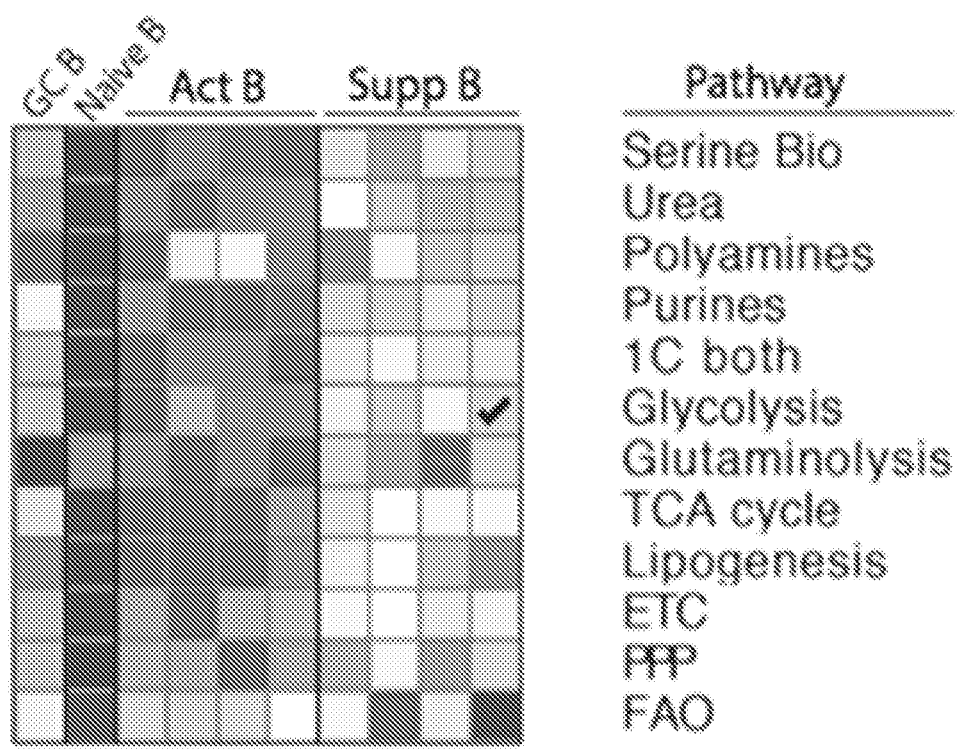
FIG. 7A-FIG. 7J show TFR cells inhibit multiple metabolic pathways in B cells.
Figure 7B:
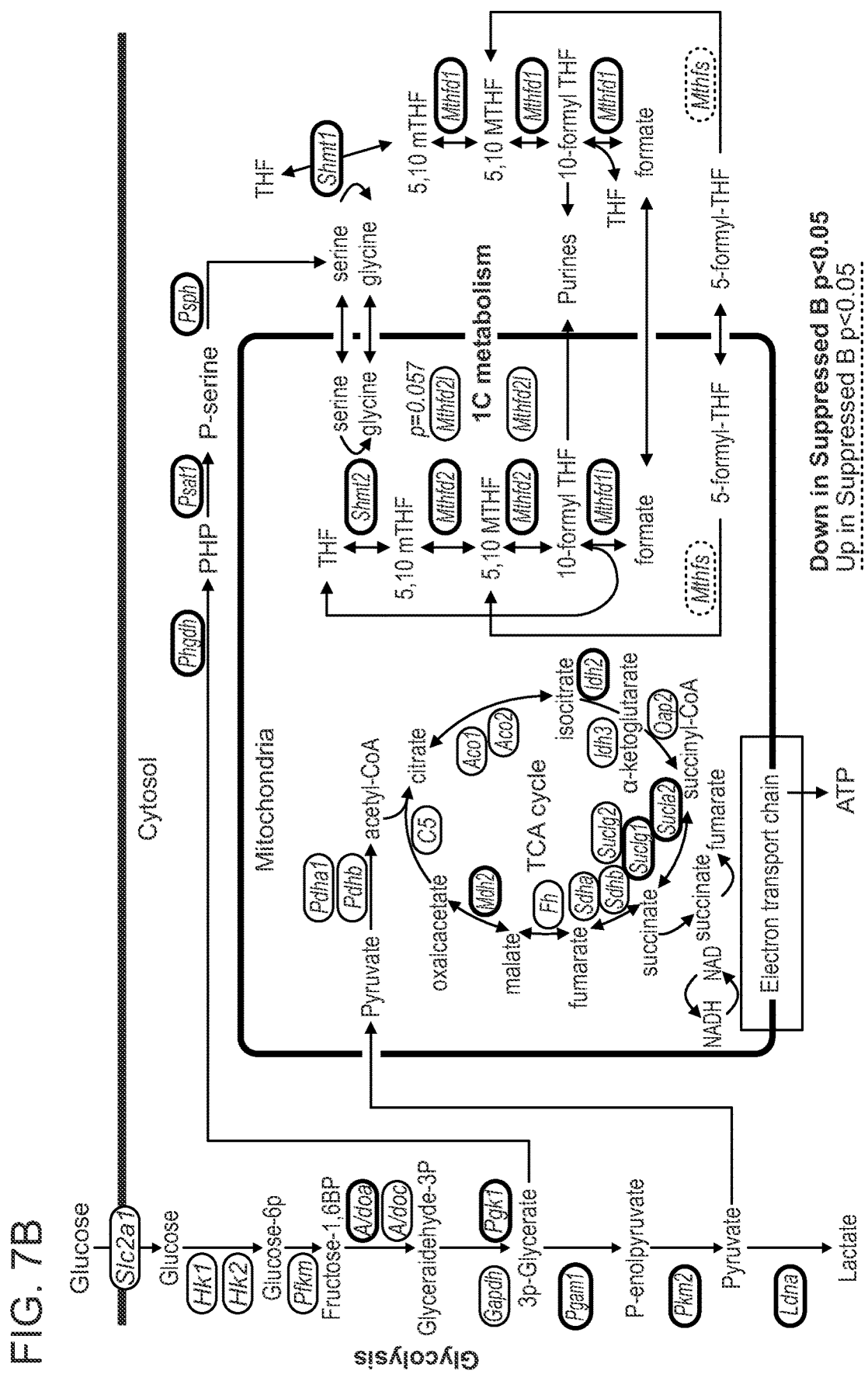

Whether TFR suppression of B and TFH cells resulted in altered metabolism was determined since the GSEA analysis demonstrated downregulation of genes associated with glycolysis, oxidative phosphorylation, Myc and mTOR pathways. First a general comparison of metabolic pathways using RNA-seq data was performed comparing activated or suppressed B cells (generated in FIG. 2A-FIG. 2H) by averaging expression values of genes encoding key enzymes within individual pathways. Evidence of downregulation of a number of metabolic pathways was found including serine biogenesis, purine metabolism, 1-carbon metabolism, TCA cycle, electron transport chain (which is involved in oxidative phosphorylation) and glycolysis (FIG. 7A). The only pathway that gave any indication of being increased in B cells upon suppression was fatty acid oxidation. Nevertheless, this data suggests that a number of metabolic pathways are downregulated in B cells upon TFR suppression. To better visualize the complex interactions of a subset of these pathways, a metabolic map of key intermediates in glycolysis, serine metabolism, 1-carbon metabolism, purine metabolism and the TCA cycle was made. A number of key enzymes were found within these pathways including enzymes that affect multiple pathways (FIG. 7B). Therefore, instead of TFR cells suppressing one single metabolic pathway, this data suggests that TFR cells attenuate many different metabolic pathways as a part of suppression The effects of suppression by TFR cells on glycolysis was assessed, since this pathway is essential for antibody production. First expression of the glucose transporter Glut1 in B cells suppressed by TFR cells was compared. TFR cells (but not Treg cells) suppressed Glut1 expression in B cells (FIG. 20), which suggested that the TFR cells suppressed B cell glycolysis. The suppression of Glut1 expression (and CSR) in B cells by TFR cells was not due to an increase in the abundance of non-dividing cells (which have low expression of Glut1), because comparison of B cells that had undergone the same number of cell divisions revealed diminished Glut1 expression and CSR in the suppressed B cells (FIG. 21 and FIG. 39A-FIG. 39E). In addition, the suppression of CSR and metabolism by TFR cells occurred before the changes in B cell proliferation; when B cells were analyzed that had been added to activated or suppressed cultures and harvested 20 h later (before the first cell division), B cells in suppressed cultures had lower expression of Glut1 and IgG1 than that of B cells in activated cultures (FIG. 22 and FIG. 39A-FIG. 39E). These studies indicated a decoupling of CSR and metabolism from proliferation and demonstrated that the suppression of CSR and metabolism in B cells by TFR cells could occur independently of changes in proliferation. TFR cells (but not Treg cells) also caused lower expression of Glut1 in TFH cells (FIG. 23).

Figure 7C:
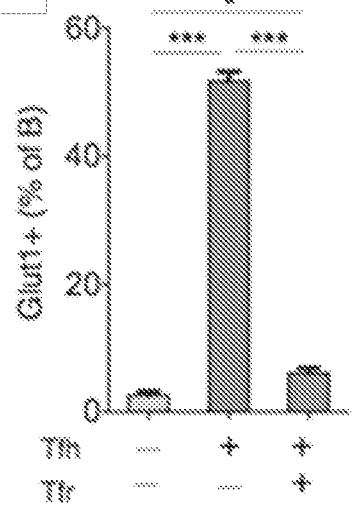
Figure 7D:
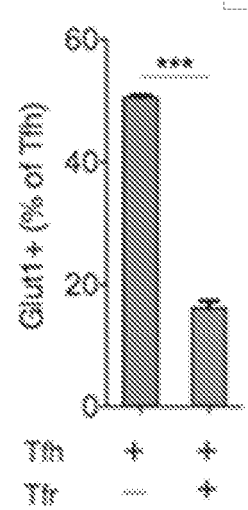
Figure 7E:
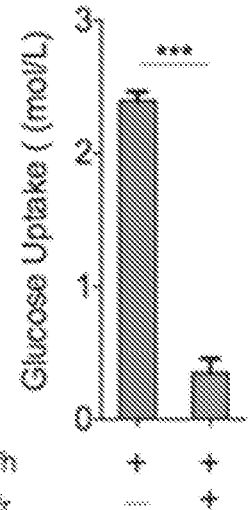
Figure 7E:
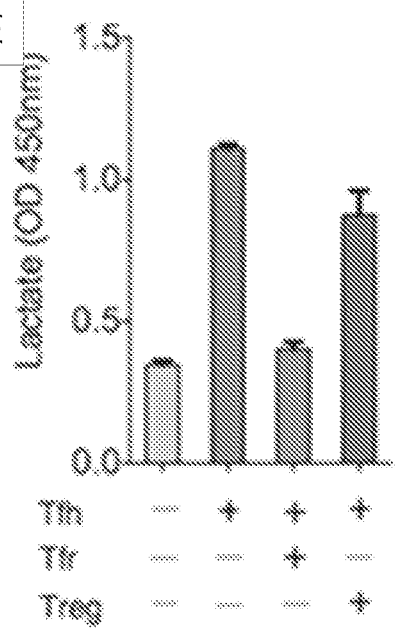
Figure 7F:
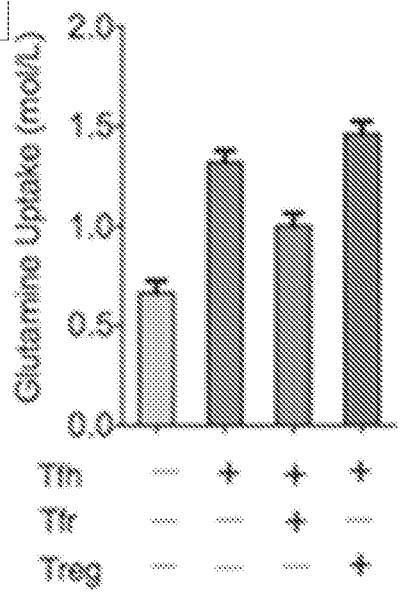

Whether or not metabolic pathways such as glycolysis were altered in suppressed B and TFH cells was confirmed. Glut1 is one of the most important transporters for glucose and is a marker for glycolytic cells. When Glut1 expression was measured in B and TFH cells from activated or suppressed cultures, it was found that TFR cells suppressed Glut1 expression in both B and TFH cells suggesting that TFR cells suppress glycolysis in both B and TFH cells (FIG. 7C). To determine if B and TFH cells utilized less glucose in the suppressed cultures glucose from the culture supernatants was analyzed. It was found that in cultures of TFH and B cells, large amounts of glucose were utilized, which was decreased strongly with the addition of TFR cells (FIG. 7D). Lactate is generated as a byproduct of glycolysis. When lactate production was measured in the culture supernatants, large amounts of lactate were produced when TFH cells were added to B cells, and that this lactate production was severely attenuated with TFR cells were additionally added (FIG. 7E). The suppression of lactate production was unique to TFR cells, as ICOS−CXCR5− Tregs from the same lymph node were not able to potently suppress lactate production. In addition to glucose, glutamine utilization was also suppressed by TFR cells, which correlated with the decreased glutaminolysis transcriptional signature that was measured by RNA-seq (FIG. 7F).

Figure 7G:
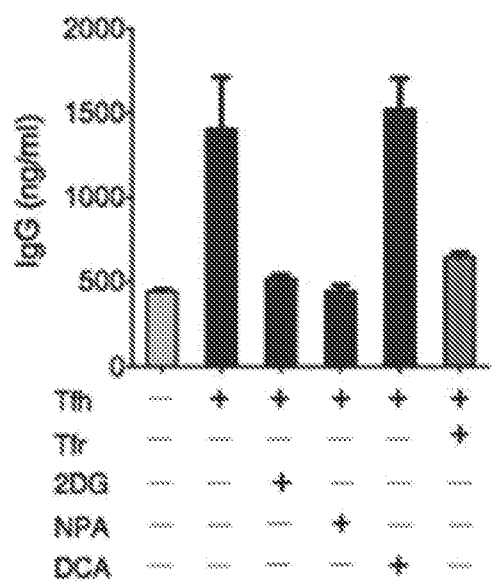

To determine if inhibiting glycolysis could recapitulate TFR suppression, cultures of B and TFH cells were performed with the addition of 2-deoxyglucose (2DG), a glucose analog that blocks glycolysis. When 2DG was added to activated cultures, a robust suppression of antibody production was found, similar to TFR suppression (FIG. 7G and FIG. 24). Similar results were found when 2-nitroproprionic acid (NPA) was added which inhibits the TCA cycle. However, the addition of dichloroacetate (DCA), which shifts metabolism from glycolysis to oxidative phosphorylation, did not alter antibody production. This data suggests that B cells can use multiple pathways of energy utilization and when one pathway is strongly inhibited, it results in attenuation of antibody production similar to suppression by TFR cells.

Figure 7H:
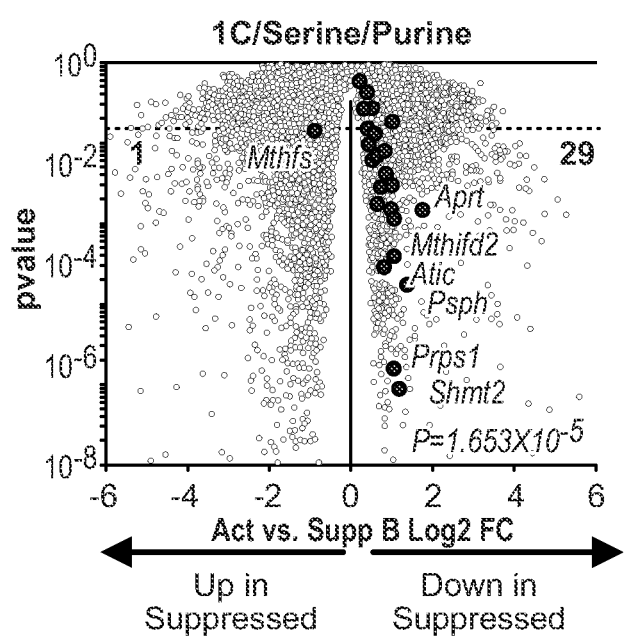
Figure 7I:
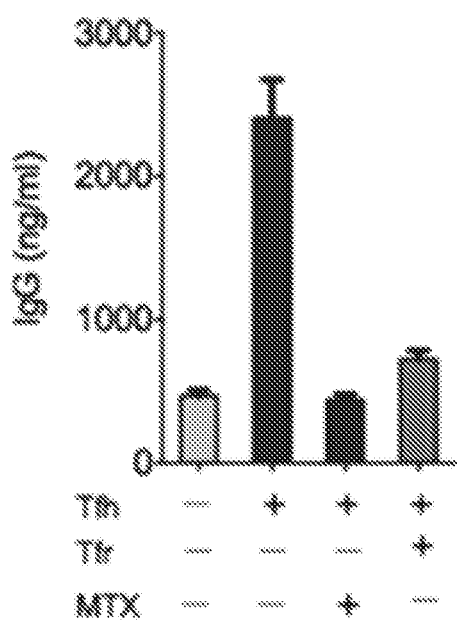
Figure 7J:
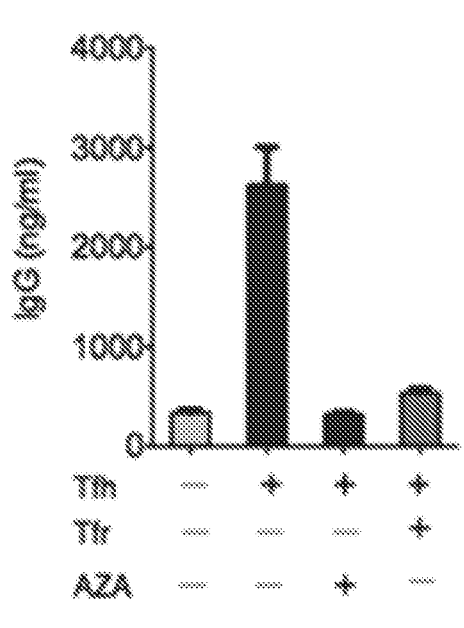

Next it was determined if the TFR cells also potently suppress serine, purine and 1-carbon metabolism since all key enzymes (with the exception of Mthfs) within this pathway have a lower transcript abundance in B cells upon TFR suppression (FIG. 7H). Reduced expression of genes encoding products involved in one-carbon metabolism in B cells suppressed by TFR cells was not due to altered proliferation, because the expression of Shmt1 and Shmt2 (a cytosolic enzyme and mitochondrial enzyme, respectively, in one-carbon metabolism that are upregulated within hours of lymphocyte activation32) were attenuated before the first cell division (FIG. 25). Inhibitors of purine metabolism have been used clinically in the context of autoimmunity to inhibit antibody production. Therefore, whether inhibitors of purine metabolism could recapitulate TFR suppression in vitro was determined. Methotrexate (MTX), a purine synthesis inhibitor, was added to cultures of B and TFH cells and found that MTX robustly suppresses antibody production in vitro even more so than TFR cells (FIG. 7I). Since methotrexate may have affects beyond inhibiting purine metabolism, an additional purine inhibitor azathioprine (AZA) was used. Addition of AZA to B and TFH cultures resulted in robust suppression of antibody secretion similar to MTX which was stronger than suppression by TFR cells alone (FIG. 7J). Both MTX and AZA also potently suppressed class switch recombination of B cells similar to TFR cells. Taken together these data demonstrate that TFR cells suppress multiple metabolic pathways in B cells and potently suppressing these pathways results in similar suppression of antibody production by B cells.

Figure 8B:
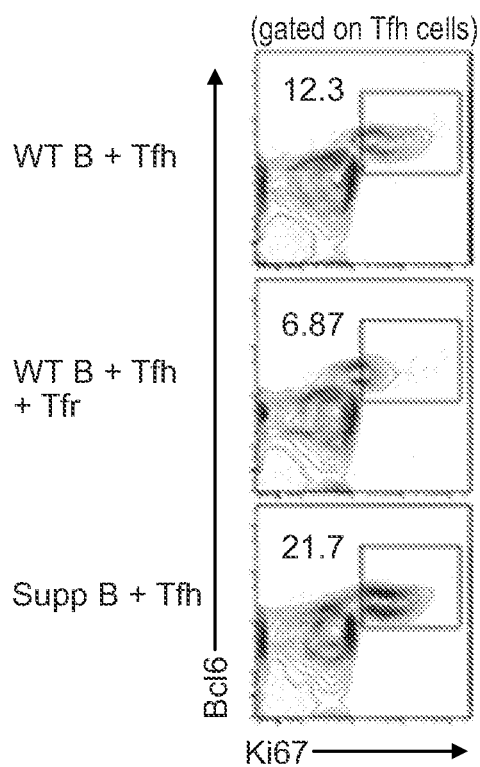
Figure 8C:
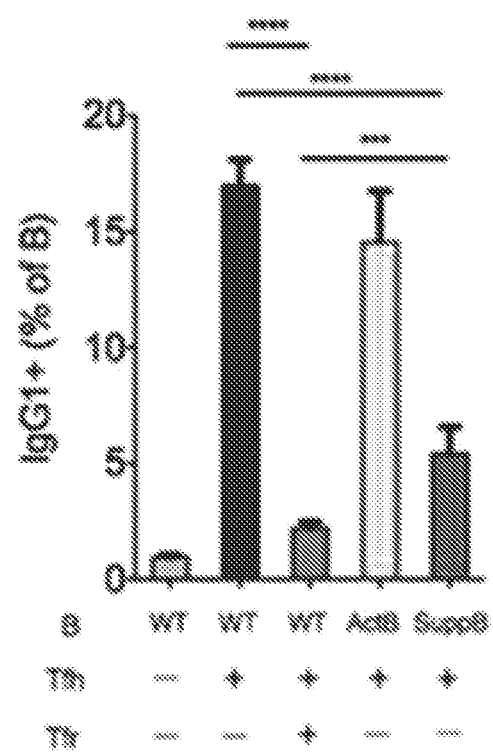
Figure 8D:
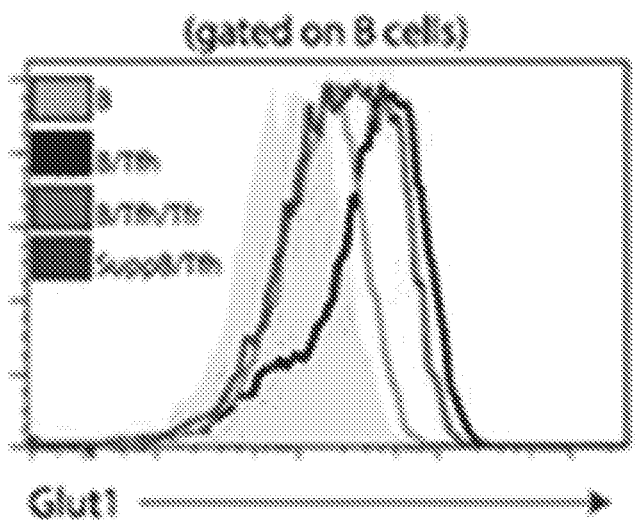
Figure 8E:
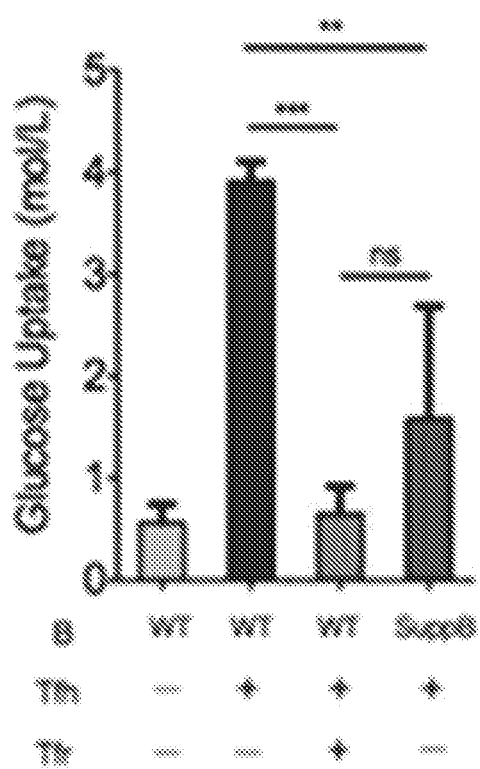

Example 5—TFR Suppression of B Cells Results in Prolonged Inhibition and Epigenetic Changes Next it was determined whether suppressed B cells were capable of becoming activated cells or whether TFR suppression elicits a long lasting suppression that continues after TFR cells are no longer present. To test this, the in vitro suppression assay was adapted. The activated or suppressed B and TFH cultures were set-up and after 3 days, sorted the activated or suppressed B cells. These B cells were cultured with new TFH cells in a secondary culture, and after 6 days analyzed the cultures (FIG. 8A). First, TFH cells were measured from these cultures. It was found that TFH cells cultured with suppressed B cells had Ki67 and Bcl6 containing suggesting that TFH cells from these cultures were activated by suppressed B cells (FIG. 8B and FIG. 26). However, when intracellular IgG1 in B cells from these cultures was analyzed, it was found that suppressed B cells restimulated by TFH cells were still severely defective in the ability to undergo class switch recombination (FIG. 8C). Since the previous examples suggest that TFR cells suppress B cell class switch recombination through downregulating metabolism, it would be expected that the suppressed B cells that were reactivated which have defective class switch recombination would also have defects in metabolism. To answer this question, Glut1 expression was analyzed in suppressed B cells that were reactivated with TFH cells and found that although Glut1 expression was higher than suppressed B cells from the primary culture, it was much lower than activated B cells (FIG. 8D). Additionally, when glucose uptake from cultures was measured, it was found that suppressed B cells with reactivation cultures had substantially less glucose utilized (FIG. 8E). Together these data indicate that B cells suppressed by TFR cells have defects in class switch recombination and metabolism which persists after TFR cells are no longer present.

Figure 8F:
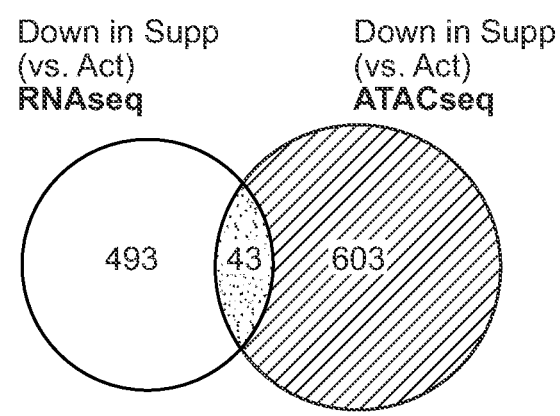
Figure 8G:
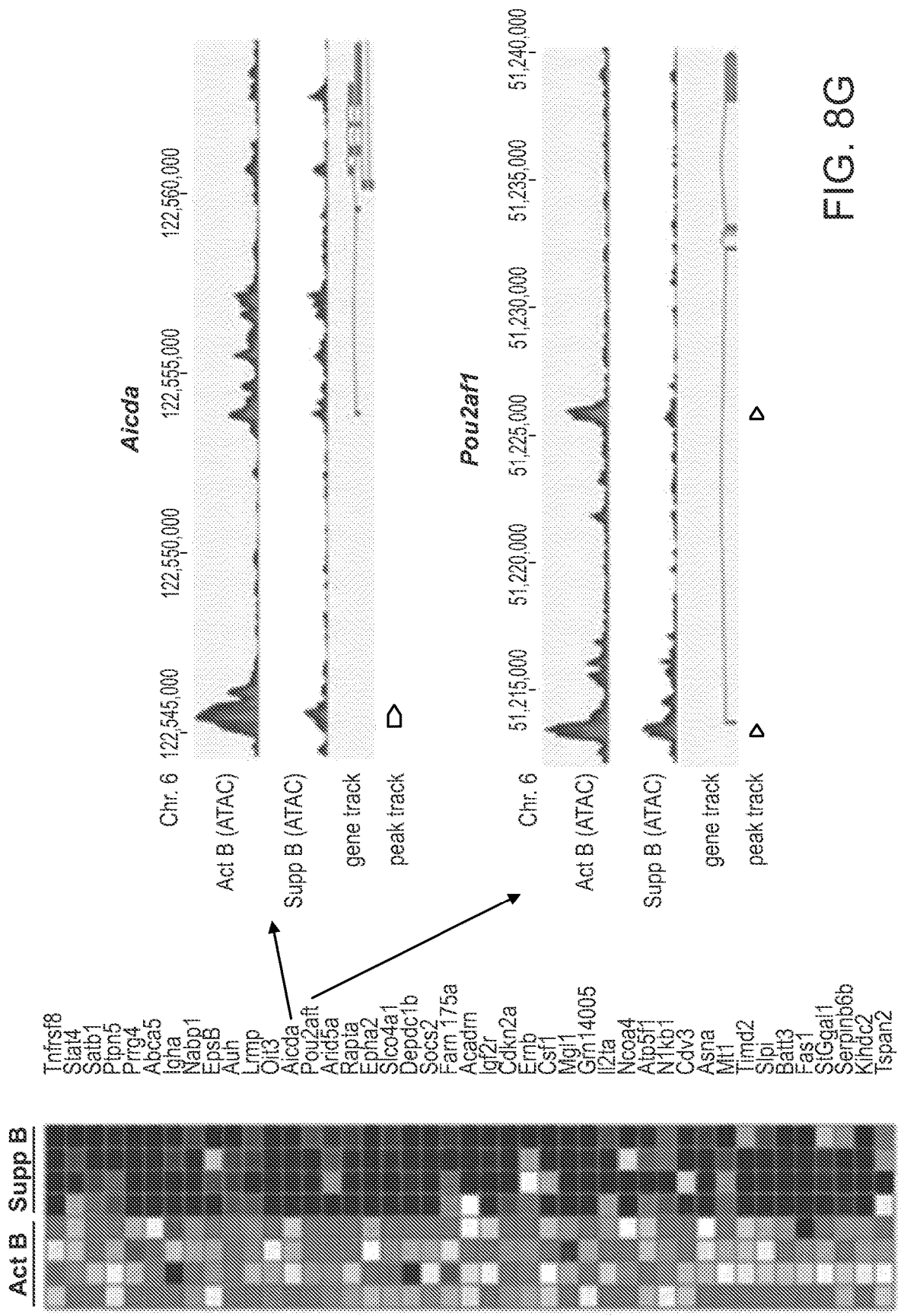

The findings that suppressed B cells maintain defective class switch recombination after TFR cells point to modification of the B cells. One possible explanation of this data is that TFR cells may cause epigenetic modifications to B cells during suppression and that these epigenetic modifications last longer than the presence of TFR cells. Therefore, chromatin accessibility was assessed utilizing assay for transposase-accessible chromatin using sequencing (ATAC-seq) to determine if any key B cell effector or metabolic genes showed any evidence of changes in accessibility, possibly due to epigenetic changes elicited by TFR cells. The in vitro suppression assay was performed as in FIG. 8A, except using NP-OVA instead of anti-CD3 and sorted activated and suppressed B cells 3 days after culture. 646 genes were found that demonstrated a statistical downregulation in accessibility in suppressed B cells compared to activated B cells (FIG. 8F). Of these genes, 43 also had lower expression at the RNA level. Aicda and Pou2af1, two essential B cell function genes whose transcripts were highly downregulaed at the RNA level also showed evidence of chromatin inaccessibility by ATAC-seq suggesting epigenetic modification (FIG. 8G). The Aicda locus showed less accessibility in a region ~8kb upstream of the Aicda TSS. This region is a known enhancer region where NF-kb, Stat6 and C/EBP transcription factors bind and is critical for AID expression20. Two peaks were found that showed evidence of inaccessibility in the Pou2af1 locus; one in close proximity to the TSS and one in an intronic region in between exons 1 and 2. Therefore, AID and Pou2af1, two genes that are essential for class switching and GC formation, may be inhibited by epigenetic modification elicited by TFR suppression which may explain suppression of B cells after TFR cells are no longer present.

To explore how the genes identified are regulated, the ATAC-seq data was overlaid with the 'B cell regulome' (a collection of confirmed interactions of promoters with long-range enhancers in B cells) defined by ChIA-pet techniques. The Aicda locus showed less accessibility in suppressed B cells than in activated B cells in two regions, one ~8 kilobases (kb) and another ~21 kb upstream of the Aicda transcriptional start site (TSS) (FIG. 27). These enhancer regions are essential for AID expression33,34. Seven putative enhancer regions in the Myc locus were identified that were less accessible in B cells suppressed by TFR cells than in activated B cells (FIG. 28). One peak was found that was less accessible in the Pou2af1 locus that was located in an intronic region in between exon 1 and exon 2 (FIG. 29). Many of the less-accessible regions in suppressed B cells were not at the TSS but were at sites of long-range enhancers (FIG. 28 and FIG. 29). When the distribution of all ATAC-seq regions was quantified relative to the location of the TSS, the less-accessible regions in B cells suppressed by TFR cells tended to be further away from the TSS than were all regions identified by ATAC-seq (FIG. 30). These data indicated that genes encoding products critical for B cell function, but not those encoding key metabolic enzymes, showed evidence of epigenetic regulation during suppression by TFR cells.

Interestingly, none of the key metabolic enzymes that were downregulated by RNAseq (see FIG. 7B) showed any clear evidence of DNA inaccessibility. However, 3 mitochondrial/metabolic genes did show evidence of inaccessibility; Atp5f1, Acadm and Auh. Atp5f1 functions in the electron transport chain during oxidative phosphorylation, a pathway suppressed globally at the RNA level. Acadm functions in mitochondrial fatty acid beta-oxidation pathway. Auh encodes an enzyme which functions to breakdown leucine and can bind to AU rich elements (AREs) in RNA. Taken together, these data indicate that select B cell function genes show evidence of epigenetic regulation during TFR suppression and with a few exceptions, metabolic genes are not epigenetically modulated by chromatin remodeling. This data suggests that TFR suppression primarily affects epigenetic modification of AID and Pou2af which may alter downstream B cell function and metabolism.

Example 6—IL-21 can Overcome TFR Mediated Suppression of B Cell Metabolism and Antibody Production The data indicates that TFR cells suppress B cells through targeted downregulation of B cell function genes and altered metabolism. It is possible that B cell function genes and multiple metabolic pathways cooperate to induce class switch recombination and antibody production in B cells. TFR suppression of B cells was not able to be rescued through bypassing any single metabolic pathway (FIG. 7A-FIG. 7J) suggesting that TFR suppression of multiple metabolic pathways and/or B cell genes contributes to suppression. Therefore, to determine ways to overcome suppressed B cells therapeutically, it is possible that both B cell genes and metabolism would need to be energized to overcome suppression. IL-21 is a cytokine which is essential in the germinal center reaction which is potently suppressed by TFR cells. IL-21 can also control metabolic processes in fat tissue, and has been shown to inhibit Treg suppression of effector cells. When IL-21 was added to suppression assays, the attenuation in proliferation of B cells mediated by TFR cells was rescued (FIG. 11A). Moreover, class switch recombination was much higher in suppressed conditions with the addition of IL-21, however, this did not quite reach activated culture levels (FIG. 11B). Addition of IL-21 to suppressed cultures mostly rescued the amount of secreted antibody compared to activated cultures, a result that did not occur when IL-4 was added (FIG. 11C). However, IL-6, another Stat3 signaling cytokine, was also able to rescue the suppression of antibody production.

Since metabolism is essential to facilitate B cell effector functions and is regulated by TFR cells, the metabolic potential of B cells was assessed in suppressed cultures with the addition of IL-21. Glut1 expression was completely rescued on B cells when IL-21 was added to suppressed cultures (FIG. 11D). Similarly, Glut1 expression on TFH cells was rescued when IL-21 was added to suppressed cultures. Glucose consumption in the culture was almost completely rescued when IL-21 was added to suppressed cultures (FIG. 11E). IL -21 and IL-6 were also able to substantially (although not completely) rescue lactate production in suppressed cultures (FIG. 11F). Therefore, addition of IL-21 can rescue the glycolytic function of suppressed B cells. It is possible that IL-21 rescues antibody production primarily through enhancing metabolism. To determine if enhanced glycolysis was required for the IL-21 rescue of antibody production in suppressed cultures, glycolysis was blocked to determine if antibody responses could still be rescued in the absence of enhanced metabolism. Blocking glycolysis resulted in the IL-21 not being able to rescue suppression (FIG. 11G). Therefore, IL-21 renders B cells resistant to TFR mediated suppression primarily by enhancing metabolism.

In order to determine which B cell function genes were rescued at the transcriptional level, RNA-seq transcriptional analysis was performed on B cells from activated cultures, from suppressed cultures, and suppressed cultures supplemented with IL-21. When B cell function genes was assessed (as in FIG. 2G) in suppressed vs. suppressed plus IL-21 cultures, only transcripts for the individual IgG isotypes (Ighg1, Ighg2c, Ighg2b, Igha) showed evidence of significant upregulation with addition of IL-21 (FIG. 11H). Only 12 genes were expressed differentially in B cells from suppressed cultures versus those from 'IL-21 rescue' cultures and also in B cells from suppressed cultures versus those from activated cultures, and of these genes, only Ighg1 and Ighg2c were 'rescued' with IL-21 (FIG. 31) Interestingly, the three most suppressed B cell function genes during TFR suppression, Aicda, Xbp1 and Pou2af1, did not show any evidence of rescue with IL-21. In the case of Aicda and Pou2af1, it is possible that this may be due to the epigenetic modification of these gene loci by TFR cells, however this was not tested directly.

Next whether metabolic pathways other than glycolysis could be rescued transcriptionally was determined. ssGSEA was performed on our RNA-seq samples and evidence of some rescue of many metabolic pathways with the addition of IL-21 (FIG. 11I) was found. Therefore, IL-21 overcomes TFR suppression by stimulating B cells as well as metabolic pathways.

Whether IL-21 restored antibody production by acting directly on B cells was determined. Suppression assays were performed using B cells lacking the receptor for IL-21 (Il21r−/−). Although baseline antibody responses were lower in cultures of Il21r−/− B cells with TFH cells than in those of Il21r+/+ B cells with TFH cells, no evidence was found that antibody responses were restored in suppressed cultures by the addition of IL-21 (FIG. 32). Loss of IL-21R did not abolish the increase in the number of B cells observed in suppressed cultures after the addition of IL-21 but did prevent the restoration of CSR and Glut1 expression (FIG. 40A-FIG. 40C). Since upregulation of GL7 is a robust indicator of B cell activation, its expression in suppressed cultures containing either Il21r+/+ B cells or Il21r−/− B cells and supplemented with IL-21 was compared. IL-21 restored GL7 expression when Il21r+/+ B cells were present but not when Il21r−/− B cells were present (FIGS. 33 and 34), which suggested that signaling through IL-21 into the B cells was essential for the restoration of B cell activation.

Since IL-21 could be affecting the TFH, B or TFR cell in the suppressed culture, whether the rescue of suppressed metabolism could be due to a combined effect of stimulating B cells and inhibiting TFR suppression (by acting directly on the TFR cell) was determined. When the TFR cells from suppressed cultures with or without addition of IL-21 was analyzed, it was found that the TFR cells in cultures that contained IL-21 had much less intracellular Ki67 staining suggesting that cell cycling is inhibited in TFR cells with the addition of IL-21 (FIG. 11J). Glut1 expression was higher in TFR cells in the presence of IL -21 than in its absence (FIG. 35), which suggested that IL-21 was able alter the metabolism of TFR cells as well as their activation. Therefore, IL-21 rescue of TFR cell suppression of B and TFH cells is the result of modulation of B cells as well as inhibiting TFR cells.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments described herein. Such equivalents are intended to be encompassed by the following claims.

What is claimed is:

1. A composition comprising T follicular regulatory (TFR) cells and a cytokine, wherein said composition has reduced immune suppressive activity,
    wherein the reduced immune suppressive activity results in a protective antibody response, and
    wherein the cytokine is IL-21 or IL-6.

2. The composition of claim 1, wherein the reduced immune suppressive activity is characterized by a boost in antibody production in vitro and in vivo as compared to native TFR cells.

3. A method of upregulating an immune response in a subject comprising administering to the subject, an effective amount of the composition of claim 1.

4. A vaccine comprising the composition of claim 1.

5. A method of preparing a composition comprising TFR cells having reduced immune suppressive activity comprising the steps of:
    a) obtaining an initial population of cells comprising TFR cells, T regulatory (Treg) progenitor cells, or both;
    b) contacting the cells ex vivo in the presence of a cytokine; and
    c) isolating the TFR cells from the population wherein the isolated TFR cells have reduced immune suppressive activity,
    wherein the reduced immune suppressive activity results in a protective antibody response, and
    wherein the cytokine is IL-21 or IL-6.

6. The method of claim 5, wherein the reduced immune activity results in a boost in antibody production.

7. The method of claim 5, wherein the initial population of cells is isolated from the peripheral blood, tissues or organs of one or more subjects.

8. The method of claim 5, further comprising sorting TFR cells and Treg progenitor cells from the cell population prior to contacting the cell with the cytokine.

9. The method of claim 5, further comprising the step of expanding the cell population.

10. A method of modulating an immune response in a subject in need thereof comprising:
 administering to the subject a) an effective amount of a composition comprising T follicular regulatory (TFR) cells and a cytokine, wherein the cytokine is IL-21 or IL-6.

11. The method of claim 10, wherein the TFR cells are administered conjointly or in combination with the cytokine.

12. The method of claim 10, wherein the TFR cells are contacted with the cytokine prior to administering to the subject.

13. The method of claim 10, wherein the TFR cells are isolated from the peripheral blood of a subject.

14. The method of claim 10, wherein the TFR cell modulation results in boosted antibody production.

15. The method of claim 10, wherein the method further comprises administering a vaccine to the subject.

16. The method of claim 10, comprising co-administering a composition comprising TFH cells and a vaccine.

17. The method of claim 10, wherein the composition is administered intravenously.

18. The method of claim 10, wherein the subject is afflicted with a disease or condition selected from the group consisting viral infection, bacterial infection, pathogenic infection, fungal infection, and cancer.

19. An adjuvant comprising a composition of TFH cells and a cytokine, wherein the adjuvant has an increased protective antibody response, wherein the cytokine is IL-21 or IL-6.

20. The adjuvant of claim 19, wherein the TFH cells are purified from the peripheral blood of a subject.

21. A method of boosting antibody production in a subject in need thereof comprising administering to the subject the adjuvant of claim 19.

* * * * *